United States Patent [19]
Norman et al.

[11] Patent Number: 6,103,709
[45] Date of Patent: Aug. 15, 2000

[54] THERAPEUTICALLY EFFECTIVE $1\alpha,25$-DIHYDROXYVITAMIN $D_3$ ANALOGS AND METHODS FOR TREATMENT OF VITAMIN D DISEASES

[75] Inventors: Anthony W. Norman; William H. Okamura, both of Riverside, Calif.

[73] Assignee: The Regents of the University of California, Oakland, Calif.

[21] Appl. No.: 09/073,723

[22] Filed: May 7, 1998

Related U.S. Application Data

[63] Continuation-in-part of application No. 08/558,717, Nov. 16, 1995, abandoned, which is a continuation-in-part of application No. 08/706,356, Aug. 30, 1996, abandoned, which is a continuation-in-part of application No. 08/249,385, May 25, 1994, abandoned, which is a continuation of application No. 08/173,561, Dec. 23, 1993, abandoned

[60] Provisional application No. 60/060,173, Sep. 26, 1997.

[51] Int. Cl.$^7$ .................... C07C 401/00; A61K 31/59
[52] U.S. Cl. ............................. 514/167; 552/653
[58] Field of Search .................. 514/167; 552/653

[56] References Cited

U.S. PATENT DOCUMENTS

| | | | |
|---|---|---|---|
| 4,670,190 | 6/1987 | Hesse et al. | 260/397 |
| 4,804,502 | 2/1989 | Baggiolini et al. | 260/397.2 |
| 5,087,619 | 2/1992 | Baggiolini et al. | 514/167 |
| 5,145,846 | 9/1992 | Baggiolini et al. | 514/167 |
| 5,158,944 | 10/1992 | Makino et al. | 514/167 |
| 5,250,523 | 10/1993 | DeLuca et al. | 514/167 |
| 5,362,719 | 11/1994 | Godtfredsen | 514/167 |
| 5,378,695 | 1/1995 | Calverley et al. | 514/167 |
| 5,389,622 | 2/1995 | Posner et al. | 514/167 |
| 5,395,829 | 3/1995 | Hollick | 514/167 |
| 5,401,732 | 3/1995 | Calverley et al. | 514/167 |
| 5,403,832 | 4/1995 | Posner et al. | 514/167 |
| 5,436,401 | 7/1995 | Kato et al. | 552/610 |
| 5,552,392 | 9/1996 | DeLuca et al. | 514/167 |
| 5,612,325 | 3/1997 | Hansen et al. | 514/167 |
| 5,710,142 | 1/1998 | Calverley et al. | 514/167 |

FOREIGN PATENT DOCUMENTS

| | | |
|---|---|---|
| 650148 | 6/1994 | Australia . |
| 4-89473 | 3/1992 | Japan . |
| 4-89474 | 3/1992 | Japan . |
| 6-72994 | 3/1994 | Japan . |
| 6-256300 | 9/1994 | Japan . |

OTHER PUBLICATIONS

PCT International Application Publication No. WO 94/07851, Published Apr. 14, 1994, by Hansen, Et Al., Novel Vitamin D Analogues.

*Primary Examiner*—Jose' G. Dees
*Assistant Examiner*—Barbara Badio
*Attorney, Agent, or Firm*—Hana Verny

[57] ABSTRACT

A method for treatment of diseases caused by deficiency or overproduction of the vitamin $D_3$ metabolites by administering analogs of $1\alpha,25$-dihydroxyvitamin $D_3$. These analogs are selective agonists or antagonists for the genomic and rapid nongenomic cellular responses. A pharmaceutical composition comprising $1\alpha,25$-dihydroxyvitamin $D_3$ analog.

19 Claims, 20 Drawing Sheets

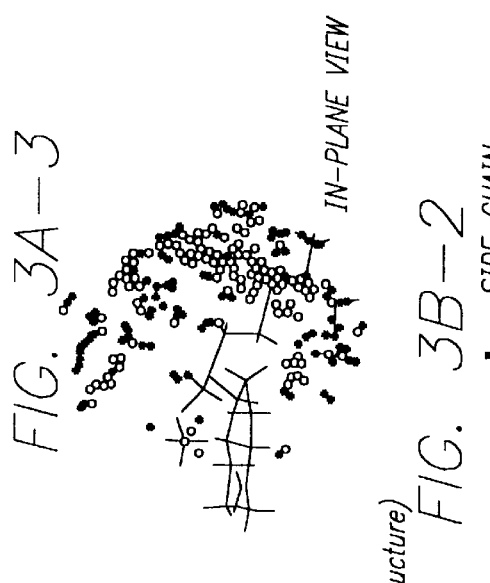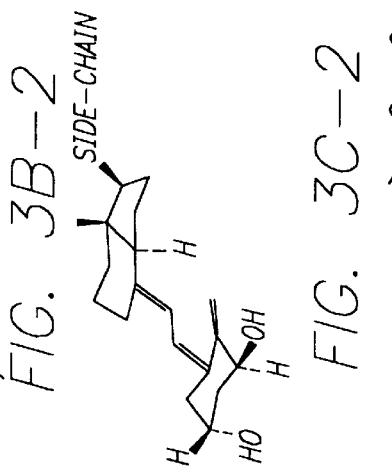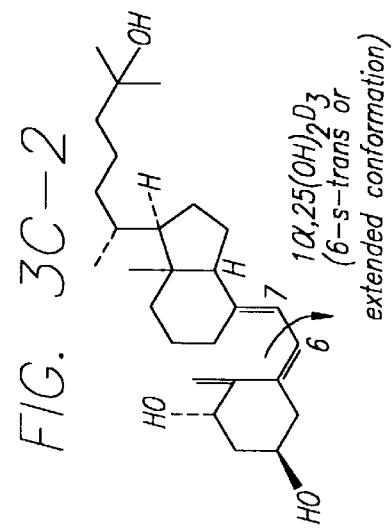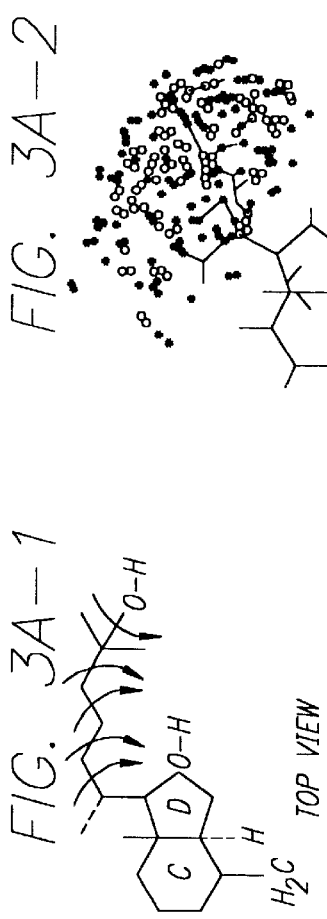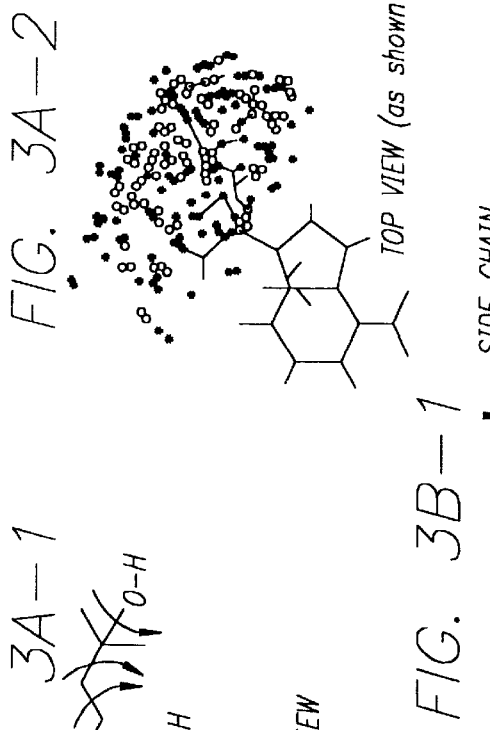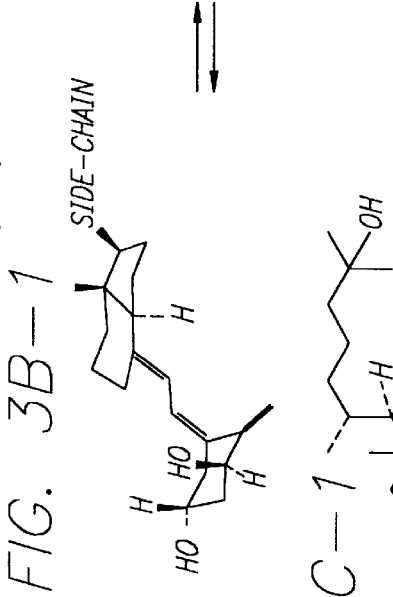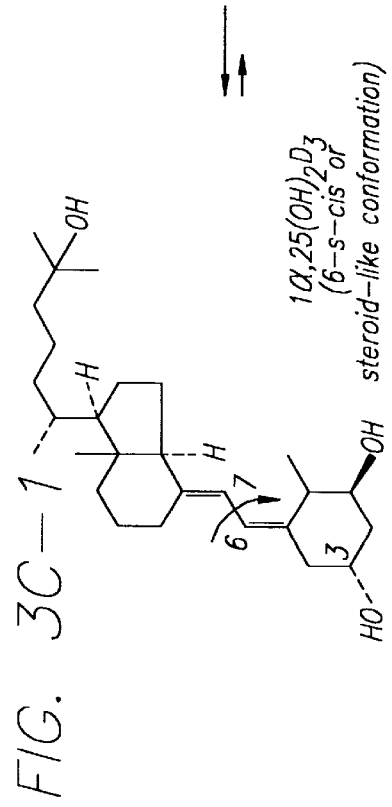

FIG. 5
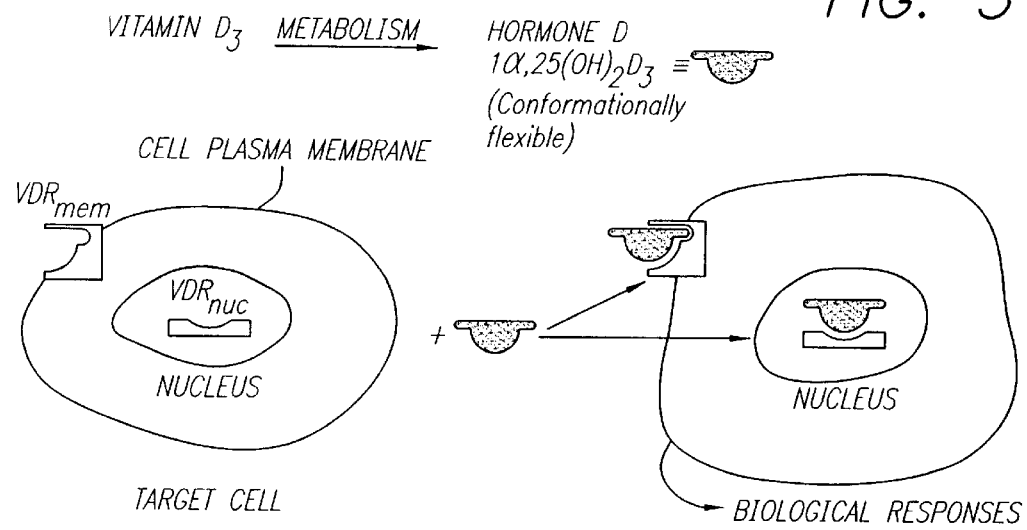
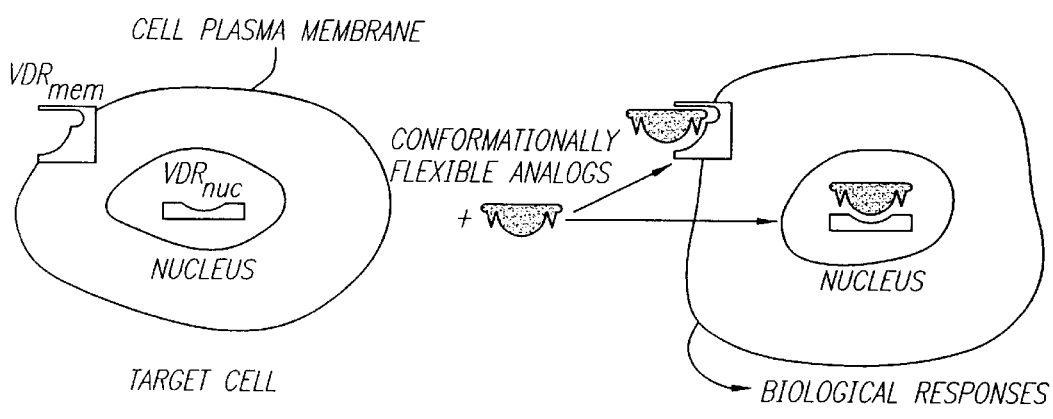
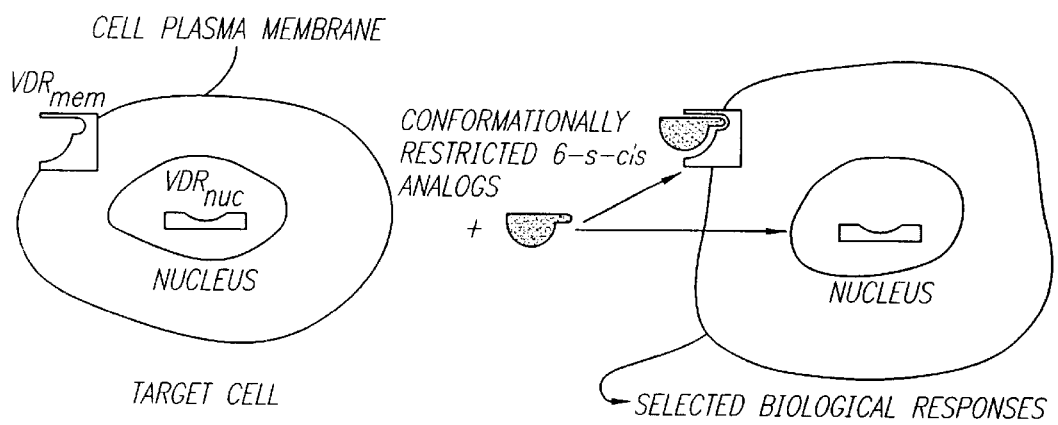

THERAPEUTICALLY EFFECTIVE 1α,25-DIHYDROXYVITAMIN D₃ ANALOGS AND METHODS FOR TREATMENT OF VITAMIN D DISEASES

This application is the continuation-in-part of the co-pending application Ser. No. 081558,717, filed on Nov. 16, 1995, abandoned, and of co-pending application Ser. No. 08/706,356, filed on Aug. 30, 1996, abandoned, that are continuations-in-part of application Ser. No. 08/249,385, filed on May 25, 1994, abandoned, which is a continuation of application Ser. No. 08/173,561, filed on Dec. 23, 1993, abandoned, the application portion concerning the MAP kinase subject matter is based on the Provisional Application Ser. No. 60/060,173 filed Sep. 26, 1997.

This invention was made with government support under Training Grant Nos. DK-09012 and DK-16,595, awarded by the National Institutes of Health. The government has certain rights in this invention.

BACKGROUND OF THE INVENTION

Field of Invention

The current invention concerns a method for treatment of diseases caused by deficiency or overproduction of the vitamin $D_3$ metabolites. In particular, the current invention concerns therapeutic properties of 1α,25-dihydroxyvitamin $D_3$ analogs which are selective agonists or antagonists for the genomic ana rapid nongenomic cellular responses affecting calcium and phosphorus absorption, resorption, mineralization, collagen maturation of bone and tubular reabsorption of phosphorus. The analogs of the invention are useful for treatment of bone diseases such as rickets, osteomalacia, osteoporosis, osteopenia, osteosclerosis, renal osteodystrophy; skin diseases, such as psoriasis; thyroid diseases, such as medullary carcinoma; brain diseases, such as Alzheimer's disease; parathyroid diseases, such as hyperparathyroidism, hypoparathyroidism, pseudoparathyroidism or secondary parathyroidism; liver and pancreas diseases, such as diabetes, cirrhosis, obstructive jaundice or drug-induced metabolism; intestine diseases, such as glucocorticoid antagonism, idiopathic hypercalcemia, malabsorption syndrome, steatorrhea, or tropical sprue; kidney disease, such as chronical renal disease, hypophosphatemic vitamin D-resistant rickets or vitamin D-dependent rickets; lung diseases, such as sarcoidosis; and for treatment of any other disease in which 1α,25-dihydroxyvitamin $D_3$ or its prodrugs are involved.

BACKGROUND ART AND RELATED DISCLOSURES

Vitamin D deficiency is known to lead to serious diseases, such as rickets in children and osteomalacia in adults. Vitamin D is a prohormone of several active metabolites that behave as hormones. The most important of those metabolites is 1α,25(OH)₂-vitamin $D_3$.

Vitamin $D_3$, also known as cholecalciferol or activated 7-dehydrocholesterol, is a secosteroid responsible for a wide variety of biological responses in higher animals that include maintenance of calcium homeostasis, immunomodulation and selected cell differentiation.

Vitamin $D_3$ is formed in human skin by exposure to ultraviolet radiation from sun. In the skin, previtamin $D_3$ is synthesized photochemically from 7-dehydrocholesterol and is slowly isomerized to vitamin $D_3$. Vitamin $D_3$ is converted in the liver into 25-hydroxyvitamin $D_3$, the major circulating form of vitamin $D_3$ metabolite. In the kidney and in some other tissues, 25(OH)$D_3$ is further hydroxylated to a more metabolically active form known as 1α,25-dihydroxyvitamin $D_3$ [1α,25(OH)₂$D_3$] whose primary function is to increase calcium absorption from the intestine and promote normal bone formation and mineralization. Vitamin D and its derivatives are, therefore, important substances for calcium homeostasis in the human body.

1α,25-dihydroxyvitamin $D_3$ [1α,25(OH)₂$D_3$] is a steroid hormone derived from its parent vitamin $D_3$ by sequential hydroxylation in the liver and kidney. α,25-dihydroxyvitamin $D_3$ is active in regulating mineral homeostasis, cell differentiation and proliferation. Many biological functions of 1α,25(OH)₂$D_3$ are mediated by its nuclear receptor [$VDR_{nuc}$]. (*Endocr. Rev.*, 16: 200–257 (1993)).

Vitamin $D_3$, itself, is biologically inert. However, metabolism of vitamin $D_3$ to its metabolites, such as 1α,25-dihydroxyvitamin $D_3$ [1α,25(OH)₂$D_3$], results in the formation of biologically active compounds, which are responsible for two main types of biological responses, namely slow genomic and rapid nongenomic responses, involved in the vitamin D endocrine system function.

Slow genomic responses of 1α,25(OH)₂$D_3$ are generated by its interaction with nuclear receptors. The result of this interaction with nuclear receptors is the regulation of gene transcription (*Crit. Rev. Eukar. Gene Exp.*, 2:65–109 (1992), *Annual Rev. Nutr.*, 11:189–216 (1991), *Vitamin D: Gene Regulation, Structure-Function Analysis and Clinical Application*, Norman, A. W., Bouillon, R., and Thomasset, M., Eds., pp. 146–154, Walter de Gruyter, Berlin, Germany (1991)).

The nuclear receptor for 1α,25(OH)₂$D_3$ has been shown to be present in 30 different tissues and it belongs to the same super family of proteins that includes receptors for the steroid hormones, retinoic acid and thyroxine (*Crit. Rev. Eukar. Gene Exp.*, 2:65–109 (1992), *FASEB J.*, 2:3043–3053 (1988), *Endocr. Rev.*, 3:331–366 (1982)).

In addition to the slow genomic responses, it has been recently discovered that 1α,25(OH)₂$D_3$ also mediates biological responses by a rapid nongenomic mechanism (*Vitamin D: Gene Regulation, Structure-Function Analysis and Clinical Application*, Norman, A. W., Bouillon, R., and Thomasset, M., Eds., pp. 146–154, Walter de Gruyter, Berlin, Germany (1991); and *Endocrinology*, 115:1476–1483 (1984). Recent discoveries by inventors and others have identified a series of rapid non-genomic effects of 1α,25(OH)₂$D_3$ that occur within seconds to minutes of exposure of cells to this steroid hormone (Rapid biological responses mediated by 1α,25(OH)₂-vitamin $D_3$: A case study of transcaltachia, pp. 233–256, in Vitamin D, Feldman D. M., Glorieux, F. H., Pike, J. W., Eds., Academic Press, San Diego, Calif., (1997)). Evidence supporting the existence of a membrane receptor ($VDR_{mem}$) for 1α,25(OH)₂$D_3$ which mediates the initiation of rapid responses in some cells is described in *J. Biol. Chem.*, 264:20403–20406 (1989); and *J. Biol. Chem.*, 269:23750–23756 (1994).

The rapid nongenomic responses of 1α,25(OH)₂$D_3$ have been demonstrated in a variety of systems which include transcaltachia, a rapid stimulation of intestinal calcium transport in the perfused chick intestine involving the opening of $Ca^{2+}$ channels, as described in *J. Biol. Chem.*, 264:20265–20274 (1989); a rapid increase of intracellular $Ca^{2+}$ in human keratinocytes and skeletal muscle, as described in *Brit. J. Dermatol.*, 124:230–235 (1991) and *Biochem T.*, 281:349–352 (1992); rapid opening of voltage-gated $Ca^{2+}$, as described in *Am. J. Physiol.*, 265:F705:F711

(1993); chloride channels in the ROS 17/2.8 cell line, as described in *Biochem. Biophys. Res. Commun.*, 225:551–556 (1996); rapid stimulation of sodium proton exchange in opossum kidney cells, as described in *Pflugers Arch.*, 424:391–397 (1993)]; rapid action on phospholipid metabolism in several tissues and cell lines, as described in *Endocrinology*, 127:2738–2743 (1990) and *Am. J. Physiol.*, 249:F117–F-123 (1985); rapid activation of protein kinase C in rat epithelium cells, as described in *J. Clin. Invest.*, 85:1296–1303 (1990); and rapid activation of mitogen-activated protein kinase (MAP-kinase or $p42^{mapk}$) in hepatic Ito cells and human keratinocytes, as described in *J. Biol. Chem.*, 270:3642–3647 (1995) and *J. Invest. Dermatol.*, 106:1212–1217 (1996).

Other rapid nongenomic cellular responses which are mediated by $1\alpha,25(OH)_2D_3$ include opening of voltage-gated $Ca^{2+}$ channels in rat osteosarcoma cells, as described in *Endocrinology*, 127:2253–2262 (1990) and *Am. J. Physiol.*, 249:F117–F123 (1985), as well as other rapid effects in kidney, as described in *FEBS Lett.*, 259:205–208 (1989), in liver, as described in *Endocrinology*, 127:2738–2743 (1990), in parathyroid cells, as described in *J. Biol. Chem.*, 264:20403–20406 (1989) and in intestine, as described in *J. Bone Min. Res.*, 7:457–463 (1992).

The rapid actions of $1\alpha,25(OH)_2D_3$ on the cell membrane are postulated to regulate cell biological functions and potentially to interact with other membrane-mediated kinase cascades or to engage in cross-talk with the cell nucleus to modify genomic responses of cell differentiation and proliferation as studied in the human leukemic NB4 cell line in *Endocrinology*, 139:457–465 (1998).

Enzyme MAP-kinase belongs to the family of serine/threonine protein kinases which can be activated by phosphorylation of a tyrosine residue induced by mitogens or cell differentiating agents, as described in *Trends Biochem. Sci.*, 17:233–238 (1992); and *J. Cell Biol.*, 12:1079–1088 (1993). MAP-kinase integrates multiple intracellular signals transmitted by various second messengers and regulates many cellular functions by phosphorylation of several cytoplasmic kinases and nuclear transcription factors including the EGF receptor, c-Myc and c-Jun, as described in *Science*, 260:315–319 (1993). However, until now it was unknown if the differentiation of NB4 cells by $1\alpha,25(OH)_2D_3$ involves the activation of MAP-kinase.

The human acute promyeolocytic leukemia cell line (NB4) is one model for study of the rapid membrane actions of $1\alpha,25(OH)_2D_3$. $1\alpha,25(OH)_2D_3$ is required during the priming phase of NB4 cell differentiation, as described in *J. Biol. Chem.*, 270:1596–15965 (1995). Tyrosine phosphorylation was reported to be involved in this priming phase process described in *Exp. Cell Res.*, 222:61–69 (1996). It is, however, not clear which tyrosine phosphorylation cascade plays a role in this priming phase.

A second cellular model for the study of rapid responses are primary enterocytes (intestinal mucosa cells) which can be obtained from chicks and rats. Both of these cellular systems have been employed for the study of $1\alpha,25(OH)_2D_3$-mediated rapid responses related to intestinal $Ca^{2+}$ absorption. It is anticipated that a series of third cellular models will include transformed breast cancer, prostate cancer and colon cancer cell lines. All these cells are known to be responsive to $1\alpha,25(OH)_2D_3$.

Since the deficiency or overproduction of vitamin $D_3$ metabolites result in serious disturbance of homeostasis, it would be important to have readily available compounds which would efficiently substitute these metabolites and act in the same or similar manner on the important physiological functions regulated by vitamin D endocrine system.

It is therefore a primary objective of this invention to provide analogs of vitamin $D_3$ metabolites which are able to act rapidly, specifically and in the same manner as the vitamin $D_3$ metabolites themselves on the genomic cellular apparatus and also to elicit rapid nongenomic responses correcting the vitamin $D_3$ caused deficiencies.

All patents, patent application, inventors published articles and other publications cited herein are hereby incorporated by reference.

SUMMARY

One aspect of the current invention is a method for treatment of diseases connected with or caused by vitamin $D_3$ deficiency or overproduction, by providing a subject in need of such treatment a vitamin $D_3$ analog which is either an agonist of vitamin $D_3$ or its antagonist, wherein the analog is selected from the group of compounds listed in Table 1.

Another aspect of the current invention is a method for treatment of bone diseases such as rickets, osteomalacia, osteoporosis, osteopenia, osteosclerosis or renal osteodystrophy; skin diseases, such as psoriasis; thyroid diseases, such as medullary carcinoma; brain diseases, such as Alzheimer's; parathyroid diseases, such as hyperparathyroidism, hypoparathyroidism, pseudoparathyroidism or secondary parathyroidism; liver and pancreas diseases, such as diabetes, cirrhosis, obstructive jaundice or drug-induced metabolism; intestine diseases, such as glucocorticoid antagonism, idiopathic hypercalcemia, malabsorption syndrome, steatorrhea or tropical sprue; kidney disease, such as chronical renal disease, hypophosphatemic vitamin D-resistant rickets or vitamin D-dependent rickets; lung diseases, such as sarcoidosis; or any other disease in which $1\alpha,25$-dihydroxyvitamin $D_3$ or its pro-drugs are involved.

Another aspect of the current invention is a method for treatment of vitamin $D_3$ deficiencies by providing $1\alpha,25$-dihydroxyvitamin $D_3$ analogs which are selective agonists or antagonists for the genomic and rapid nongenomic cellular responses affecting calcium and phosphorus absorption, resorption, mineralization, collagen maturation of bone and tubular reabsorption of phosphorus. Still another aspect of the current invention is a pharmaceutical composition comprising a $1\alpha,25$-dihydroxyvitamin $D_3$ analog useful for treatment of rickets, osteomalacia, osteoporosis, osteopenia, osteosclerosis, renal osteodystrophy, psoriasis, medullary carcinoma, Alzheimer's, hyperparathyroidism, hypoparathyroidism, pseudoparathyroidism, secondary parathyroidism, diabetes, cirrhosis, obstructive jaundice or drug-induced metabolism, glucocorticoid antagonism, idiopathic hypercalcemia, malabsorption syndrome, steatorrhea, tropical sprue, chronical renal disease, hypophosphatemic vitamin D receptor (VDRR), vitamin D-dependent rickets, sarcoidosis.

Another aspect of the current invention is a method for treatment of the above-listed diseases wherein the analog is selected from the group consisting of analog JM, namely $1\alpha,25(OH)_2$7-dehydrocholesterol; analog JN, namely, $1\alpha,25(OH)_2$-lumisterol$_3$; analog JO, namely, $1\alpha,25(OH)_2$-pyrocalciferol$_3$; analog JP, namely, $1\alpha,25(OH)_2$-isopyrocalciferol$_3$; analog HS, namely, $1\alpha,18,25(OH)_3$-$D_3$; analog GE, namely, 14-epi-1,25(OH)$_2$-$D_3$; analog GF, namely, 14-epi-1,25(OH)$_2$-pre-$D_3$; analog JR, namely, $1\alpha,25(OH)_2$-7,8-cis-$D_3$; analog JS, namely, $1\alpha,25(OH)_2$-5,6-trans-7,8-cis-$D_3$; analog HL, namely, $1\beta,25(OH)_2$-$D_3$;

analog HH, namely, 1α,25(OH)$_2$-3-epi-D$_3$; analog HJ, namely, 1α,25(OH)$_2$-epi-D$_3$; analog JV, namely, (1S,3R, 6S)-7,19-retro-1,25(OH)$_2$-D$_3$, or (6-(β)-1,25-vinylallene; analog JW, namely, (1S,3R,6S)-7,19-retro-1,25(OH)$_2$-D$_3$, or (6-(α)-1,25-vinylallene; analog JX, namely, 22-(p-hydroxyphenyl)-23,24,25,26, 27-pentanor-D$_3$; analog JY, namely, 22-(m-hydroxyphenyl)-23,24,25,26,27-pentanor-D$_3$; and analog IB, namely 23-[m(dimethylhydroxymethyl) phenyl]-22-yne-24, 25, 26, 27-tetranor-1α-hydroxy-D$_3$.

Still yet another aspect of the current invention is a method for treatment of diseases which require rapid non-genomic stimulation and release of calcium ions by intestine, kidney, parathyroid cells, liver and other organs during homeostatic responses and correction of pathological conditions in which the vitamin D$_3$ or 1α,25(OH)$_2$D$_3$ are involved by providing a subject in need thereof an analog of the invention.

Still another aspect of the current invention is a method for treatment of diseases caused by deficiencies or overproduction of vitamin D$_3$ or 1α,25(OH)$_2$D$_3$ or their functional deficiencies by providing a subject in need of correcting these deficiencies with an analog of vitamin D$_3$ in an amount sufficient to ameliorate the disease.

Another aspect of the current invention is a method for controlling the rapid nongenomic responses mediated by 1α,25-(OH)$_2$D$_3$ by treating the subject in need of such treatment with an antagonist which is 1β,25(OH)$_2$D$_3$, or a pharmaceutical composition comprising said antagonist.

Another aspect of the current invention concerns a method for selective activation of vitamin D-related rapid responses.

Still another aspect of the current invention is a method for selective inhibition of vitamin D-related rapid nongenomic responses.

Another aspect of the current invention is 1α,25-dihydroxyvitamin D$_3$ and its 6-s-cis analogs, which are selective agonists for the activation of MAP-kinase.

Still yet another aspect of the current invention is a pharmaceutical composition comprising an analog of the invention or its pharmaceutically acceptable salt.

Definitions

As defined herein:

"6-cis-orientation" means a geometrical orientation resulting in an isomer having a spatial arrangement where a given atom, positioned on each side of the carbon—carbon axis, is in the same side location relative to the carbon axis.

"6-trans-orientation" means a geometrical orientation resulting in an isomer having a spatial arrangement where a given atom positioned on each side of the carbon—carbon axis is in opposite location relative to the carbon axis.

"Agonist" means a compound capable of combining with receptors to initiate the compound's actions. The agonist possesses affinity for the receptor.

"Antagonist" means a compound that prevents, blocks, neutralizes or impedes the action of an agonist.

"1α,25(OH)$_2$D$_3$" means 1α,25-dihydroxyvitamin D$_3$.

"D$_3$" means vitamin D$_3$. The official IUPAC name for vitamin D$_3$ is 9,10-secocholesta-5,7,10(19)-trien-3β-ol.

"Transcaltachia" means the rapid hormonal stimulation of intestinal Ca$^{2+}$ absorption.

"VDR" is a generic term that means 1α,25(OH)$_2$D$_3$ receptors that include VDR$_{nuc}$ and VDR$_{mem}$.

"VDRnuc" means nuclear receptor for 1α,25(OH)$_2$D$_3$ interacting with 1α,25(OH)$_2$D$_3$ or with the analogs of the invention.

"VDR$_{mem}$" means membrane receptor for 1α,25(OH)$_2$D$_3$ interacting with 1α,25(OH)$_2$D$_3$ or with the analogs of the invention.

"Ligand" means any small organic molecule that has a specific affinity for its cognate receptor. For example, the ligand for the estrogen nuclear receptor is estradiol or its analogs. The ligand for the 1α,25(OH)$_2$D$_3$ receptor, either VDR$_{nuc}$ or VDR$_{mem}$ is 1α,25(OH)$_2$D$_3$ or its analogs.

"PMSF" means phenylmethylsulfonyl fluoride.

"EGTA" means ethylene-bis(oxyethylenenitrilo)-tetraacetic acid.

"HEPES" means 4-(2-hydroxyethyl)-1-piperazineethane-sulfonic acid.

"PKC" means protein kinase C.

"MAP-kinase" means mitogen activated protein kinase.

"Secosteroids" means compounds in which one of the cyclopentanoperhydrophenanthrene rings of the steroid ring structure is broken. In the case of vitamin D$_3$, the 9–10 carbon—carbon bond of the B ring is broken generating a seco-B steroid.

"Rapid response" or "rapid nongenomic response" means a rapid non-genomic effect of 1α,25(OH)$_2$D$_3$ or analog thereof generated by interaction of 1α,25(OH)$_2$D$_3$ or analog thereof with the membrane receptor, that is observed within seconds to minutes following the exposure of cells to these compounds.

"Genomic response" or "slow genomic response" means a biological response generated by interaction of 1α,25(OH)$_2$D$_3$ or the analog thereof with the cell nuclear receptor resulting in the regulation of gene transcription. Slow genomic responses are observed within several minutes to several days.

"DBP" means vitamin D binding protein.

"HRE" means hormone response element. Hormone response elements are composed of a specific sequence of about 6–12 nucleotides in the promoter region of the specific DNA constituting a gene which is regulated by steroid hormone receptors, including the nuclear receptor for 1α,25 (OH)$_2$D$_3$.

"Target cell" means any cell in the body that possess either membrane receptors (VDR$_{mem}$) or nuclear receptors (VDR$_{nuc}$) for 1α,25(OH)$_2$D$_3$.

BRIEF DESCRIPTION OF DRAWINGS

FIG. 5 represents a general model describing how 1α,25 (OH)$_2$D$_3$ and analogs of the invention, both conformationally flexible (FIGS. 5A and 5B) and conformationally restricted (FIG. 5C), generate biological responses.

DETAILED DESCRIPTION OF THE INVENTION

I. Mode of Action of Vitamin D

A. Vitamin D

Vitamin D is essential for life in higher animals. It is one of the most important biological regulators of calcium metabolism. Along with the two peptide hormones, parathyroid hormone and calcitonin, vitamin D is responsible for the minute-by-minute as well as the day-to-day maintenance of calcium/mineral homeostasis. These important biological effects are achieved as a consequence of the metabolism of vitamin D into a family of metabolites. One of these metabolites, namely 1α,25(OH)$_2$-vitamin D$_3$ [1α,25(OH)$_2$D$_3$] is considered to be a steroid hormone and therefore the number of the biological responses attributable to the parent vitamin D occur in a steroid hormone-like fashion through its metabolite 1α,25(OH)$_2$D$_3$.

1α,25(OH)$_2$D$_3$ has additional multidisciplinary actions in tissues not primarily related to mineral metabolism, such as, for example, its effects on cell differentiation and proliferation including interaction with cancer cells detectable in leukemia, breast, prostate, colon tumor growth, the immune system, skin, selected brain cells, and its participation in the process of peptide hormone secretion exemplarized by parathyroid hormone or insulin.

B. Vitamin D Endocrine System

Figure 1:
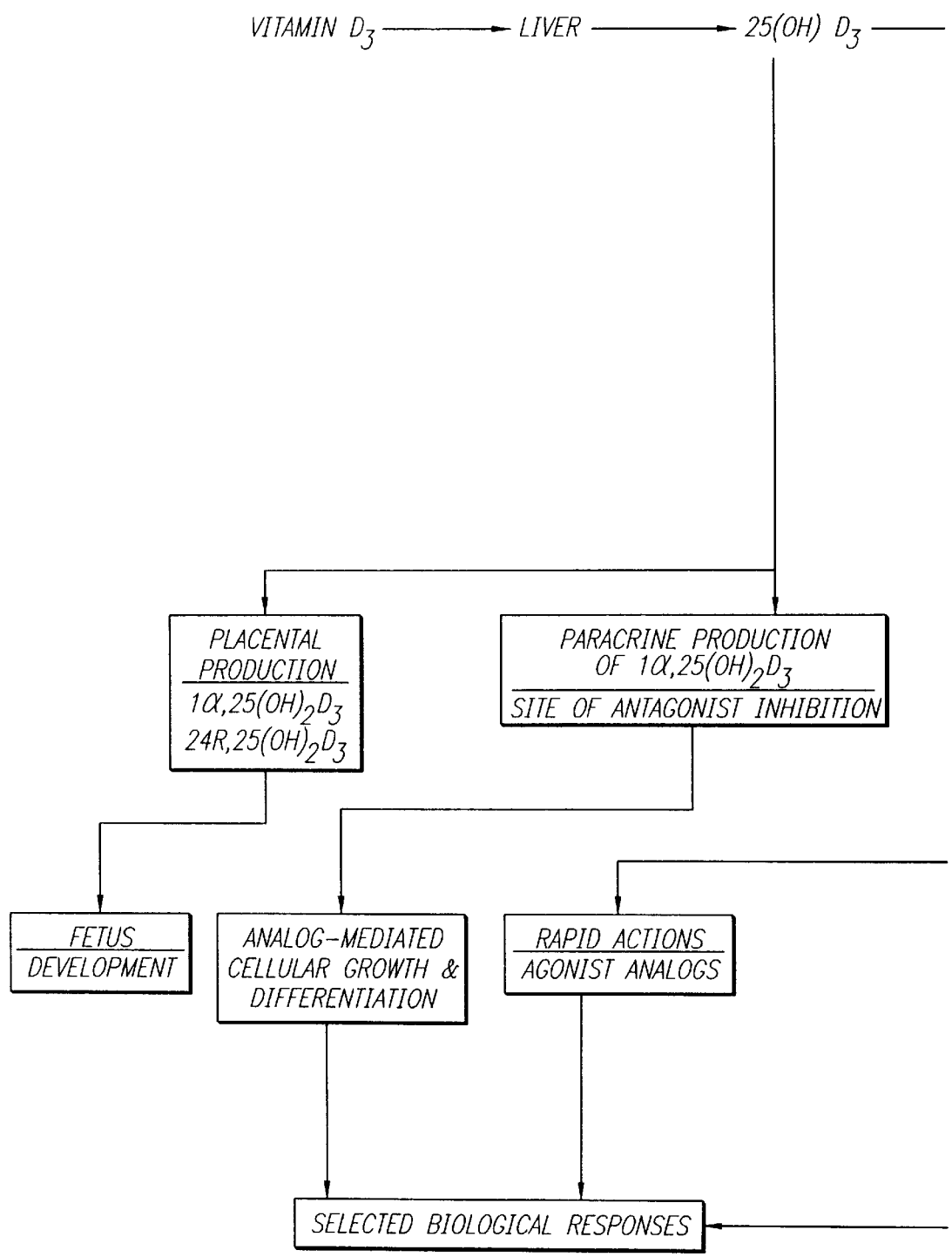
FIG. 1 illustrates a simplified version of the vitamin D endocrine system including the endocrine gland, the kidney which produces the two vitamin D related steroid hormones, and the categories of target organs where biological responses are generated and where vitamin D analogs function.

The scope of the biological responses related to vitamin D is best understood through the concept of the vitamin D endocrine system model as seen in FIG. 1. This model is based on the fact that vitamin D$_3$ is, in reality, a prohormone and is not known to have any intrinsic biological activity itself. It is only after vitamin D$_3$ is metabolized first into 25(OH)D$_3$ in the liver and then into 1α,25(OH)$_2$D$_3$ and 24R,25(OH)$_2$D$_3$ by the kidney, that biologically active molecules are produced. Today some 37 vitamin D$_3$ metabolites have been isolated and chemically characterized. This invention concerns biologically active analogs of 1α,25(OH)$_2$D$_3$.

FIG. 1 shows the vitamin D endocrine system and its core elements.

Figure 4:
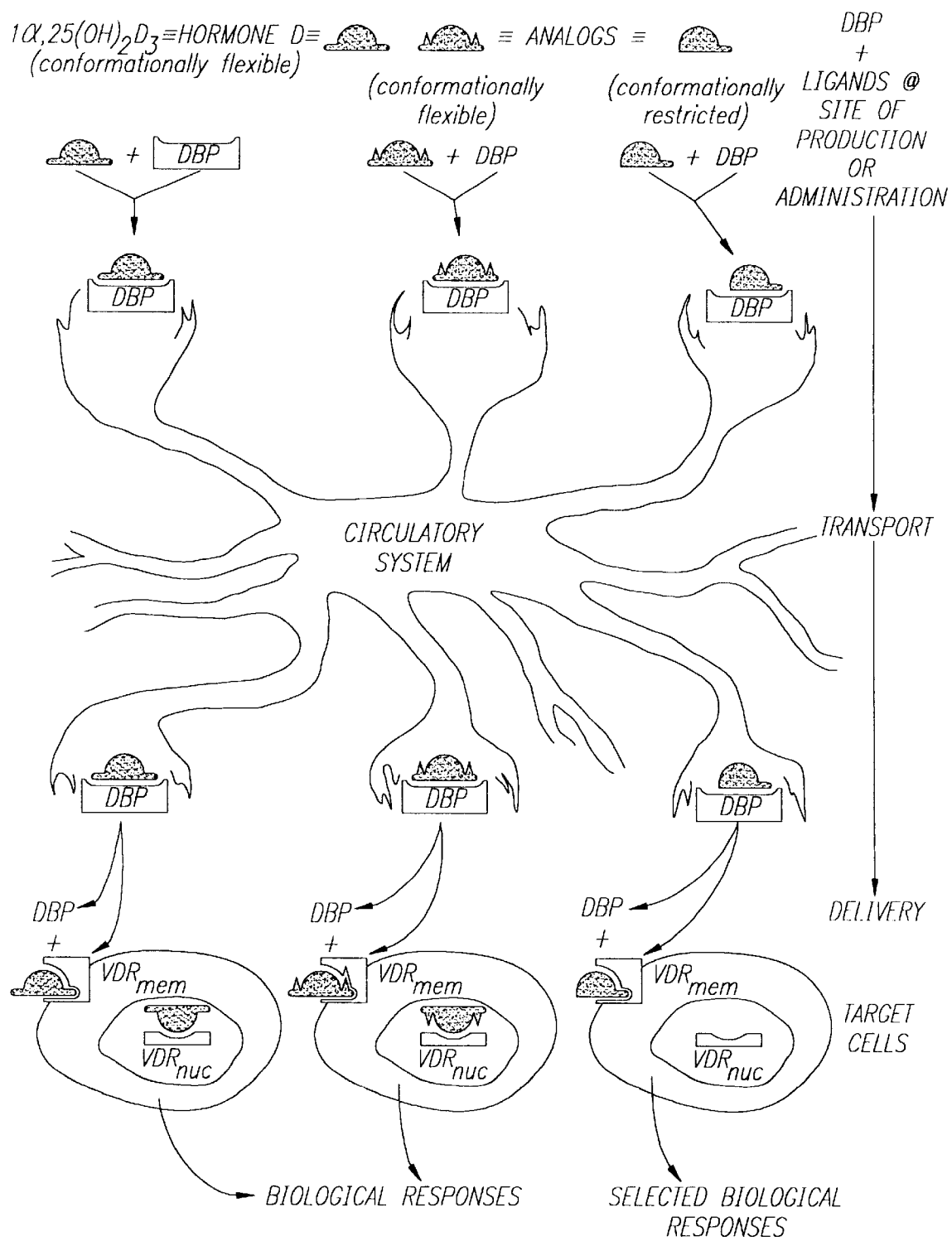
FIG. 4 illustrates the role of the vitamin D-binding protein (DBP) in mediating the delivery of 1α,25(OH)$_2$D$_3$ or analogs to target cells.

The core elements of the vitamin D endocrine system include the skin, liver, kidney, blood circulation and other target organs. As seen in FIG. 1, photoconversion of vitamin D (7-dehydrocholesterol) to vitamin D$_3$ (activated 7-dehydrocholesterol) occurs in the skin. Alternatively, vitamin D$_3$ is supplied by the dietary intake. Vitamin D$_3$ is then metabolized by the liver to 25(OH)D$_3$, the major form of vitamin D circulating in the blood. The kidney, functioning as an endocrine gland, converts 25(OH)D$_3$ to the two principal dihydroxylated metabolites, namely 1α,25(OH)$_2$D$_3$ and 24R,25(OH)$_2$D$_3$. The hydrophobic vitamin D and its metabolites, particularly 1α,25(OH)$_2$D$_3$, are bound to the vitamin D binding protein (DBP) present in the plasma and systemically transported to distal target organs, as seen in FIG. 4. 1α,25(OH)$_2$D$_3$ binding to the target organs cell receptors is followed by the generation of appropriate biological responses through a variety of signal transduction pathways.

Figures 1, 2:
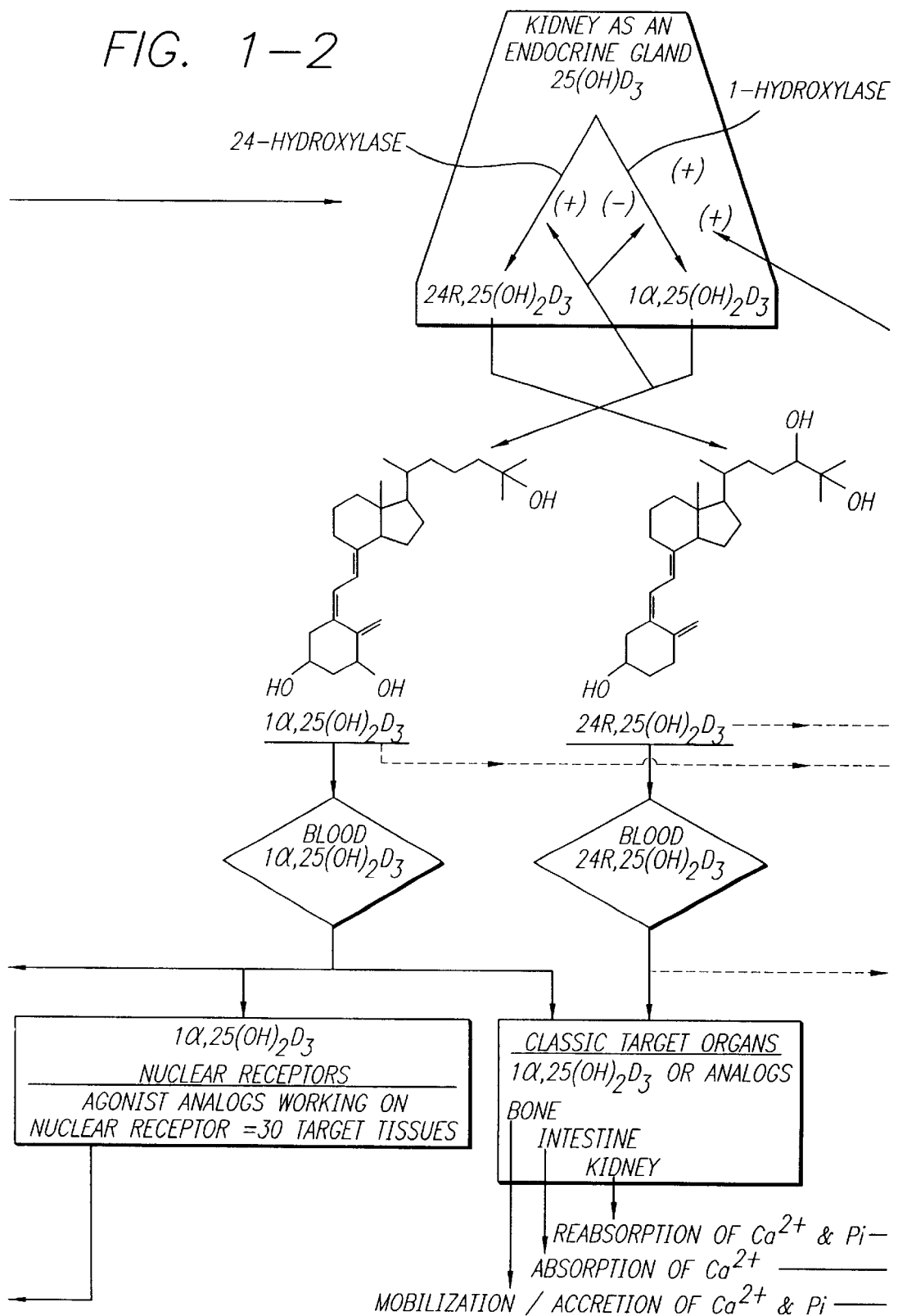
FIG. 2 illustrates both the central role of receptors for 1α,25(OH)$_2$D$_3$ in mediating selective biological and the sites of action of both conformationally flexible and conformationally restricted analogs.

FIG. 2 presents a more comprehensive version of the vitamin D endocrine system specifically indicating selective generation of biological responses by the analogs of 1α,25(OH)$_2$D$_3$ resulting in the treatment of specified disease states. A detailed tabulation of the cells containing the nuclear receptor [VDR$_{nuc}$] for 1α,25(OH)$_2$D$_3$ as well as an enumeration of the tissue location of the membrane receptor [VDR$_{mem}$] where rapid response is initiated are seen in the lower part of the FIG. 2.

FIG. 2 additionally shows the target sites for application of 1α,25(OH)$_2$D$_3$ analogs functioning as agonist and antagonist.

C. Conformational Flexibility of Vitamin D Seco Steroids

Analogs useful for the method of treatment according to the invention are identified, described and their preparation and physical data are disclosed in the applications Ser. No. 08/173,561 filed on Dec. 23, 1993, Ser. No. 08/249,385, filed on May 25, 1994, Ser. No. 08/558,717 filed Nov. 16, 1995, Ser. No. 08/706,356 filed on Aug. 30, 1996 and in concurrently filed application Ser. No. 09/074,565 filed on May 7, 1998, all incorporated herein by reference.

Vitamin D is a seco steroid, thus its 9,10 carbon—carbon bond is broken, and because it has an eight carbon side chain, both the parent vitamin D and all its metabolites and analogs are unusually conformationally flexible. Such conformational flexibility is seen in FIG. 3.

In biological systems, there are a multitude of shapes of 1α,25(OH)$_2$D$_3$ available to interact with receptors to generate biological responses. Different shapes of 1α,25(OH)$_2$D$_3$ are recognized via different ligand binding domains present on the VDR$_{nuc}$, VDR$_{mem}$, and DBP. A variety of analogs of 1α,25(OH)$_2$D$_3$, some of which are as conformationally flexible as 1α,25(OH)$_2$D$_3$ and some of which are conformationally restricted, such as, for example, the family of 6-s-cis locked analogs, were synthesized and tested. The concurrently filed patent application Ser. No. 09/074,565, filed on May 7, 1998, describes the conformationally flexible and conformationally restricted analogs in the vitamin D endocrine system now shown to be suitable to treat selected vitamin D disease states.

Figures 1, 2, 3:
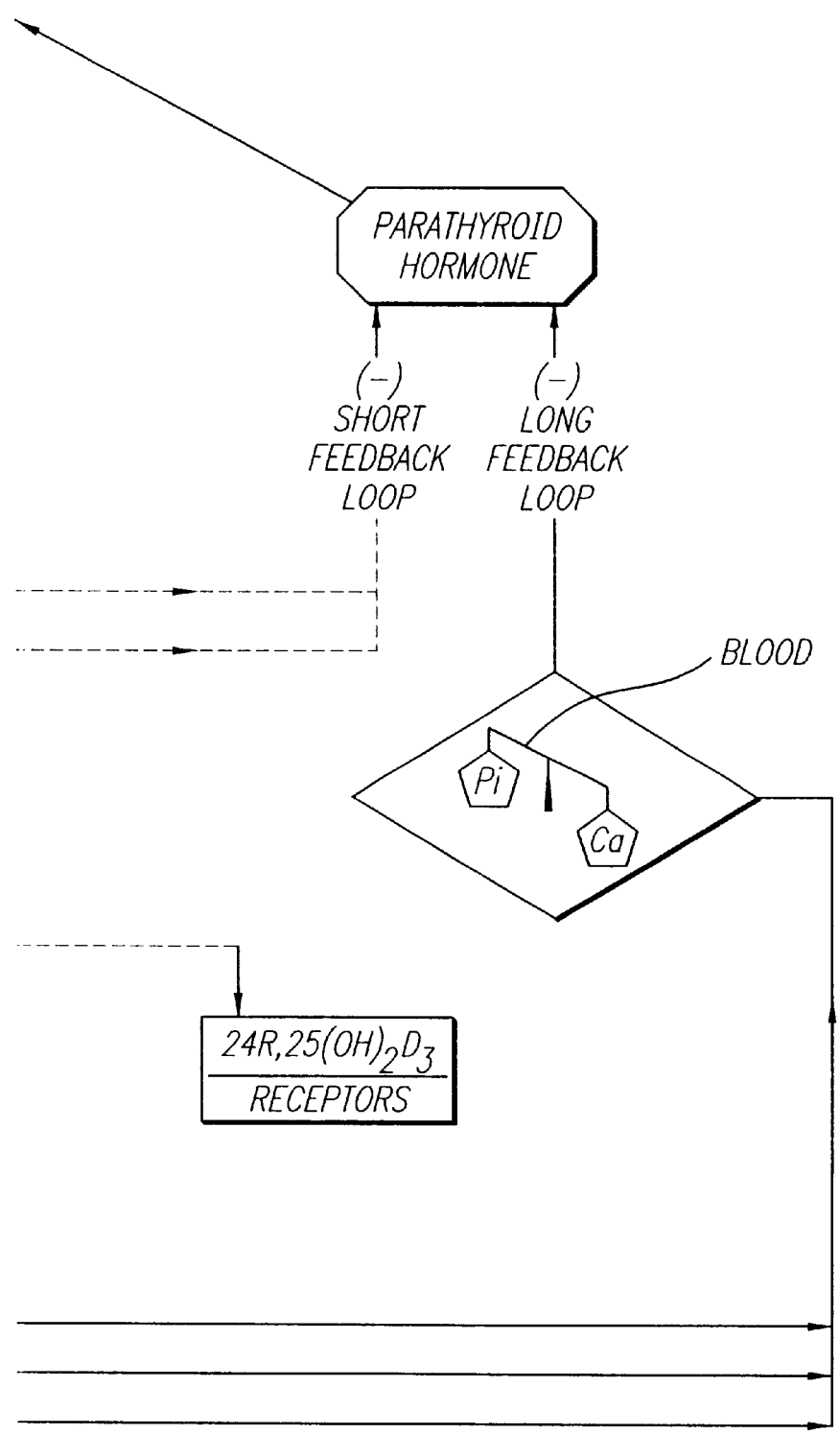
FIG. 3 illustrates the conformational flexibility of vitamin D molecules using 1α,25(OH)$_2$D$_3$ as an example. Top view (FIG. 3A), plane view (FIG. 3B), rotational freedom (FIG. 3C).
Figures 1, 2:
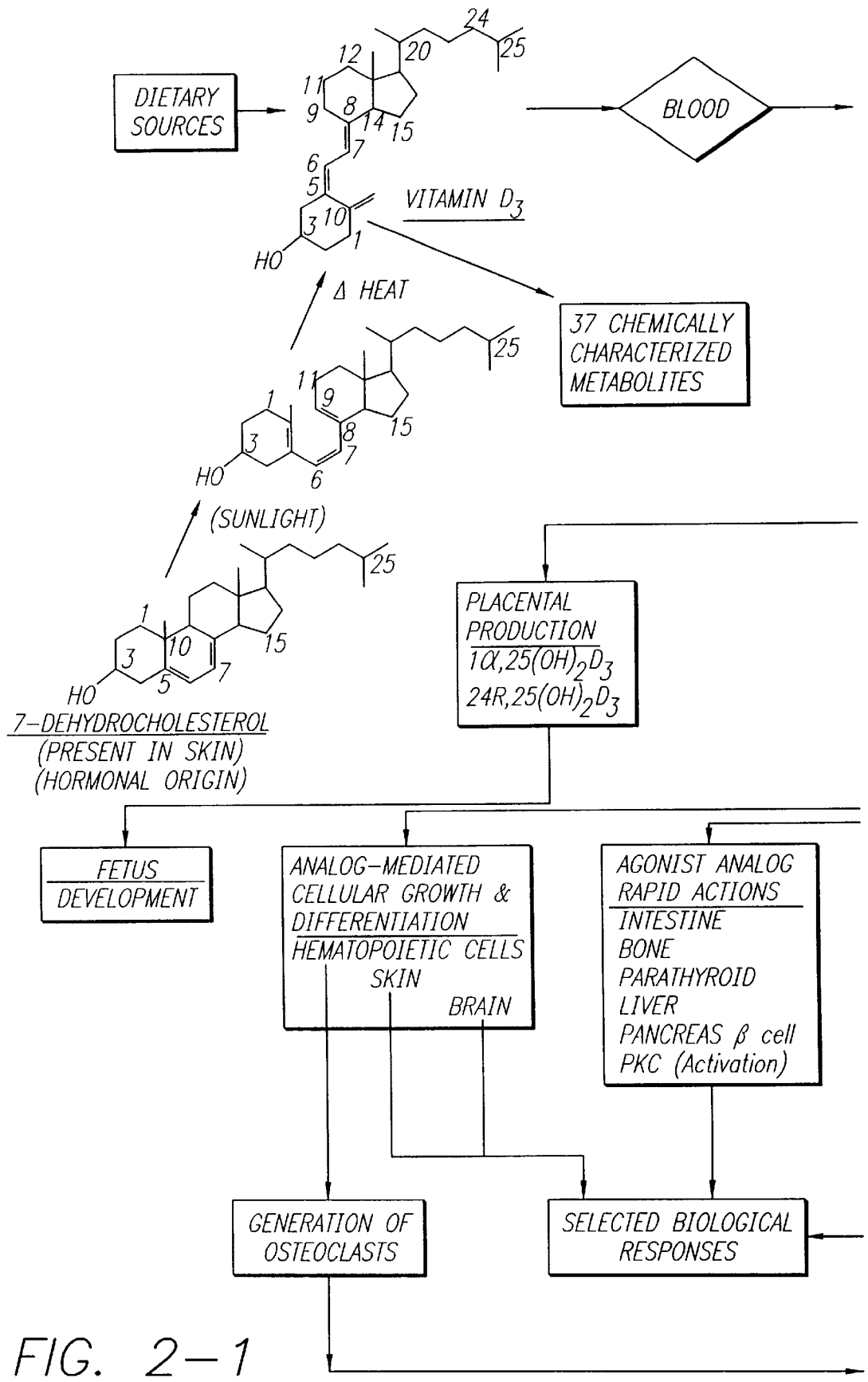
Figure 2:
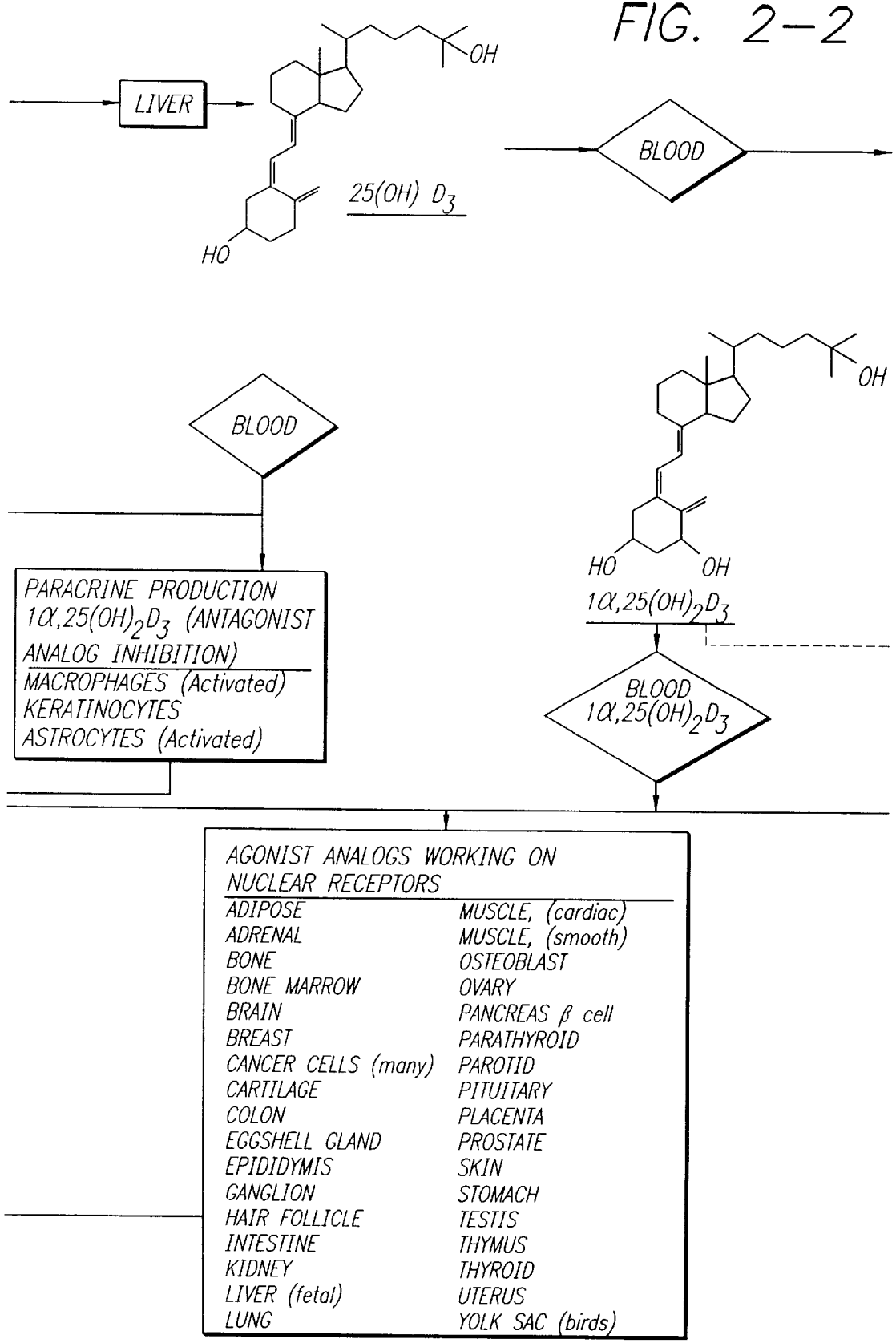
Figures 2, 3:
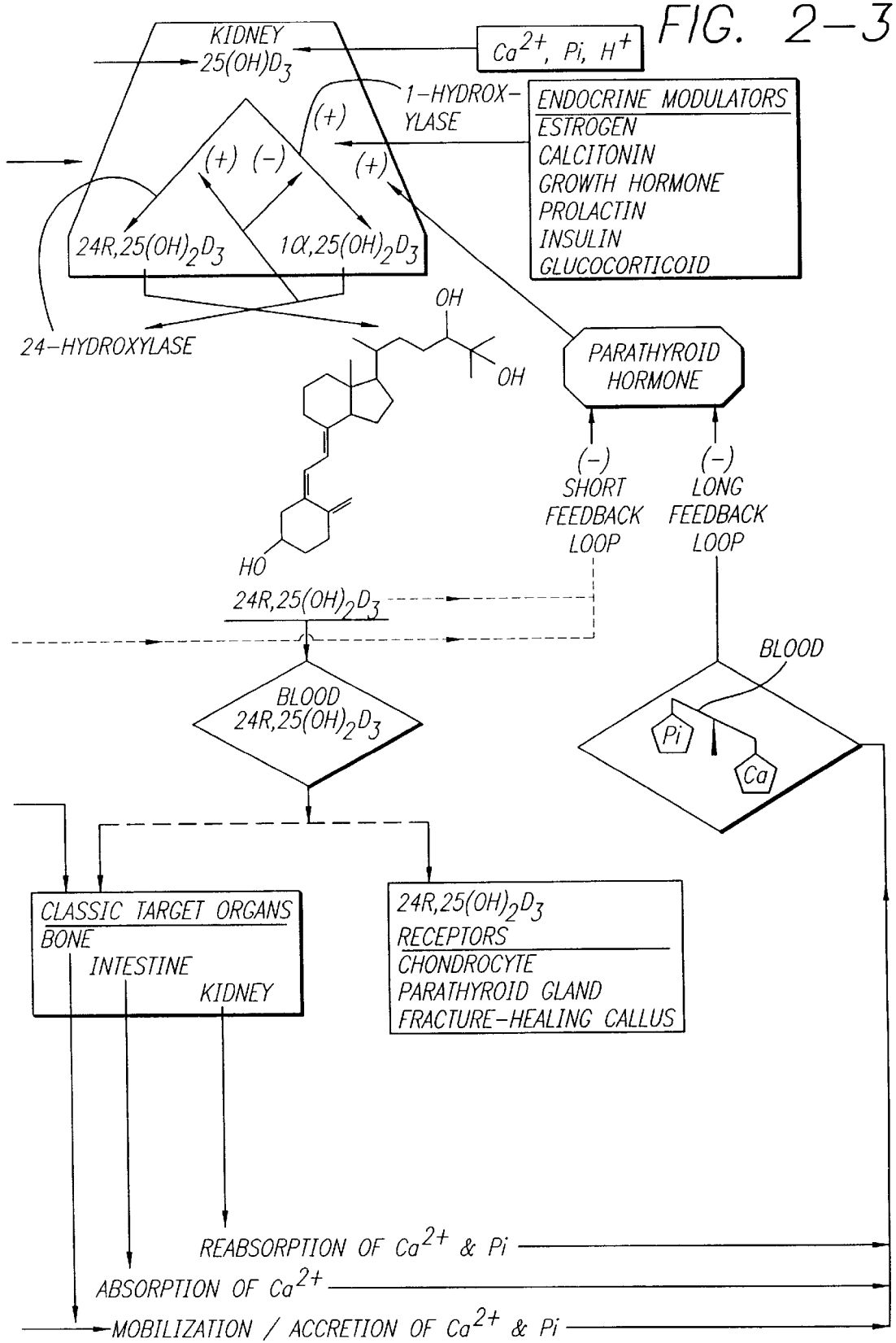

FIG. 3 illustrates the conformational flexibility of vitamin D molecules using 1α,25(OH)$_2$D$_3$ as an example. FIG. 3A shows the dynamic single bond rotation of the cholesterol-like side chain of 1α,25(OH)$_2$D$_3$, that has 360° rotations about five single carbon bonds and the oxygen as indicated by the curved arrows. The dots indicate the position in three-dimensional space of the 25-hydroxyl group for some 394 readily identifiable side chain conformations which have been determined from energy minimization calculations.

Two orientations of the C/D side chain are seen in FIG. 3A, a top view, and in FIG. 3B, an in plane view. FIG. 3B shows the rapid (thousands of times per second) chair-chair interconversion of the A-ring of the secosteroid which effectively equilibrates the 1α-hydroxyl between the axial and equatorial orientations. FIG. 3C shows the 360° rotation rotational freedom about the 6,7 carbon—carbon bond of the seco B-ring which generates conformations ranging from the more steroid-like (6-s-cis) conformation, to the open and extended (6-s-trans) conformation of 1α,25(OH)$_2$D$_3$.

Conformationally flexible analogs of 1α,25(OH)$_2$D$_3$ as seen in FIG. 3, can interact with both the VDR$_{nuc}$ and the VDR$_{mem}$ while 6-s-cis locked conformationally restricted analogs interact only with the VDR$_{mem}$.

A tabulation of the analogs of the invention, their conformational flexibility and general biological properties are presented in Table 1.

FIG. 4 is schematic model of the role of the vitamin D-binding protein (DBP) in transporting 1α,25(OH)$_2$D$_3$ or its analogs throughout the circulatory system.

As seen in FIG. 4, DBP either binds 1α,25(OH)$_2$D$_3$ as it is secreted by the kidney or binds analogs at their site of the encounter following the analog administration. For example, when the analog is administered orally, the DBP binds it after its intestinal absorption. After intravenous administration, DBP binds to the venously administered and available analog in the circulating blood. Without the intervention and transport by DBP, the relatively water insoluble analogs would not find their way in the body to the site of target cells, which are, by definition, any cells in the body that possess either membrane receptors (VDR$_{mem}$) or nuclear receptors (VDR$_{nuc}$) for 1α,25(OH)$_2$D$_3$. The DBP bound to the analog moves through the circulatory system and makes the bound analog universally available throughout the circulatory system to all cells that are subserved.

The DBP has a specific ligand binding domain created via its protein secondary structure. The DBP ligand has a different ligand specificity from that of the VDR$_{nuc}$ and VDR$_{mem}$ receptor ligand binding domains, seen in FIGS. 4 and 5. The analogs are bound noncovalently by the DBP ligand. Accordingly, there is a continual binding and release of 1α,25(OH)$_2$D$_3$ or analogs governed by the equilibrium constant or affinity for ligand binding by DBP. The important consequence is that there are low concentrations of free

TABLE 1

Properties of Analogs of 1α,25(OH)$_2$D$_3$

| Code | Analog Name | Conformation | Genomic Response | Rapid Response | Antagonist |
|---|---|---|---|---|---|
| C | 1α,25(OH)$_2$D$_3$ | Flexible | Yes | Yes | No |
| DE | 22-(m-hydroxyphenyl)1α,25(OH)$_2$D$_3$ | Flexible | Yes | Yes | No |
| DF | 22-(p-hydroxyphenyl)1α,25(OH)$_2$D$_3$ | Flexible | Yes | Yes | No |
| EV | 22-(m-dimethylhydroxymethyl)phenyl-23,24,25,26,27-pentanor-1α(OH)D$_3$ | Flexible | Yes | Yes | No |
| GE | 14-epi-1α,25(OH)$_2$D$_3$ | Flexible | Yes | Yes | No |
| GF | 14-epi-1α,25(OH)$_2$-pre-D$_3$ | Flexible | Yes | Yes | No |
| HH | 1α,25(OH)$_2$-epi-D$_3$ | Flexible | No | No | Yes |
| HJ | 1α,25(OH)$_2$-epi-D$_3$ | Flexible | Yes | Yes | No |
| HL | 1α,25(OH)$_2$D$_3$ | Flexible | No | No | Yes |
| HQ | (22S)-1α,25(OH)$_2$-22,23-diene-D$_3$ | Flexible | Yes | Yes | No |
| HR | (22R)-1α,25(OH)$_2$-22,23-diene-D$_3$ | Flexible | Yes | Yes | No |
| HS | 1α,18,25(OH)$_2$D$_3$ | Flexible | Yes | Yes | No |
| IB | 23-(m-dimethylhydroxymethyl)phenyl-22-yne-24,25,26,27-tetranor-1α(OH)D$_3$ | Flexible | Yes | Yes | No |
| JM | 1α,25(OH)$_2$-7-dehydrocholesterol | 6-s-cis locked | No | Yes | No |
| JN | 1α,25(OH)$_2$-7-lumisterol | 6-s-cis locked | No | Yes | No |
| JO | 1α,25(OH)$_2$-pyrocalciferol | 6-s-cis locked | No | Yes | No |
| JP | 1α,25(OH)$_2$-isopyrocalciferol | 6-s-cis locked | No | Yes | No |
| JR | 1α,25(OH)$_2$-7,8-cis-D$_3$ | Flexible | Yes | Yes | No |
| JS | 1α,25(OH)$_2$-5,6-trans-7,8-cis-D$_3$ | Flexible | Yes | Yes | No |
| JV | (1S,3R,6S)-7,19-retro-1α,25(OH)$_2$D$_3$ | Flexible | Yes | Yes | No |
| JW | (1S,3R,6R)-7,19-retro-1α,25(OH)$_2$D$_3$ | Flexible | Yes | Yes | No |
| JX | 22-(p-hydroxyphenyl)-23,24,25,26,27-pentanor-D$_3$ | Flexible | Yes | Yes | No |
| JY | 22-(m-hydroxyphenyl)-23,24,25,26,27-pentanor-D$_3$ | Flexible | Yes | Yes | No |
| LO | 14α,15α-methano-1α,25(OH)$_2$D$_3$ | Flexible | Yes | Yes | No |

D. Vitamin D-binding Protein

Vitamin D binding protein (DBP) is an important part of the system utilized for the delivery of the vitamin D, its metabolites or its analogs to the target organs. The key role played by its metabolites the DBP in transporting both 1α,25(OH)$_2$D$_3$ and its analogs, both conformationally flexible and conformationally restricted, throughout the physiological system is shown in FIG. 4.

analogs distributed throughout the circulatory system which are available for uptake by target cells and interaction with the VDR$_{nuc}$ and/or VDR$_{mem}$.

As shown in FIG. 4, the DBP has the capability to transport the conformationally flexible 1α,25(OH)$_2$D$_3$, conformationally flexible analogs and 6-s-cis conformationally restricted analogs.

E. Mode-of-Action of $1\alpha,25(OH)_2D_3$ and Its Analogs

The spectrum of biological responses mediated by the hormone $1\alpha,25(OH)_2D_3$ occurs as a consequence of the interaction of $1\alpha,25(OH)_2D_3$ with two classes of specific receptors. These receptors are identified as the nuclear receptor, $VDR_{nuc}$ and the cellular membrane receptor, $VDR_{mem}$.

The $1\alpha,25(OH)_2D_3$ nuclear receptor ($VDR_{nuc}$) from several species has been characterized both biochemically and molecular biologically. The $VDR_{nuc}$ protein was determined to have a molecular weight of about 50 kDa. Through cloning, the $VDR_{nuc}$ was shown to belong to the super family of proteins that includes receptors for all of the classical steroid hormones, such as estradiol, progesterone, testosterone, glucocorticoids, mineralocorticoids, thyroxine and retinoids. The $VDR_{nuc}$ protein contains a ligand binding domain able to bind with high affinity and with great specificity $1\alpha,25(OH)_2D_3$ and closely related analogs.

As seen in FIG. 2 in the box labeled "agonist analogs working on nuclear receptors" the $VDR_{nuc}$ has been shown to be present in about 30 tissues. Over 75 genes controlling various disease states are transcriptionally regulated by $1\alpha,25(OH)_2D_3$ and its analogs. Among others, these genes are calbindin-$D_{28k}$, calbindin-$D_{9k}$, osteocalcin, osteopontin, alkaline phosphatase, 25(OH)D-24-hydroxylase, and carbonic anhydrase which code for proteins of the same name.

Additionally, $1\alpha,25(OH)_2D_3$ has been found to generate biological responses via interaction with a putative membrane receptor [$VDR_{mem}$] which is coupled to cellular signal transduction pathways. This interaction generates rapid response via opening voltage gated $Ca^{2+}$ channels and $Cl^-$ channels as well as activating MAP-kinases. Different shapes of the conformationally flexible $1\alpha,25(OH)_2D_3$ or its analogs bind to the $VDR_{nuc}$ and $VDR_{mem}$ and initiate biological responses via activation of signal transduction mechanisms which are coupled to either the $VDR_{nuc}$ or the $VDR_{mem}$. Thus the totality of biological responses mediated by $1\alpha,25(OH)_2D_3$ or its analogs represents an integration of both nuclear receptor and membrane receptor initiated events.

In terms of analogs of $1\alpha,25(OH)_2D_3$, there are two general classes of such analogs. There are agonists that generate responses similar to $1\alpha,25(OH)_2D_3$ and there are antagonists that block or minimize the responses initiated by $1\alpha,25(OH)_2D_3$ or agonist analogs. Further, agonist or antagonist molecules can either be fully conformationally flexible, like the natural hormone $1\alpha,25(OH)_2D_3$ as seen in FIG. 3, or be conformationally restricted. One example of a conformationally restricted agonist molecule is $1\alpha,25(OH)_2$-7-dehydrocholesterol, analog JM, that is permanently locked in the 6-s-cis shape.

A detailed list of the conformationally flexible and restricted agonist and antagonist analogs is presented in Tables 1–3. Conformationally flexible analogs can interact with both $VDR_{nuc}$ and $VDR_{mem}$. In contrast, 6-s-cis conformationally locked analogs can only interact with $VDR_{mem}$.

The general mode of action by which $1,25(OH)_2D_3$ generates biological responses in target cells is shown in the three panels of FIG. 5. The model seen in FIG. 5 invokes ligand domains for receptors (the $VDR_{nuc}$ and $VDR_{mem}$) with different specificities for different shapes or conformers of $1\alpha,25(OH)_2D_3$. From the point of conformational flexibility, there exists two general classes of analogs. One class are those analogs that have complete flexibility around the 6,7 carbon—carbon bond, as does $1\alpha,25(OH)_2D_3$. The second class are those analogs which are conformationally restricted, such as 6,7-locked analogs. An example of such analogs are $1\alpha,25(OH)_2$-7-dehydrocholesterol (JM) or $1\alpha,25(OH)_2$-lumisterol (JN).

FIG. 5 compares the mode of actions of these two types of analogs, namely conformationally flexible analogs and conformationally restricted 6-s-cis analogs. As seen in FIG. 5A, $1\alpha,25(OH)_2D_3$ which is conformationally flexible interacts with both the membrane receptor depicted as $VDR_{mem}$ located in the cell membrane, and with the cell nuclear receptor depicted as $VDR_{nuc}$ located in the cell nucleus of the target cell. The slow genomic responses appear after $1\alpha,25(OH)_2D_3$ or its analog's interaction with $VDR_{nuc}$. Rapid responses are generated upon interaction of $1\alpha,25(OH)_2D_3$ or its analog with $VDR_{mem}$.

Conformationally flexible analogs of the invention, illustrated in FIG. 5B, act similarly to $1\alpha,25(OH)_2D_3$ generating the same general biological responses as those illustrated in FIG. 5A, i.e., both slow and rapid responses as a consequence of interacting with both $VDR_{nuc}$ and $VDR_{mem}$.

In FIG. 5C, where the action of conformationally restricted 6-s-cis analogs is illustrated, the only interaction which is observed is between the analog and $VDR_{mem}$ receptor thereby resulting solely in selected rapid nongenomic biological responses.

Figure 6:
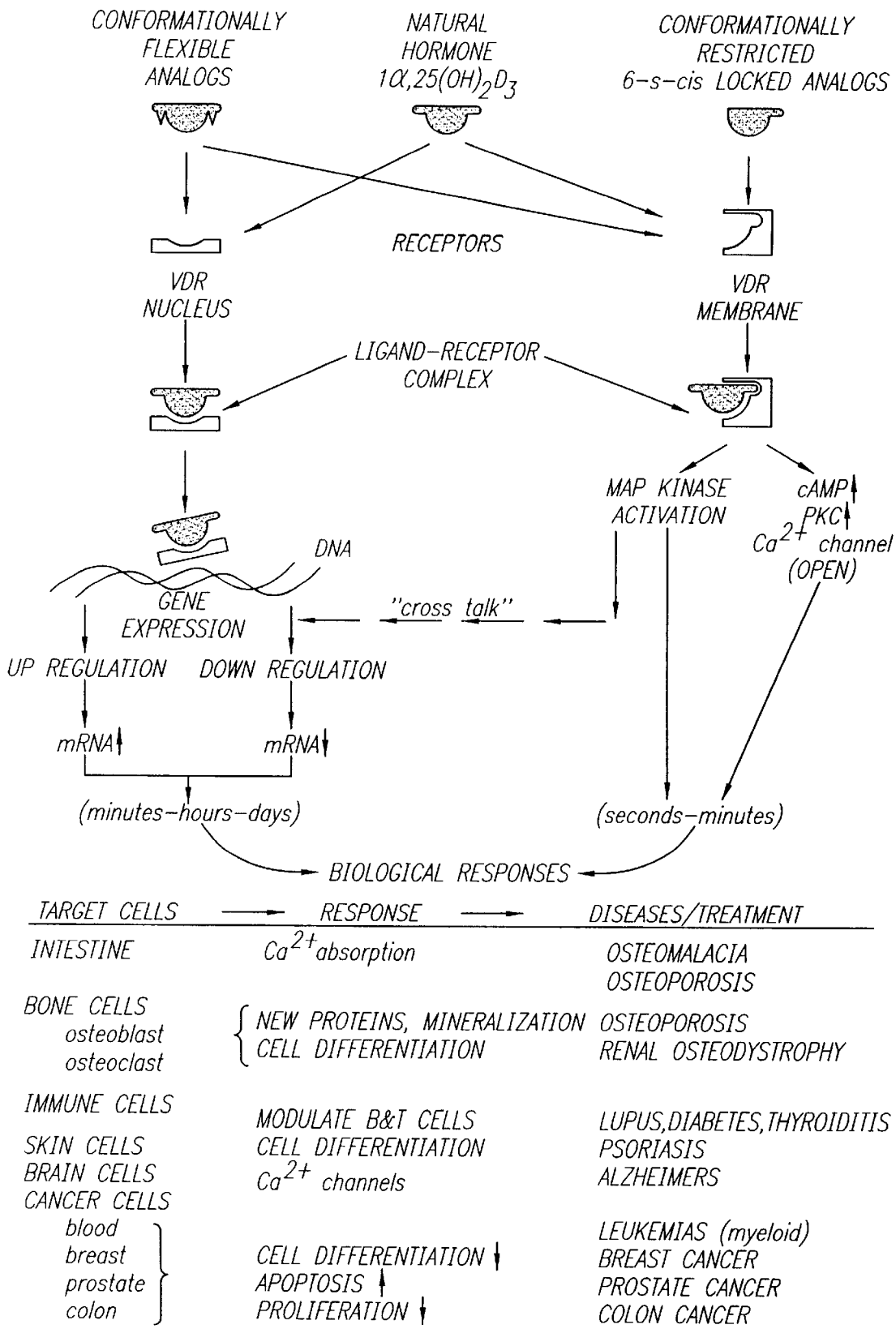
FIG. 6 illustrates mediation of the slow nuclear and rapid biological responses by 1α,25(OH)$_2$D$_3$ and its conformationally flexible and conformationally restricted analogs with a correlation to potential target cells and therapeutical treatment modalities.

FIG. 6 represents a model and a description of the mechanisms of action by which $1\alpha,25(OH)_2D_3$ generates biological responses in target cells. As indicated at the top of FIG. 6, the conformationally flexible natural hormone, $1\alpha,25(OH)_2D_3$, and conformationally flexible analogs interact with both the $VDR_{nuc}$ and $VDR_{mem}$. However, 6-s-cis locked analogs can interact only with the $VDR_{mem}$. After occupancy of the receptors by their ligand, appropriate signal transduction systems are initiated which ultimately lead to the generation of biological responses. The bottom panel of the FIG. 6 lists certain target cells for $1\alpha,25(OH)_2D_3$ and identifies typical responses of these cells to administration of $1\alpha,25(OH)_2D_3$ or the analog which occur there. Disease states for treatment with analogs of $1\alpha,25(OH)_2D_3$ are listed in FIG. 6 bottom.

The right side of FIG. 6 describes the mechanism of action for ligands, both conformationally flexible and 6-s-cis locked analogs, that bind to the $VDR_{mem}$ to initiate the generation of rapid biological responses. Occupancy of the $VDR_{mem}$ can lead to activation of a variety of intracellular messengers, such as cyclic AMP, protein kinase C, or increases in intracellular $Ca^{2+}$ concentration, which, depending upon the cell type, can cause the opening of calcium channels, chloride channels, or activation of mitogen-activated protein kinase.

In cells that have a $VDR_{mem}$ linked to a calcium channel, there is an increase in $Ca^{2+}$ ions moving into the cells that results in an increase in intracellular $Ca^{2+}$ concentrations. In intestinal cells, this will activate the rapid response of transcaltachia and increase the absorption of dietary $Ca^{2+}$ into the body. In bone-forming cells (osteoblasts), opening of the calcium channel followed by the intracellular calcium increase results in increased activities of the osteoblasts on bone formation. similarly, in pancreatic B cells, opening of calcium channels participates favorably in the processes governing the secretion of insulin.

In cells that have a chloride channel linked to a $VDR_{mem}$ there is an increase in chloride ions which is known to be linked to water uptake by the cell leading to a condition of volume expansion. This chloride channel activation in osteoblast cells leads to increased activities in the osteoblast in bone formation. Dysfunction of chloride channel opening in kidney cells has been linked to x-linked hypercalciuric nephrolithiasis.

In cells that have the $VDR_{mem}$ linked to activation of MAP-kinase, so called "message cross-talk" between the rapid response pathway and the nucleus results upon activation of MAP-kinase with analogs of the invention. The cell where $VDR_{mem}$ is activated resulting in rapid responses utilizes cross-talk between the membrane and the $VDR_{nuc}$ receptor leading to modulation of gene transcription, seen in the center of FIG. 5. The MAP-kinase activation leads to changes in the phosphorylation state of the proteins participating in the transcription complex, including the $VDR_{nuc}$. Then, depending upon whether the gene subject to regulation by the $VDR_{nuc}$ is subject to up-regulation or down-regulation, there can be further modulation of this process so that the final outcome of the slow genomic response is favorably enhanced. The details of the enhancement is dependent upon the cell type in which the MAP-kinase was activated. The bottom portion of FIG. 5 links integration of rapid and slow genomic signal transduction processes to the overall outcome biological response for a variety of target cells. In turn, dysfunction of the signal transduction process in the designated target cells can lead to the onset of a variety of disease states as seen in FIG. 5, bottom right column.

II. Therapeutically Active Analogs of $1\alpha,25(OH)_2D_3$

A. Classes of Analogs

1. Agonists (a) Conformationally Flexible Genomic Agonist Analogs

Conformationally flexible genomic agonist analogs are the analogs which interact with the nuclear receptor for $1\alpha,25(OH)_2D_3$ $VDR_{nuc}$ and are, therefore, involved in the slow genomic responses. Exemplary analogs in this group are analogs listed in Table 2. A two-letter code name for analog chemical identification is designated followed by the chemical name.

TABLE 2

| | |
|---|---|
| DE | 22-(m-hydroxyphenyl)-23,24,25,26,27-pentanor-1α(OH)D₃ |
| DF | 22-(p-hydroxyphenyl)-23,24,25,26,27-pentanor -1α(OH)D₃ |
| EV | 22-(m-(dimethylhydroxymethyl)phenyl)-23,24,25,26,27-pentanor-1α(OH)D₃ |
| GE | 14-epi-1α,25(OH)₂D₃ |
| GF | 14-epi-1α,25(OH)₂-pre-D₃ |
| HJ | 1α,25(OH)₂-3-epi-D₃ |
| HQ | (22S)-1α,25(OH)₂-22,23-diene-D₃ |
| HR | (22R)-1α,25(OH)₂-22,23-diene-D₃ |
| HS | 1α,18,25(OH)₃D₃ |
| IB | 23-(m-(Dimethylhydroxymethyl)phenyl)-22-yne-24,25,26,27-tetranor-1α(OH)D₃ |
| JR | 1α,25(OH)₂-7,8-cis-D₃ |
| JS | 1α,25(OH)₂-5,6-trans-7,8-cis-D₃ |
| JV | (1S,3R,6S)-7,19-retro-1α,25(OH)₂D₃ |
| JW | (1S,3R,6R)-7,19-retro-1α,25(OH)₂D₃ |
| JX | 22-(p-hydroxyphenyl)-22,23,24,25,26,27-pentanor-D₃ |
| JY | 22-(m-hydroxyphenyl)-23,24,25,26,27-pentanor-D₃ |
| LO | 14α,15α-methano-1α,25(OH)₂D₃ |

(b) Conformationally Restricted Genomic Agonist Analogs

Conformationally restricted genomic agonist analogs are the analogs which bind with a specificity to the vitamin D nuclear receptor $VDR_{nuc}$ and are therefore also involved in genomic responses.

(c) Conformationally Flexible Nongenomic Agonist Analogs Generating Rapid Response Conformationally flexible agonist analogs of $1\alpha,25(OH)_2D_3$ which stimulate rapid nongenomic responses via interaction with the vitamin D membrane receptor $VDR_{mem}$ are listed in Table 3. A two-letter code name for the analog chemical identification is esignated followed by the chemical name.

TABLE 3

| | |
|---|---|
| DE | 22-(m-hydroxyphenyl)- 23,24,25,26,27-pentanor-1α(OH)D₃ |
| DF | 22-(p-hydroxyphenyl)- 23,24,25,26,27-pentanor -1α(OH)D₃ |
| EV | 22-(m-(dimethylhydroxymethyl)phenyl)-23,24,25,26,27-pentanor-1α(OH)D₃ |
| GE | 14-epi-1α,25(OH)₂D₃ |
| GF | 14-epi-1α,25(OH)₂-pre-D₃ |
| HJ | 1α,25(OH)₂-3-epi-D₃ |
| HQ | (22S)-1α,25(OH)₂-22,23-diene-D₃ |
| HR | (22R)-1α,25(OH)₂-22,23-diene-D₃ |
| HS | 1α,18,25(OH)₃D₃ |
| IB | 23-(m-(dimethylhydroxymethyl)phenyl)-22-yne-24,25,26,27-tetranor-1α(OH)D₃ |
| JR | 1α,25(OH)₂-7,8-cis-D₃ |
| JS | 1α,25(OH)₂-5,6-trans-7,8-cis-D₃ |
| JV | (1S,3R,6S)-7,19-retro-1α,25(OH)₂D₃ |
| JW | (1S,3R,6R)-7,19-retro-1α,25(OH)₂D₃ |
| JX | 22-(p-hydroxyphenyl)-22,23,24,25,26,27-pentanor-D₃ |
| JY | 22-(m-hydroxyphenyl)-23,24,25,26,27-pentanor-D₃ |
| LO | 14α,15α-methano-1α,25(OH)₂D₃ |

(d) Conformationally Restricted Nongenomic Agonist Analogs Generating Rapid Responses Conformationally restricted agonist analogs which generate nongenomic rapid responses via interaction with the membrane receptor for $1\alpha,25(OH)_2D_3$ are listed in Table 4. A two-letter code name for analog chemical identification is designated followed by the chemical name.

TABLE 4

| | |
|---|---|
| JM | 1α,25(OH)₂-7-dehydrocholesterol |
| JN | 1α,25(OH)₂-lumisterol₃ |
| JO | 1α,25(OH)₂-pyrocalciferol₃ |
| JP | 1α,25(OH)₂-isopyrocalciferol₃ |

2. Antagonists (a) Conformationally Flexible Antagonists of Rapid Responses

Conformationally flexible antagonist of genomic responses function as antagonists of the vitamin D nuclear receptor.

(b) Conformationally Restricted Antagonists of Rapid Responses

Conformationally restricted analogs which function as antagonists of nongenomic rapid responses via interaction with the membrane receptor for $1\alpha,25(OH)_2D_3$ are listed in Table 5. A two letter code name for analog identification is designated followed by the chemical name.

TABLE 5

| | |
|---|---|
| HH | 1β,25(OH)₂-3-epi-D₃ |
| HL | 1β,25(OH)₂D₃ |

(c) Conformationally Restricted Antagonists of Rapid Responses

Conformationally restricted antagonists of rapid responses function as antagonists of the $VDR_{mem}$.

III. Biological Profile of $1\alpha,25(OH)_2D_3$ Analogs

A. Analog Binding to the Vitamin D-Binding Protein

Analog utility and its activity is dependent on its binding to the vitamin D-binding protein (DBP). Only if the analog is able to bind to the DBP can it be delivered to the target organ. It is therefore, important to determine the degree of binding of each analog to the DBP.

Analog binding to the DBP is illustrated in FIG. 4 which summarizes the key role played by the vitamin D binding protein in the transport of $1\alpha,25(OH)_2D_3$ or its analogs through the blood compartment, from its site of administration or uptake to make them available for uptake by target cells.

The vitamin D-binding protein (DBP) is a protein of about 50 kDa containing a ligand binding domain which can recognize and discriminate various functional groups and structural modifications on potential ligands, i.e. analogs of $1\alpha,25(OH)_2D_3$. Since DBP determines the availability of its bound ligand to target cells, it is important to define the relative affinity of a given analog to bind to DBP. The affinity of binding of the analog to the DBP binding site is measured and expressed as Relative Competitive Index.

The more available a ligand is for uptake by a target cell, the more likely it is to interact with either the $VDR_{nuc}$ or the $VDR_{mem}$ so as to generate biological responses.

Figure 7:
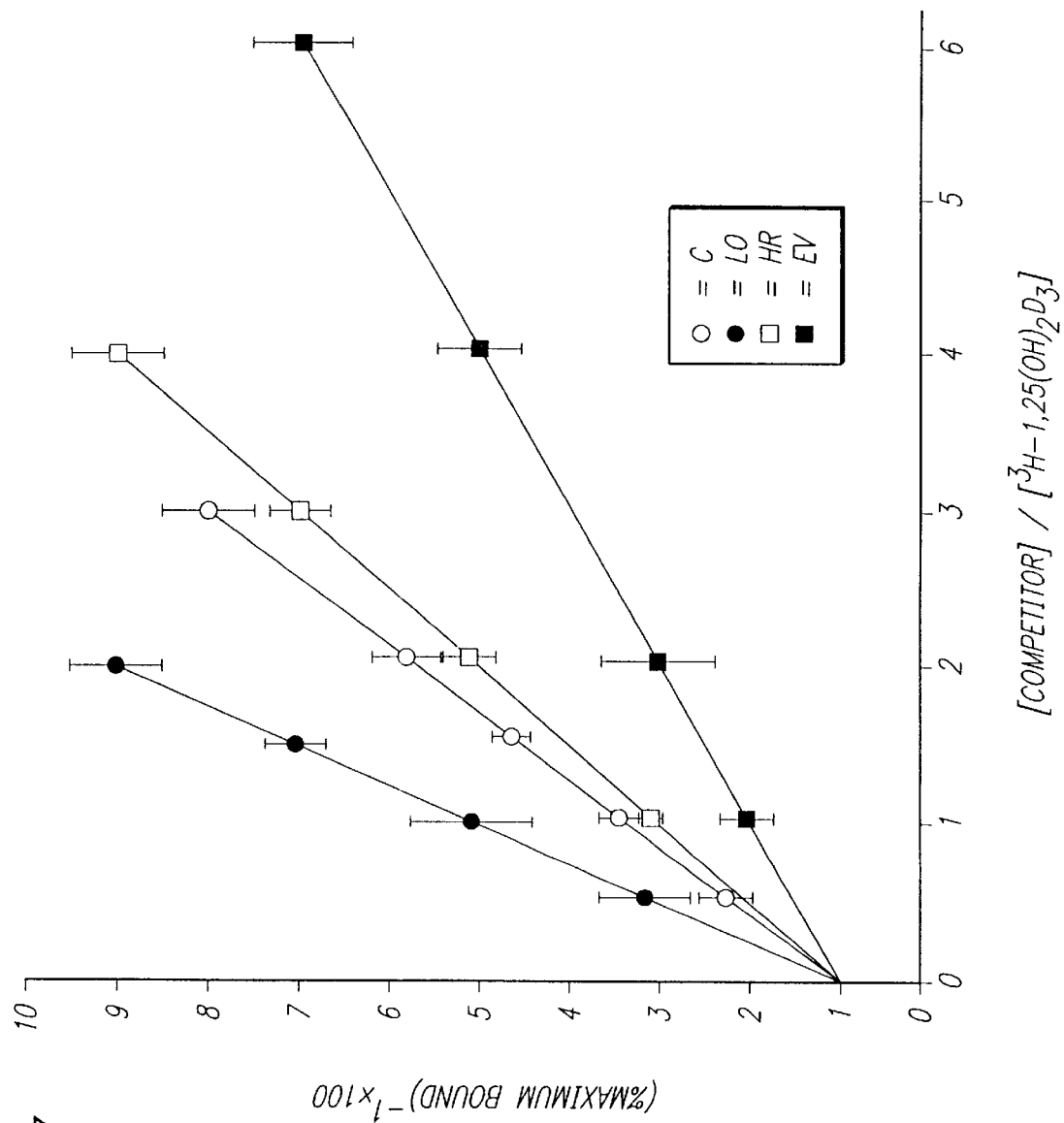
FIG. 7 presents results of the binding of 1α,25(OH)$_2$D$_3$ and selected analogs to the vitamin D-binding protein.

The Relative Competitive Index (RCI) of several analogs of the invention is seen in FIG. 7.

FIG. 7 shows results of the determination of the RCI for representative analogs for the vitamin D binding protein (DBP) compared to $1\alpha,25(OH)_2D_3$, identified as compound C. The compared analogs are $14\alpha,15\alpha$-methano-$1\alpha,25(OH)_2D_3$ (LO), 22(m(dimethylhydroxymethyl)phenyl)-23,24,25,26,27-pentanor-$1\alpha$-OH-$D_3$ (EV) and (22R)-1,25(OH)$_2$-22,23,diene-$D_3$ (HR), all conformationally flexible genomic agonists. The RCI values expressed as (% maximum bound)$^{-1}\times 100$ of the analog in competition with 1,25(OH)$_2D_3$ are indicated in the FIG. 7. By definition the RCI for $1\alpha,25(OH)_2D_3$ is set to 100%. The data seen in FIG. 7 represent the mean of three determinations.

The results seen in FIG. 7 indicate that compared to 100% binding of $1\alpha,25(OH)_2D_3$ (C) to the DBP, analog LO binds to DBP 60% as tightly while analogs EV and HR bind only 25% and 48% as tightly to DBP. From the perspective of DBP functioning in vivo or in being present in the culture media used to nourish cells grown in tissue culture, analogs which have an RCI lower than $1\alpha,25(OH)_2D_3$ have a higher free concentration in solution and are more available for uptake into target cells. Conversely, analogs with an RCI for DBP greater than 100% ($1\alpha,25(OH)_2D_3$), have a lower free concentration and are less available for uptake into potential target cells.

In terms of analogs relevant to this patent application as listed in Table 6, below, analog JX has the highest RCI for DBP, a value of 211,000 or 2110 times greater than the reference $1\alpha,25(OH)_2D_3$. This analog, therefore, binds very tightly to DBP and has a much lower free concentration and lower availability for uptake by target cells. Conversely analog HL has an RCI of only 0.1, which is 1000 times lower than that of the reference $1\alpha,25(OH)_2D_3$. Thus, this analog binds poorly to DBP and has a much higher free concentration and, therefore, a higher availability for uptake by target cells if brought to their vicinity.

B. Biological Evaluation of 1,25(OH)$_2D_3$ Analogs

Table 6 summarizes the biological evaluation of all the analogs of $1\alpha,25(OH)_2D_3$ which are subject of this invention.

Table 6 identifies biological properties, such as genomic response, rapid response, agonist or antagonist function, binding of the analog to the vitamin binding protein (expressed as RCI), binding to the nuclear $1\alpha,25(OH)_2D_3$ receptor (expressed as RCI) rapid response (expressed as % transcaltachia the rapid hormonal stimulation of intestinal calcium absorption) the classic vitamin D responses such as intestinal $Ca^{2+}$ absorption (ICA) and bone $Ca^{2+}$ mobilizing activity (BCM) determined in vivo in a vitamin D-deficient chick, and cell differentiation (expressed as % ED50), an assessment of the ability to promote the nuclear response of cell differentiation.

As seen in Table 6, twenty three analogs and $1\alpha,25(OH)_2D_3$ (designated by analog code as C) were submitted to testing as outlined in Table 6. Of these analogs 22 are agonists, that is compounds which possess affinity for the receptor and are capable of combining with $1\alpha,25(OH)_2D_3$ receptor. One of the analogs is an antagonist (HL), that is a compound which does not bind to the receptor and in fact it blocks or inhibits the action of agonist for rapid responses.

Nineteen of the analogs are able to elicit both the genomic and rapid responses.

Four of the analogs (JM, JN, JO and JP) are able to elicit solely rapid responses, that is to bind only to the membrane $VDR_{mem}$ receptors. The three of four analogs identified as eliciting the rapid responses show transcaltachia activity corresponding to about 50 to 60% of the $1\alpha,25(OH)_2D_3$ transcaltachia activity. Analog JN shows 105% of binding to $VDR_{mem}$ receptor, that is, it has binding affinity higher than $1\alpha,25(OH)_2D_3$.

Thirteen analogs (EV, GE, GF, HQ, HR, JM, JN, JO, JP, JR, JS, JV and LO) have DBP binding activity lower than $1\alpha,25(OH)_2D_3$. Consequently, these analogs are more available in their free form in the circulating blood and are therefore more available for uptake by the target cell and more active in treatment of vitamin D diseases than $1\alpha,25(OH)_2D_3$.

Regarding binding to the nuclear receptor to elicit genomic responses, all tested analogs have lower binding affinity for $1\alpha,25$-D receptor than $1\alpha,25(OH)_2D_3$. Only the analog LO shows similar binding activity (98%) to that of $1\alpha,25(OH)_2D_3$, followed by the analogs EV (62%), HR (52%), DE (29%), HS (25%), HJ (24%) and GE (15%). These analogs are therefore suitable for treatment of diseases where the slower genomic responses via gene expression are involved. For elicitation of classic vitamin D responses ICA and BCM, the best analog identified by its comparative activity with $1\alpha,25(OH)_2D_3$ is the analog LO, showing 30% of ICA and 50% of BCM, compared to 1,25(OH)$_2D_3$.

All analogs disclosed herein having either genomic or rapid response or both are useful and suitable for treatment of diseases treatable with $1\alpha,25(OH)_2D_3$.

TABLE 6

| Analog Code | Analog Name | Biological Properties | | | Vit D Binding Protein (RCI) | Nuclear $1\alpha,25$-D Receptor (RCI) | Rapid Trans- Caltachia (%) | Classic Vit D Responses | | Cell Different ED-50 |
|---|---|---|---|---|---|---|---|---|---|---|
| | | Genomic | Rapid Response | Antagonist | | | | ICA (%) | BCM (%) | |
| C | $1\alpha,25(OH)_2D_3$ | Yes | Yes | No | 100 | 100 | 100 | 100 | 100 | 1.00 |
| DE | 22-(m-hydroxyphenyl) 23,24,25,26,27-pentanor-$1\alpha(OH)D_3$ | Yes | Yes | No | 980 | 29 | | 0.3 | 1.0 | |
| DF | 22-(p-hydroxyphenyl) 23,24,25,26,27-pentanor-$1\alpha(OH)D_3$ | Yes | Yes | No | 1980 | 5 | | 0.04 | 0.08 | |

TABLE 6-continued

| | | Biological Properties | | | Vit D Binding | Nuclear 1α,25-D | Rapid Trans- | Classic Vit D Responses | | Cell |
|---|---|---|---|---|---|---|---|---|---|---|
| Analog Code | Analog Name | Genomic | Rapid Response | Antagonist | Protein (RCI) | Receptor (RCI) | Caltachin (%) | ICA (%) | BCM (%) | Different ED-50 |
| EV | 22-(m-dimethylhydroxymethyl)phenyl-23,24,25,26,27-pentanor-1α(OH)D$_3$ | Yes | Yes | No | 25 | 62 | | 30 | 8 | |
| GE | 14,epi-1α,25(OH)$_2$D$_3$ | Yes | Yes | No | 12 | 15 | | 0.5 | <0.1 | |
| GF | 14,epi-1α,25(OH)$_2$-pre-D$_3$ | Yes | Yes | No | 2 | 2 | | 1.5 | <0.1 | |
| HH | 1β,25(OH)$_2$-epi-D$_3$ | No | No | Yes | 6570 | 0.2 | | | | |
| HJ | 1α,25(OH)$_2$-epi-D$_3$ | Yes | Yes | No | 800 | 24 | | 2.8 | 1.5 | |
| HL | 1β,25(OH)$_2$D$_3$ | No | No | Yes | 450 | 0.1 | 0 | <0.1 | <0.3 | |
| HQ | (22S)-1α,25(OH)$_2$-22,23-diene-D$_3$ | Yes | Yes | No | 11 | 21 | | 2.5 | 1.0 | |
| HR | (22R)-1α,25(OH)$_2$-22,23-diene-D$_3$ | Yes | Yes | No | 48 | 52 | | 12 | 0.6 | |
| HS | 1α,18,25(OH)$_3$D$_3$ | Yes | Yes | No | | 25 | | NA | NA | 0.05 |
| IB | 23-(m-dimethylhydroxymethyl)phenyl-22-yne-23,24,25,26,27-tetranor-1α(OH)D$_3$ | Yes | Yes | No | | 1 | | NA | NA | |
| JM | 1α,25(OH)$_2$-7-dehydrocholesterol | No | Yes | No | −0.3 | 0.1 | 60 | 1.8 | 0.8 | |
| JN | 1α,25(OH)$_2$-7-lumisterol | No | Yes | No | −0.7 | 1.8 | 105 | 2.1 | 1.0 | |
| JO | 1α,25(OH)$_2$-pyrocalciferol | No | Yes | No | 2.0 | 0.2 | 50 | 0.6 | 0.03 | |
| JP | 1α,25(OH)$_2$-isopyrocalciferol | No | Yes | No | −5.0 | 0.3 | 60 | 0.5 | 0.8 | |
| JR | 1α,25(OH)$_2$-7,8-cis-D$_3$ | Yes | Yes | No | 8 | 0.8 | | 0.03 | 0.02 | |
| JS | 1α,25(OH)$_2$-5,6-trans-7,8-cis-D$_3$ | Yes | Yes | No | 12 | 1.6 | | <0.02 | <0.02 | |
| JV | (1S,3R,6S)-7,19-retro-1α,25(OH)$_2$D$_3$ | Yes | Yes | No | 37 | 1.6 | | 0.02 | 0.02 | |
| JW | (1S,3R,6R)-7,19-retro-1α,25(OH)$_2$D$_3$ | Yes | Yes | No | 700 | 2.6 | | 0.05 | 0.3 | |
| JX | 22-(m-hydroxyphenyl)-23,24,25,26,27-pentanor-D$_3$ | Yes | Yes | No | 211,000 | 0.002 | | <0.05 | <0.05 | |
| JY | 22-(m-hydroxyphenyl)-23,24,25,26,27-pentanor-D$_3$ | Yes | Yes | No | 132,000 | 0.001 | | <0.05 | <0.05 | |
| LO | 14α,15α-methano-1α,25(OH)$_2$D$_3$ | Yes | Yes | No | 60 | 98 | | 30 | 80 | |

IV. Genomic Responses

A. Interaction of Analogs with Receptors

A mode-of-action and interaction of 1α,25(OH)$_2$D$_3$ and the analogs of the invention with the VDR$_{nuc}$ and VDR$_{mem}$ to generate various biological responses is outlined in FIGS. 5 and 6.

After transport and delivery of 1α,25(OH)$_2$D$_3$, or the analog of the invention by DBP through the circulatory system, the 1α,25(OH)$_2$D$_3$, or the analog is disassociated from the DBP. The 1α,25(OH)$_2$D$_3$, or the analog, then diffuses as free molecule through the extracellular fluid to come into very close proximity of a target cell. The target cell, by definition, is a cell possessing either or both the VDR$_{nuc}$ and VDR$_{mem}$. As shown in FIG. 5, panel A, the conformationally flexible 1α,25(OH)$_2$D$_3$, or the analog, then interacts either directly with the VDR$_{mem}$ present on the outer cell membrane or, alternatively, diffuses through the outer cell membrane and enters into the cytosol or soluble portion of the cell where it encounters and interacts with the VDR$_{nuc}$.

Because of the high affinity of the VDR$_{nuc}$ for conformationally flexible analogs of 1α,25(OH)$_2$D$_3$, a very tight receptor ligand complex is formed virtually exclusively in the nuclear portion of the cell. Resident in the nucleus of the cell is the DNA that comprise all the genes that describe the blueprints for that given organism (see FIG. 6, left side). The genetic information inherent in the DNA of the given gene is utilized via initiation of a complex process known as transcription and translation. The transcription process involves conversion of the information resident in the sequence of nucleotides comprising the DNA into messenger RNA molecules. The process of translation then describes the biological processes wherein the mRNA molecules are translated by the process of protein biosynthesis to result in the production of protein molecules. There is the general relationship between one gene, one mRNA molecule, and one specific protein. The specific protein then is involved in a critical way in elicitation of the biological responses which are governed by the initiator of its biosynthesis, in this example, the VDR$_{nuc}$ forming a complex with its hormone or analog ligand.

Thus, the occupied VDR$_{nuc}$ will search out amongst all the DNA resident in the nucleus, those genes which have incorporated into them the so-called vitamin D response element (VDRE). When a VDR$_{nuc}$ finds a specific gene with a VDRE, then there ensues the formation of an active transcription complex.

The transcription complex is comprised of the DNA of a specific gene that contains a VDRE and, as well, other protein enzymes that are necessary to convert the blueprint information of the DNA into the generation of new messenger RNA molecules. There are two general categories of VDRE. One category comprises those that result in stimulation of the transcription process, that is an increase in the number of mRNA molecules that are produced. Another category comprises those which repress, that is reduce the number of mRNA molecules that are produced. Thus, the specific presence of a conformationally flexible 1α,25(OH)$_2$D$_3$ (FIG. 5A) or analog (drug) (FIG. 5B) in the target cell where there is a VDR$_{nuc}$ results in a change, either an increase or a decrease, in the production of specific messenger RNA molecules linked ultimately to the production of a specific biological response, as illustrated in FIG. 6, left side.

The critical contribution of the conformationally flexible 1α,25(OH)$_2$D$_3$ or analog (drug), is to regulate the gene transcription process. The resulting pool of messenger RNA molecules is then translated resulting in either increased or decreased amounts of specific new proteins. These new proteins then engage in their regular function that varies depending upon the nature of the specific gene from which it was transcribed.

Genes that are turned-on by VDR$_{nuc}$/analog complex result in generation of specific proteins depending on the target tissue.

B. VDR$_{nuc}$ Relative Competitive Index As Assay

The ability of analogs to mediate genomic responses are directly determined by the ability of the analog in question to bind to the nuclear receptor for 1α,25(OH)$_2$D$_3$ [VDR$_{nuc}$]. This ability is detected by the assay measuring Relative Competitive Index (RCI). Exemplary illustration of the RCI assay and results of RCI is seen in FIG. 8.

Figure 8:
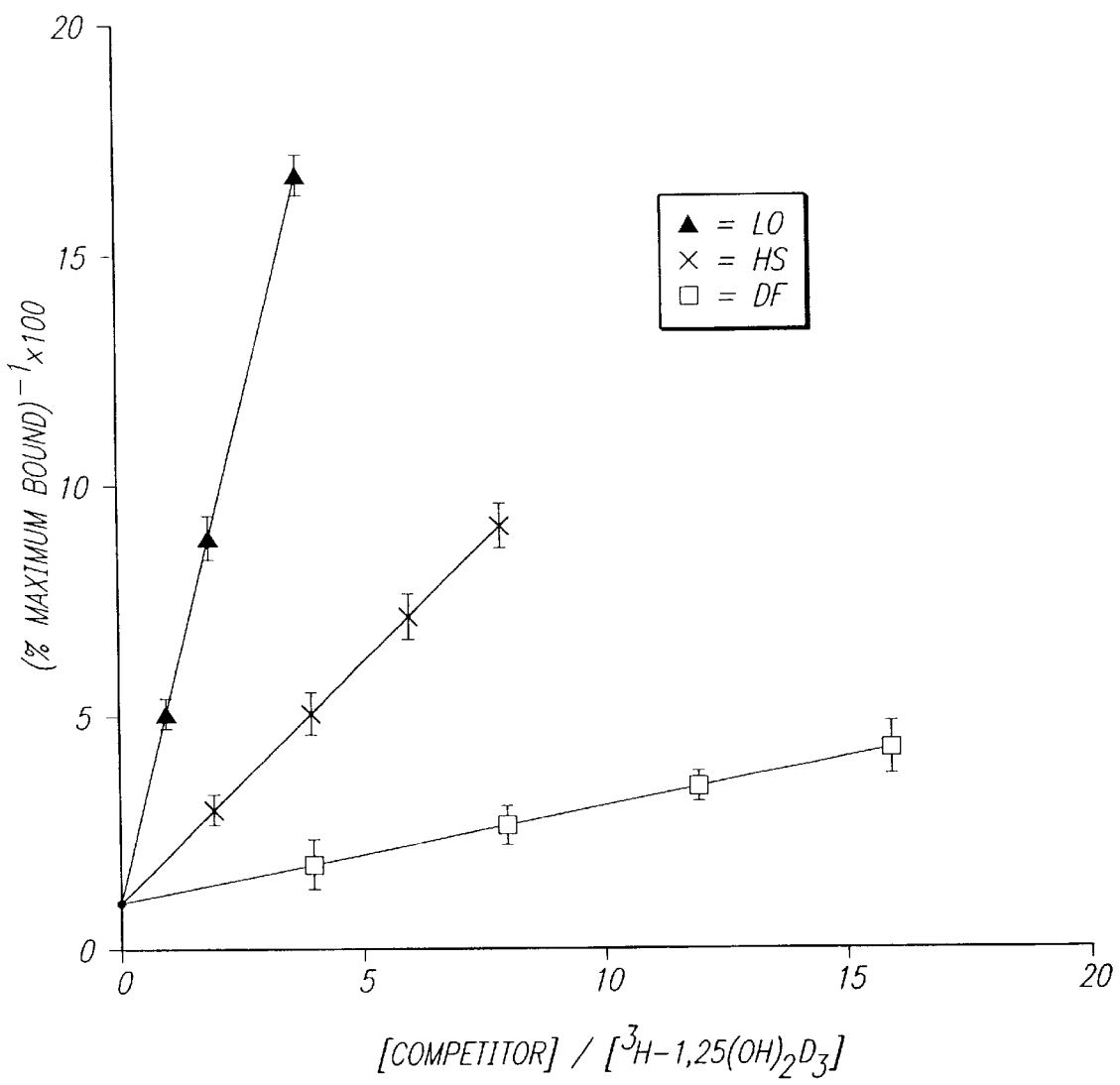
FIG. 8 presents results of the binding of 1α,25(OH)$_2$D$_3$ and selected analogs to the nuclear receptor for 1α,25(OH)$_2$D$_3$

FIG. 8 shows Relative Competitive Index (RCI) determination for representative analogs that bind to the nuclear receptor for 1α,25(OH)$_2$D$_3$ [VDR$_{nuc}$]. The assay is based upon the principles of a steroid competition assay. A fixed amount of [$^3$H]1α,25(OH)$_2$D$_3$ is mixed with increasing amounts of competitive analogs or the natural hormone, 1α,25(OH)$_2$D$_3$, and incubated with a VDR$_{nuc}$ receptor preparation from chick intestine mucosa. The results are presented for 1α,25(OH)$_2$D$_3$, analog LO [14α,15α-methano-1α,25(OH)$_2$D$_3$] (▲), analog HS [1α,18,25(OH)$_3$D$_3$] (×), and analog DF [22-(p-hydroxyphenyl)-23,24,25,26, 27-pentanor-1α-(OH) D$_3$] (□).

The results of FIG. 8 indicate that analogs LO, HS and DF bind 98%, 25%, and 5%, respectively, to the VDR$_{nuc}$ present in chick mucosa, compared to 100% binding of 1α,25(OH)$_2$D$_3$. These results indicate the relative ability of these particular analogs to regulate gene transcription through their binding to the VDR$_{nuc}$. From these results, it is clear that analog LO is as active in generating nuclear responses as is the 1α,25(OH)$_2$D$_3$. RCI of other analogs is shown in Table 6.

C. Intestinal Calcium Absorption and Bone Calcium Mobilization Assays

A primary fundamental physiological property of vitamin D and particularly 1α,25(OH)$_2$D$_3$ is its ability to stimulate the intestinal absorption of calcium and facilitate the availability of dietary calcium to the organism. Intestinal absorption of the calcium is measured by the intestinal calcium absorption (ICA) assay, developed in the model of vitamin-D deficient chicks. The ICA assay was used to determine the relative capability of the tested analog to stimulate intestinal Ca$^{2+}$ absorption.

A second important physiological action of 1α,25(OH)$_2$D$_3$ is its effects on bone cells. Under circumstances of a dietary shortage of calcium, the blood concentration of Ca$^{2+}$ falls and the individual becomes hypocalcemic. In order to prevent an extreme reduction in the blood concentration of Ca$^{2+}$, the organism utilizes 1α,25(OH)$_2$D$_3$ to activate bone resorbing cells, the osteoclasts, which in turn mobilize bone calcium and contribute it to the blood calcium pool thereby alleviating the hypocalcemia.

The bone calcium mobilizing (BCM) assay is also conducted in the vitamin D-deficient chick. The BCM assay determines the relative ability of the tested analog to mobilize bone calcium. The natural hormone 1α,25(OH)$_2$D$_3$ is very potent in the BCM assay. For example, when 1α,25(OH)$_2$D$_3$ in inappropriate amounts are used as a drug in human patients, the patient may become hypercalcemic and eventually hypercalciuria with nephrolithiasis and renal failure may develop. The BCM assay was used to determine the relative activity of the analogs of the invention to stimulate bone Ca$^{2+}$ mobilization.

Results of the testing of the analogs of the invention in vivo by the ICA and IBM assays are shown in FIG. 9 which illustrates the capability of analogs LO, EV and HR to stimulate intestinal Ca$^{2+}$ absorption (ICA) and bone Ca$^{2+}$ mobilizing activity (BCM). In this study, the analogs of 1α,25(OH) were given i.m. to vitamin D-deficient chicks 12 hours before the assay began. The activity produced by 100 pmol of 1α,25(OH)$_2$D$_3$ was set to be 100% for both ICA and BCM. The dose of the analogs required to achieve a biological response for either ICA or BCM equivalent to the 100 pmol dose of 1α,25(OH)$_2$D$_3$ was calculated and converted to a percentage. Results are expressed as mean +SE of groups of seven chicks. Each assay included a negative control (−D), that is no vitamin D was present, and a positive control, where vitamin D$_3$ (+D$_3$) was present in 3.25 nmol. The difference between the −D and +D$_3$ groups was significant at P<0.01. 1α,25(OH)$_2$D$_3$ and analogs LO [14α,15α-methano-1α,25(OH)$_2$D$_3$], EV [22-(m (dimethylhydroxymethyl)phenyl)-23,24,25,26,27-pentanor-1α-OH-D$_3$] and HR [(22R)-1,25(OH)$_2$-22,23-diene-D$_3$] were administered in 0.0065, 0.065, 0.65 and 6.5 nmol as shown.

Figure 9A:
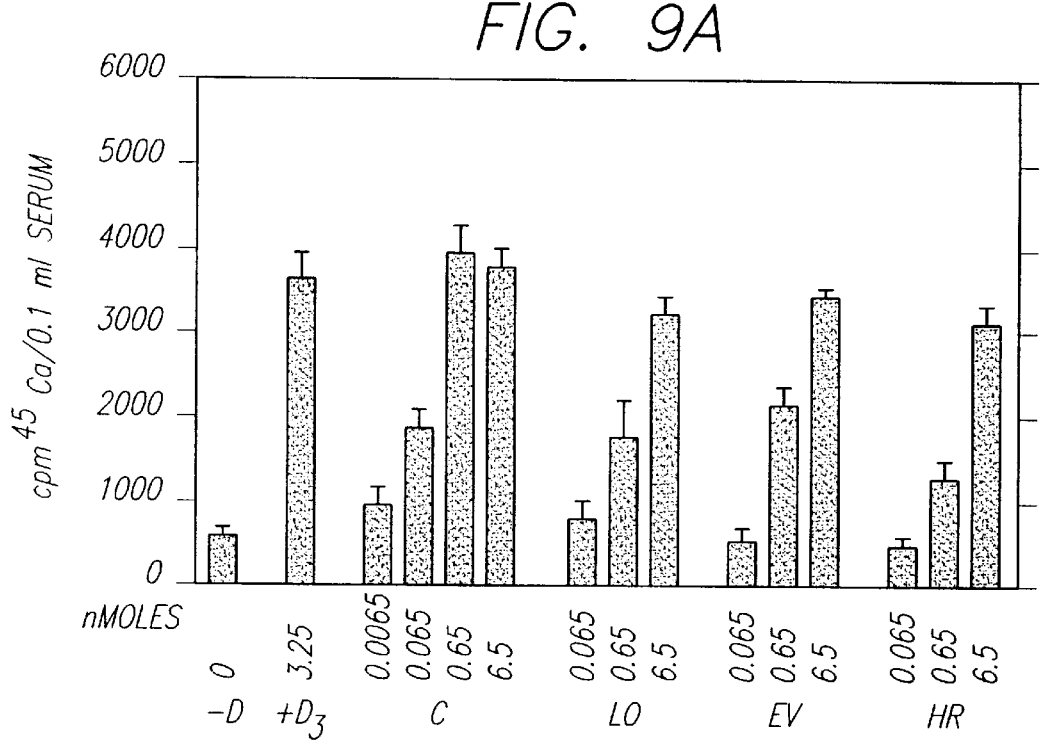
FIG. 9 presents results of a classical in vivo biological assay in vitamin D-deficient chicks which quantitates the relative abilities of 1α,25(OH)$_2$D$_3$ and selected analogs to stimulate an intestinal Ca$^{2+}$ absorption (ICA, FIG. 9A) and bone Ca$^{2+}$ mobilizing activity (BCM, FIG. 9B).
Figure 9B:
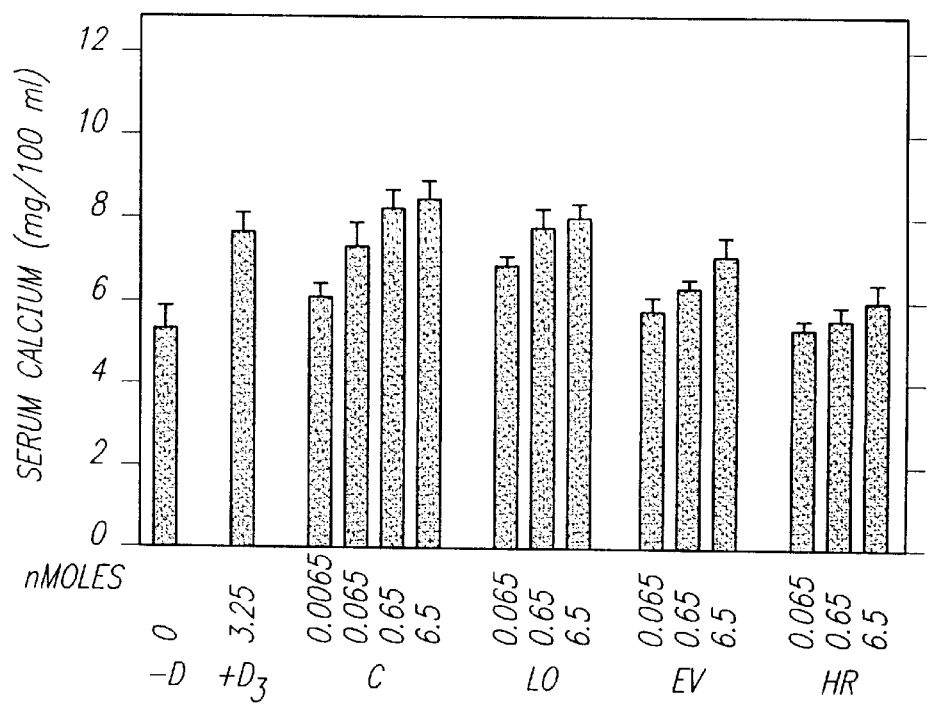

As illustrated in FIG. 9 and summarized in Table 6, the most potent stimulator of ICA and BCM was the reference compound 1α,25(OH)$_2$D$_3$. The comparative activity values expressed as percent of 1α,25(OH)$_2$D$_3$ for both ICA and BCM assays, as seen in FIG. 9A(ICA) and FIG. 9B(BCM), respectively, for each analog was as follows: analog LO (30%/80%), analog EV (30%/8%), and analog HR (12%/0.6%).

Table 6 shows ICA and BCM data for the analogs seen in FIG. 9 as well as other analogs of the invention. For example, analog LO which has the highest ICA (30%) and BCM (80%) relative to the ICA and BCM values for 1α,25(OH)$_2$D$_3$ would be a highly effective stimulator of bone Ca$^{2+}$ mobilizing activity (BCM) and reasonable stimulator of intestinal Ca$^{2+}$ absorption (ICA) and is therefore useful for treatment of hypocalcemia and rickets. Additionally, analogs DE and EV show stimulating activity in both ICA and BCM assays.

C. Cell Differentiation Assay

One of the recently discovered properties of the natural hormone 1α,25(OH)$_2$D$_3$, in addition to its involvement in calcium metabolism, is its potent ability to promote cell differentiation and/or inhibit cell proliferation, both these activities are related to cancer. These actions of 1α,25(OH)$_2$D$_3$ are dependent upon the widespread tissue distribution of receptors, both the VDR$_{nuc}$ and VDR$_{mem}$, as described in FIG. 2. 1α,25(OH)$_2$D$_3$ has been shown to be a potent cell differentiating agent in a variety of cell lines related to pathological states, such as leukemia, breast cancer, prostate cancer, and colon cancer, and as well in keratinocytes, cartilage cells, bone forming osteoblasts and the immune system cells.

The cell differentiation assay is used for a determination of relative potency of the analog vis-a-vis the potency of the reference compound 1α,25(OH)$_2$D$_3$ in promoting the cell differentiation or inhibiting the cell proliferation. The results of the cell differentiation assay are expressed as the effective dose-50 (ED-50) which is defined as 50% of the concentration required for a maximal response. ED-50 of 1α,25(OH)$_2$D$_3$ is determined to be 1. If the analog has ED-50 of 0.1, it achieves 50% of its maximal cell differentiation effect at a concentration of about one tenth that of 1α,25(OH)$_2$D$_3$ and is, therefore, ten times more effective.

Figure 10:
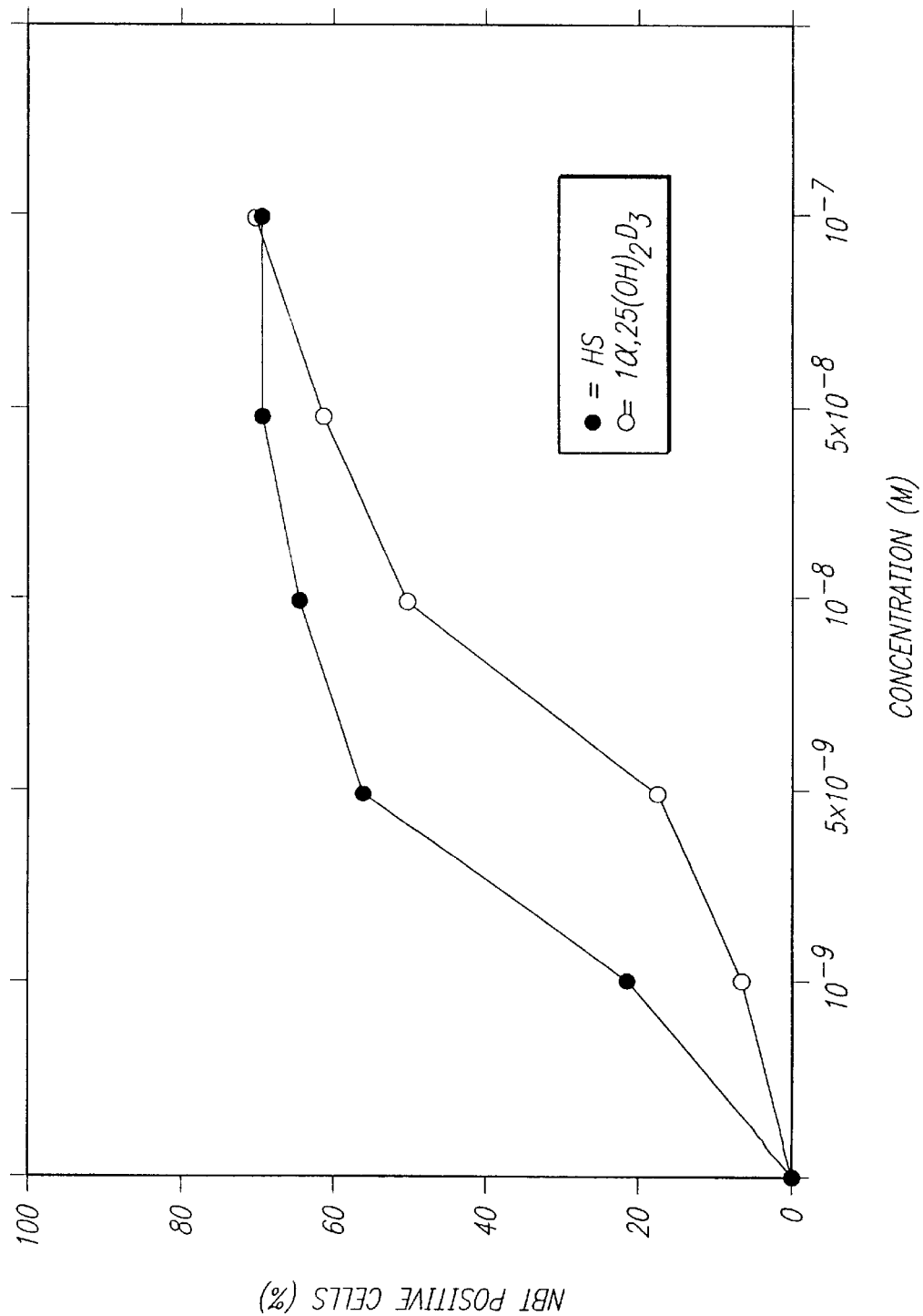
FIG. 10 presents results from a cell culture assay which quantitates the relative abilities of 1α,25(OH)$_2$D$_3$ and the analog HS to stimulate cell differentiation.

FIG. 10 is dose-response of analog HS or 1α,25(OH)$_2$D$_3$ on differentiation of HL-60 cells. The results are expressed as a percentage of untreated HL-60 cells which acquired, as a consequence of cell differentiation, the ability to effect reduction of nitro blue tetrazolium (NBT). Each point represents the mean of two experiments with triplicate dishes. open circles (○) show 1α,25(OH)$_2$D$_3$; closed circles (●) show analog HS.

In terms of the results presented in FIG. 10, it is clear that analog HS is significantly more potent than 1α,25(OH)$_2$D$_3$ in promoting the cell differentiation of HL-60 cells. Analog HS was found to have an ED-50 of 0.05 as compared to the 1.00 for $1\alpha,25(OH)_2D_3$ and is therefore about twenty times more potent at promoting the cell differentiation of HL-60 cells.

V. Rapid Responses

Rapid responses are initiated by occupancy of the $VDR_{mem}$ with an analog ligand that has the shape of a 6-s-cis oriented $1\alpha,25(OH)_2D_3$ (see FIG. 3). Rapid responses of the analogs of the invention are detected by their ability to achieve transcaltachia or mitogen activated protein kinase.

A. Transcaltachia

Transcaltachia is defined as the rapid stimulation of calcium transport across an epithelial cell of a perfused intestine. The process of transcaltachia is stimulated by hormone D [$1\alpha,25(OH)_2D_3$] or, according to the current invention, by 6-s-cis conformationally restricted analogs. The transcaltachia is a rapid response which occurs within one to several seconds to up to about three minutes as compared to a genomic response which is slow and usually takes about several minutes to several hours. The events comprising the initiation of the rapid response of transcaltachia by 6-s-cis conformationally restricted analogs are described below.

Transcaltachia is a component of the overall process describing the intestinal absorption of calcium, which is the classic response related to the vitamin D. For the intestinal absorption of calcium in humans vitamin D is essential because it increases the uptake of dietary calcium and makes it available for incorporation into the bones. The active agent of vitamin $D_3$ that is responsible for the stimulation of intestinal calcium absorption is a vitamin D metabolite $1\alpha,25(OH)_2D_3$, also called hormone D.

The general process of calcium transport across an intestinal epithelial cell involves three steps. The first step is the ingestion of calcium from food and the movement of calcium into the lumen of the intestine. Once the calcium is present in the small intestine, it moves across the outer brush-border membrane of the cell and into the interior of the epithelial cell. The second step is the calcium accumulation in membrane bounded vesicles known as lysosome-like vesicles. These calcium-bearing vesicles then move across the interior of the cell and respond to a signal indicating that they should be exported out of the cell into the adjacent blood compartment. The third step involves an initiating signal for the export of calcium out of the cell (exocytosis) regulated by hormone D in a 6-s-cis shape or by 6-s-cis locked analogs of the invention which are delivered by vitamin D binding protein (DBP) to the exterior surface of the epithelial cell. There, the hormone D or the 6-s-cis locked analog is unloaded from the DBP in its free form immediately adjacent to the outer cell membrane of an epithelial cell where the receptor $VDR_{mem}$ is resident, as shown in FIG. 4. The $VDR_{mem}$ is specific only for compounds in the 6-s-cis orientation and therefore binds only hormone D or analogs of hormone D which are in the 6-s-cis locked shape.

Formation of the receptor bound ligand complex, that is a $VDR_{mem}$/6-s-cis analog, results in the generation of a biological signal involving opening of voltage-gated calcium channels that send a message to the interior of the cell so that there is a prompt (rapid) initiation of the export of the calcium bearing lysosomal-like vesicles. Hence this activity is identified as a rapid response. This export process occurs within 1–3 minutes. Thus, the net effect of the delivery of a 6-s-cis locked analog by DBP to the blood bathed surface of an intestinal epithelial cell is the prompt stimulation of intestinal calcium transport that results in an increased exiting of calcium from the interior of the epithelial cell into the blood compartment. Thus, the process of transcaltachia increases the availability of calcium for delivery to the bone system where it is utilized for an increase in bone mineral content and density.

FIG. 11 is illustrative of the rapid response of transcaltachia and shows the effectiveness of conformationally restricted analogs JN and JM to stimulate the rapid response of transcaltachia. The reference compound is the conformationally flexible $1\alpha,25(OH)_2D_3$, which is able to achieve the shape of the 6-s-cis locked conformationally restricted analogs and thus interact with the $VDR_{mem}$ which has been implicated in transcaltachia.

Findings that only 6-s-cis locked analogs can elicit transcaltachia is extremely important for their therapeutic utility. While $1\alpha,25(OH)_2D_3$ has general utility for both genomic and rapid responses and is, therefore, much less specific, by identifying only certain types of analogs, that is 6-s-cis locked analogs as being able to elicit transcaltachia, the treatment of osteoporosis, for example, can be achieved without danger of causing hypercalcemia which can happen if large doses of $1\alpha,25(OH)_2D_3$ are administered. Such doses inappropriately activate the bone resorbing cells or osteoclasts.

FIG. 11 represents stimulated $^{45}Ca^{2+}$ transport in duodenal loops vascularly perfused with $1\alpha,25(OH)_2D_3$ or $1\alpha,25(OH)_2$-7-dehydrocholesterol (JM), or $1\alpha,25(OH)_2$-lumisterol (JN). Duodenal loops from normal, vitamin D-replete chicks were lumenally perfused with $^{45}Ca^{2+}$ (5 uCi/ml of buffer). To establish basal transport rates, celiac artery of controls were perfused with control medium for the first 20 min. The duodena were then either re-exposed to control medium containing the vehicle ethanol (0.005%, final concentration) through the celiac artery, or vascularly perfused with 300 pM or 650 pM agonist analogs JM or JN or with 650 pM of a control reference compound $1\alpha,25(OH)_2D_3$. The venous effluent was collected at 2 min intervals for liquid scintillation spectrophotometry of the $^{45}Ca^{2+}$. The results obtained during the treated phase were normalized to the average basal transport for each duodenum. Values represent mean ±SEM for n=4 in each group.

Figure 11A:
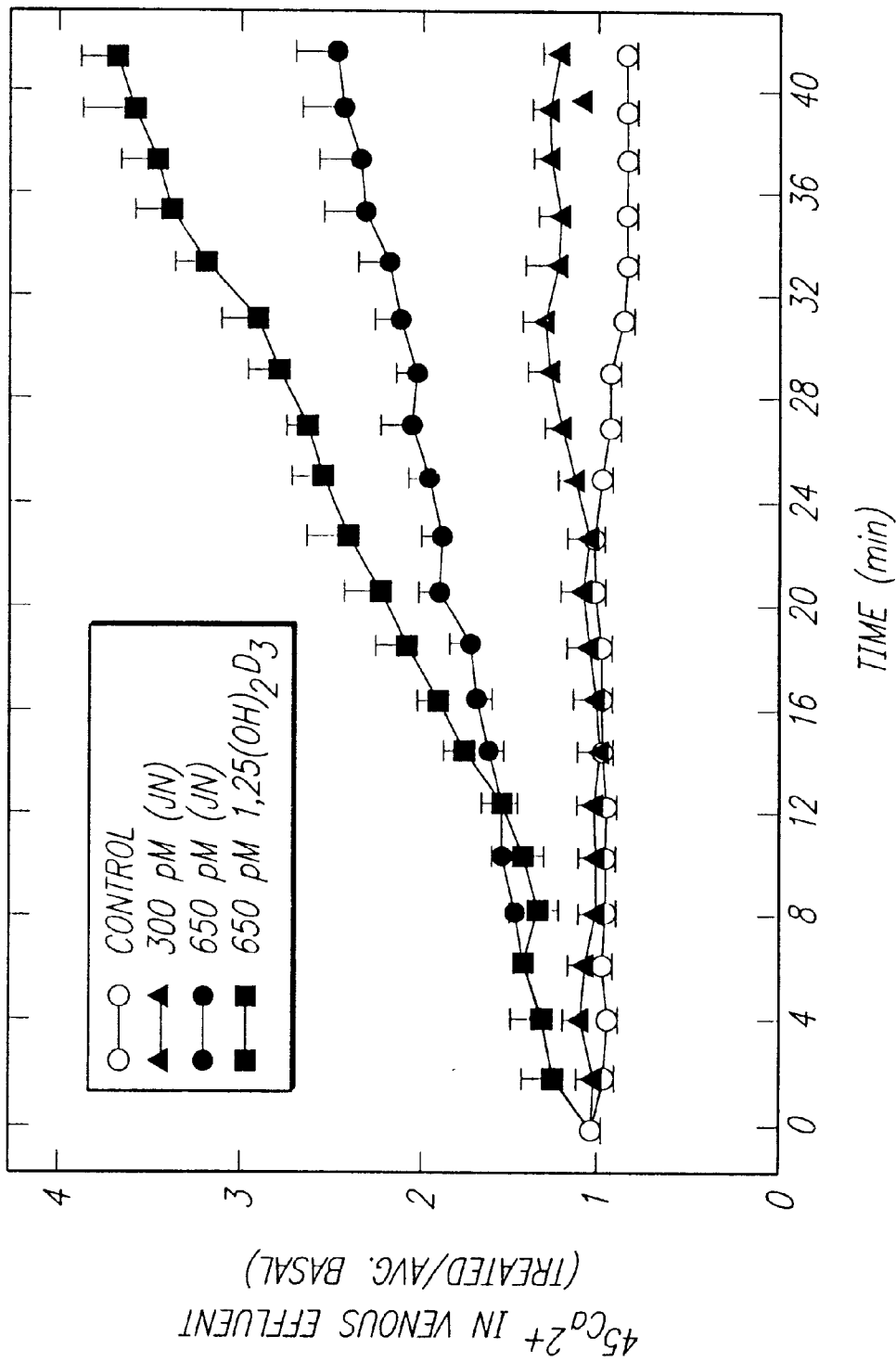
FIGS. 11(A & B) presents results from a bioassay of transcaltachia, the rapid hormonal stimulation of intestinal Ca$^{2+}$ absorption, as stimulated by 1α,25(OH)$_2$D$_3$ and selected analogs.
Figure 11B:
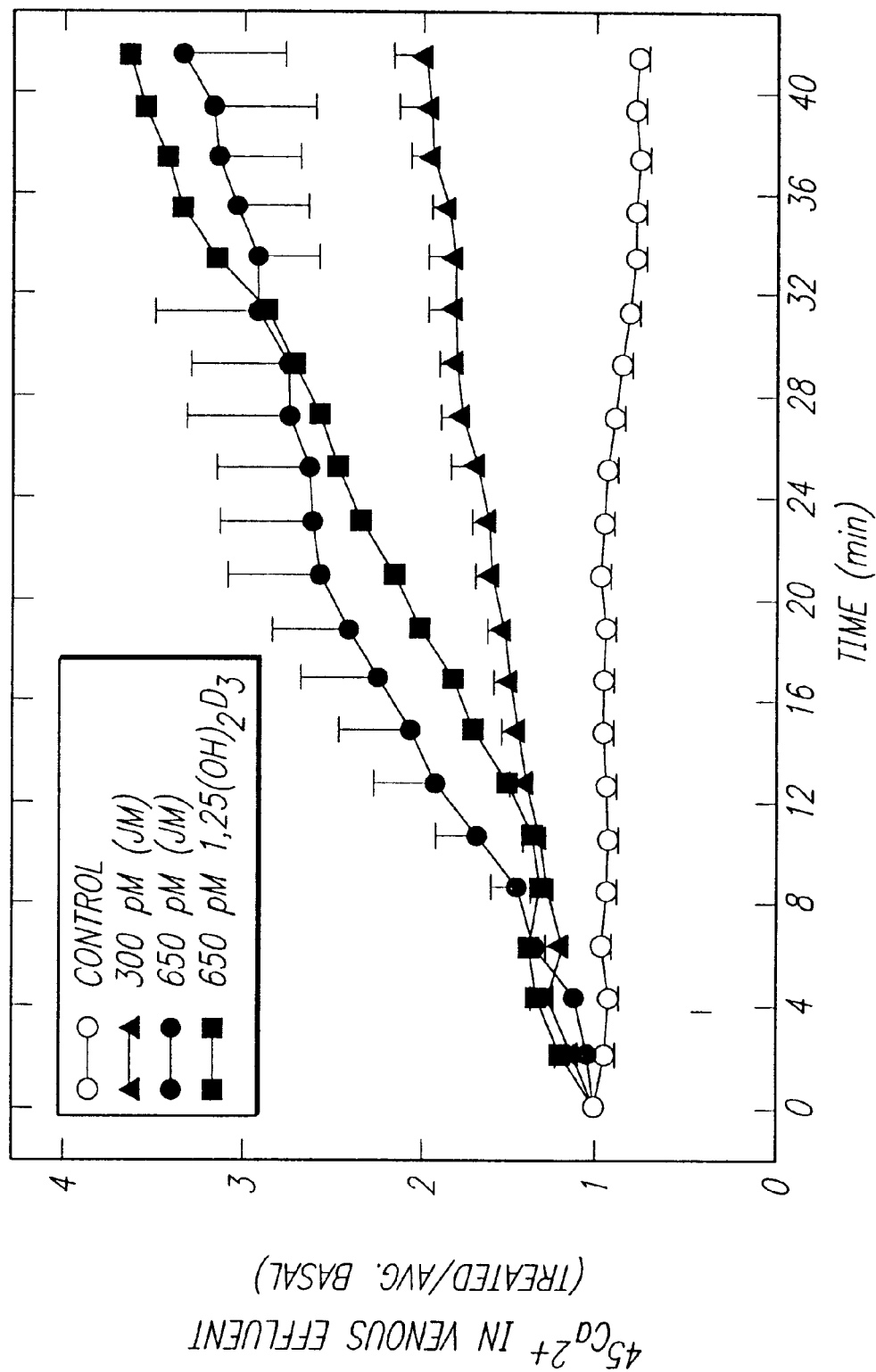

FIG. 11A shows results obtained after perfusion with analog JM. FIG. 11B shows results obtained after perfusion with analog JN. Included in each graph are both the vehicle control and 650 pM $1\alpha,25(OH)_2D_3$ of reference compound as a positive control. The results seen in FIGS. 11A and 11B indicate that the 6-s-cis locked analogs JM and JN are potent analogs of the rapid response process of transcaltachia. As seen in these figures, within first four minutes, both analogs have activity comparable or better than the reference compound.

As also seen in Table 6, analog JM has 60% of the potency of the conformationally flexible $1\alpha,25(OH)_2D_3$ to stimulate transcaltachia, while analog JN is 105% as potent as $1\alpha,25(OH)_2D_3$. Additionally, a 6-s-trans conformationally locked analog JB [1(,25(OH)-tachysterol$_3$] was found to have smaller than 5% activity of $1\alpha,25(OH)_2D_3$ in stimulating transcaltachia. From these results it is clear that only the 6-s-cis conformational analogs are the active agonists for rapid responses.

B. Mitogen Activated Protein Kinase

Enzyme mitogen activated protein (MAP) kinase belongs to the family of serine/threonine protein kinases which can be activated by phosphorylation of a tyrosine residue induced by mitogens or cell differentiating agents. MAP-kinase integrates multiple intracellular signals transmitted by various second messengers, and regulates many cellular functions by phosphorylation of several cytoplasmic kinases and nuclear transcription factors.

Agonists and antagonists of the invention activate or inhibit enzyme MAP-kinase localized in cytosolic/cell membranes and activate or inhibit related signal transduction pathways involved in modification of genomic responses of cells, for example, including their differentiation and/or proliferation.

1α,25-dihydroxyvitamin $D_3$ and particularly its 6-s-cis analogs are selective agonists of cytosolic localized mitogen-activated protein (MAP)-kinases. Further, 1β,25-dihydroxyvitamin $D_3$ (analog HL) is an antagonist of activation of MAP-kinases. These findings may be advantageously used in a method for activation or inhibition of vitamin D-related rapid responses. The method of the invention is useful for selective and rapid treatment of various diseases in which drug forms of vitamin $D_3$ and its metabolites are involved.

It has now been additionally discovered that the analogs of 1α,25-dihydroxyvitamin $D_3$ mediate activation of MAP-kinases, particularly MAP-kinase p42$^{mapk}$ phosphorylation, in a time and dose-dependent manner.

For the purposes of this study, three 6-s-cis locked analogs, namely HF (1α,25(OH)$_2$-previtamin-$D_3$), JM (1α, 25(OH)$_2$-7-dehydrocholesterol), and JN (1α,25(OH)$_2$-lumisterol$_3$) and one 6-s-trans locked analog, namely JB (1α,25(OH)-tachysterol$_3$) were prepared and studied for their ability to rapidly activate the MAP-kinase p42$^{mapk}$ pathway.

Such activation was achieved and mediated only by 1α,25(OH)$_2$D$_3$ analogs which can assume conformation that is closely approximated by the 6-s-cis conformation of 1α,25-dihydroxy-7-dehydrocholesterol and 1α,25-dihydroxylumisterol.

In order to determine whether MAP-kinase phosphorylation is specific and is altered by 1α,25(OH)$_2$D$_3$, the time-dependent effects of 1α,25(OH)$_2$D$_3$ on p42$^{mapk}$ phosphorylation was examined using human acute promyelocytic leukemia cells (NB4). In this study, the NB4 cells, cultured in 10% charcoal-stripped fetal calf serum (FCS) medium, were treated with 1α,25(OH)$_2$D$_3$ at 10$^{-8}$M for various time periods. Cells were then extracted and the phosphorylated MAP-kinase was immunoprecipitated with anti-phosphotyrosine antibody and further analyzed by Western blot using the antibodies against p42$^{mapk}$.

Figure 12A:
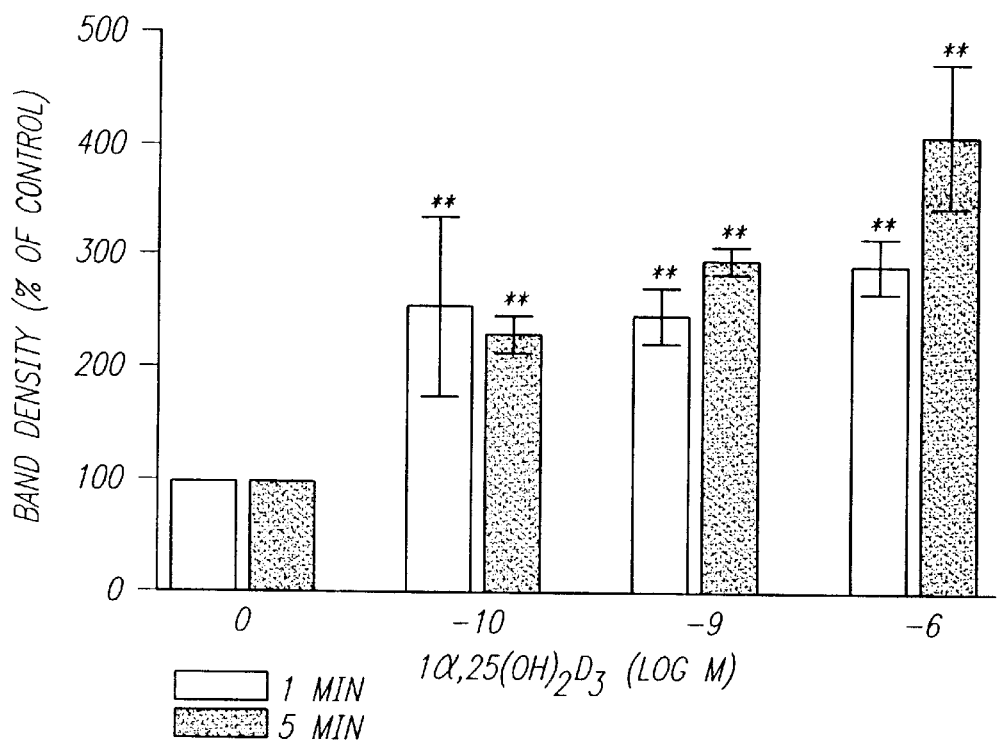
FIGS. 12(A & B) presents typical results from a cell culture assay which quantitates the relative abilities of 1α,25(OH)$_2$D$_3$ and selected analogs to stimulate mitogen-activated protein kinases (MAP-kinase).
Figure 12B:
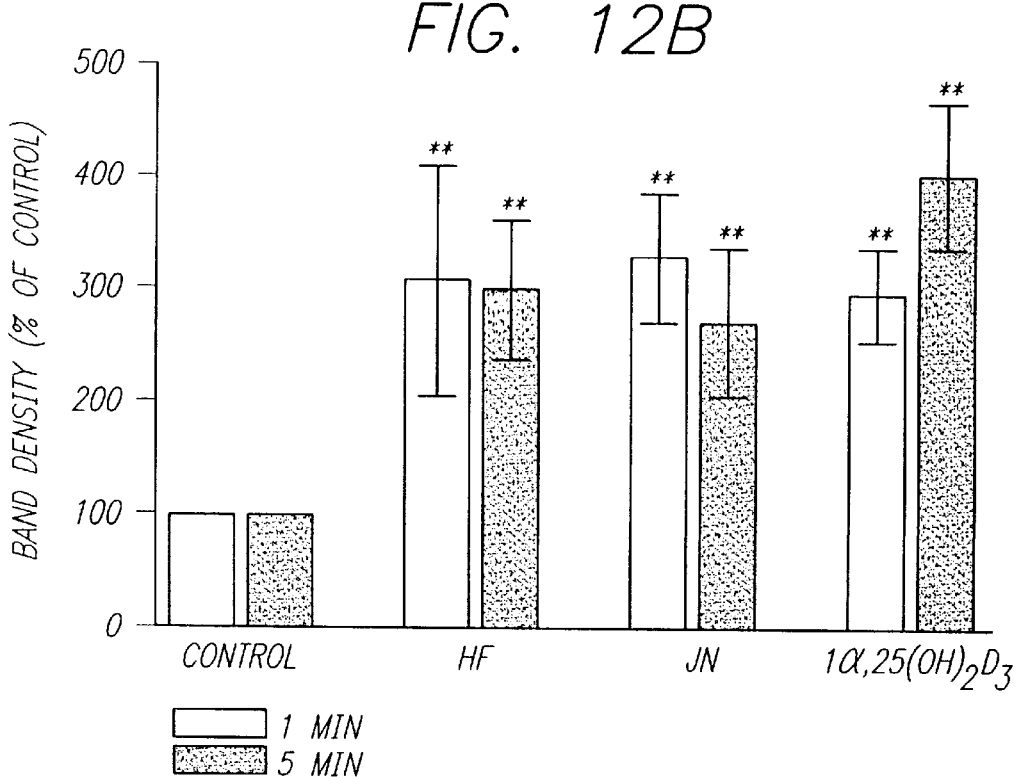

Specificity of p42$^{mapk}$ phosphorylation by 1α,25(OH)$_2$D$_3$ in NB4 cells is shown in FIG. 12. FIGS. 12A and 12B present the results of a densitometric scan of the Western blot analysis.

For studies illustrated in FIG. 12, the NB4 cells were treated with 1α,25(OH)$_2$D$_3$ at 10$^{-8}$M for 5 min and then extracted as described in Example 7. The lysate was further processed for anti-phosphotyrosine immunoprecipitation. The tyrosine-phosphorylated proteins were analyzed by Western blot according to Example 8. After transferring the proteins to the PVDF membrane, the membrane was further incubated with primary anti-p42$^{mapk}$ antibodies that were (+) or were not (−) pre-exposed to MAP-kinase peptide.

FIG. 12A shows results of a dose response by 1α,25(OH)$_2$D$_3$ for activation of MAP-kinase at either 1 or 5 minutes exposure to it. As seen in FIG. 12A, 1α,25(OH)$_2$D$_3$ significantly increased phosphorylation of p42$^{mapk}$ in NB4 cells. The specificity of the immunodetected MAP-kinase was confirmed by pre-blocking of the primary anti-MAP-kinase antibody with purified MAP-kinase peptide in a Western blot step.

FIG. 12B presents results describing the ability of the conformationally flexible 1α,25(OH)$_2$D$_3$ and a 6-s-cis locked analogs HF and JN to stimulate MAP-kinase activity in the human leukemia NB4 cell line. Testing conditions were the same as in FIG. 12A. As seen in FIG. 12B, analogs HF and JN activated MAP-kinase in 1 minute more than 1α,25(OH)$_2$D$_3$ and were only slightly less active at 5 minute intervals.

VI. Antagonist Analogs

A. Genomic Antagonists

Genomic antagonists are compounds that function as antagonists of the vitamin D nuclear receptor. The genomic antagonists are believed to cause the VDR$_{nuc}$ to assume a conformation which blocks transcriptional machinery.

B. Nongenomic-Rapid Response Antagonists

Rapid response antagonists are compounds that function to antagonize the DVR$_{mem}$. One representative conformationally flexible genomic antagonist is analog HL, namely 1β,25(OH)$_2$D$_3$.

FIG. 13 illustrates the ability of 1β,25(OH)$_2$D$_3$ to inhibit the agonist actions of 1α,25(OH)$_2$D$_3$ on the rapid response of transcaltachia.

For this study, the 1β,25(OH)$_2$D$_3$ analog HL was added to the perfused duodenum either in advance or simultaneously with 1α,25(OH)$_2$D$_3$ at varying concentrations. The data shown in FIG. 13 are the mean ±SEM from 4–5 duodena. Solid squares represent a combination of HL analog and 1α,25(OH)$_2$D$_3$. Open circles represent the negative control receiving no treatment with 1α,25(OH)$_2$D$_3$ or analog. FIG. 13B shows the dose-response relationship of 1β,25(OH)$_2$D$_3$ inhibiting the stimulation of transcaltachia by 300 pM 1α,25(OH)$_2$D$_3$. Data represent the ratio of treated to basal values ±SEM extracted from a time-course plot (as in panel A) at 32 minutes.

Figures 1, 13A:
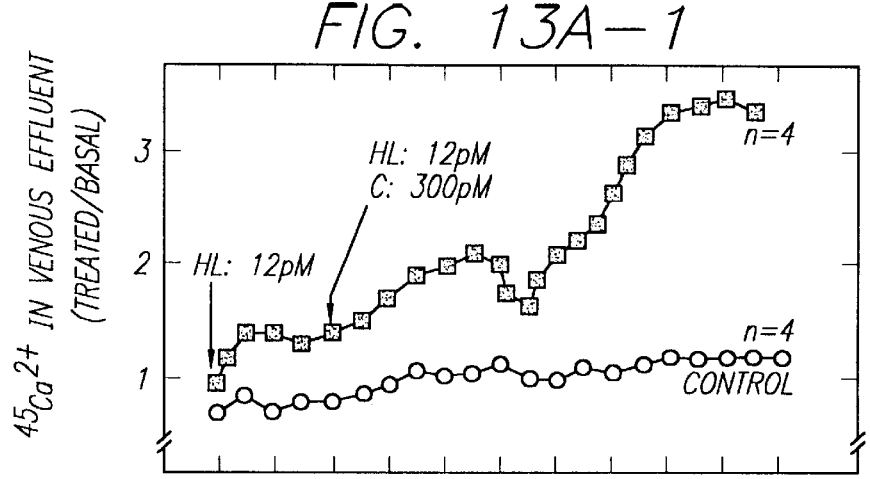
Figures 2, 13A:
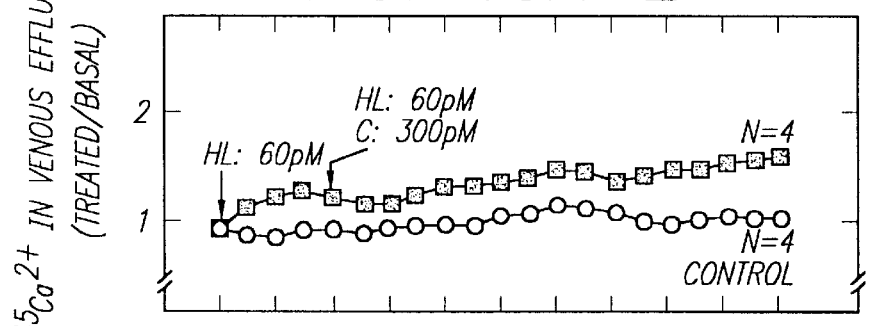
Figures 3, 13A:
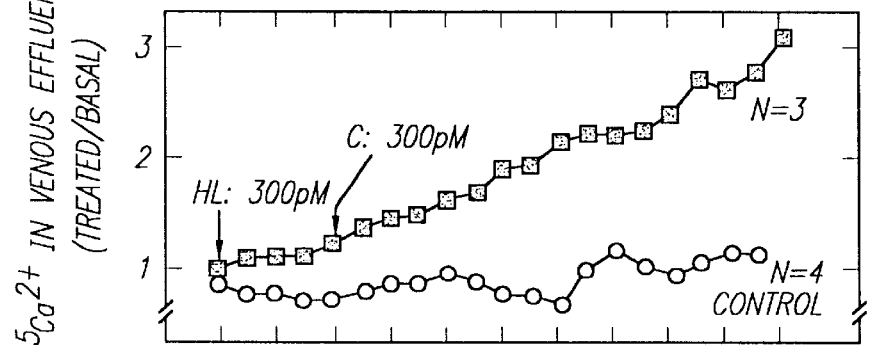
Figures 4, 13A:
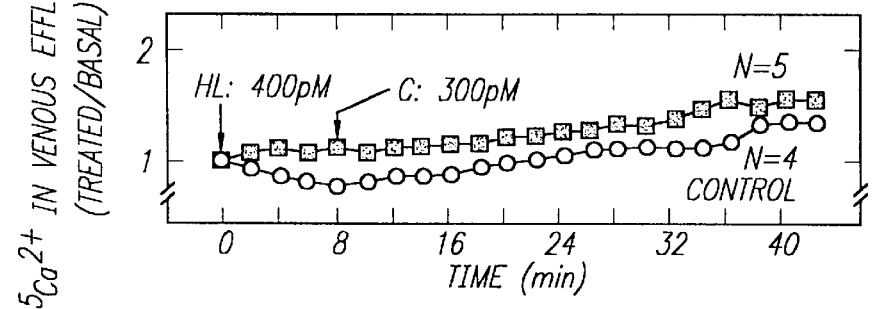
Figure 13B:
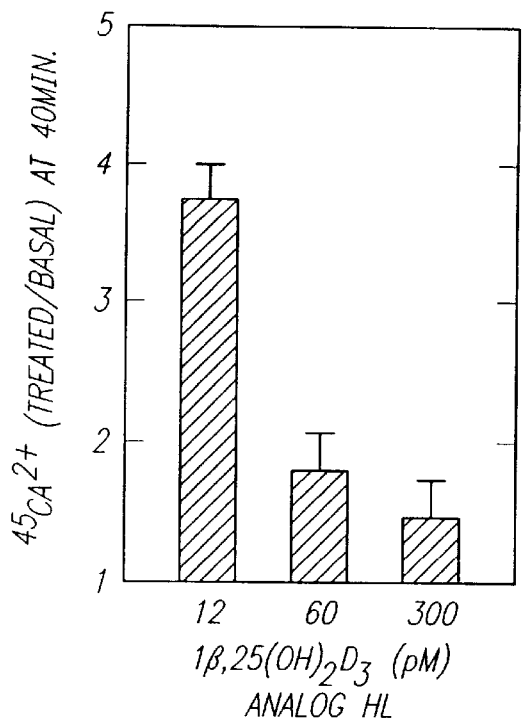
FIGS. 13(A & B) presents results from the assay of transcaltachia of the analog HL, namely 1β,25(OH)$_2$D$_3$, to inhibit the rapid response of stimulation of transcaltachia by 1α,25(OH)$_2$D$_3$.

The transcaltachia caused by 1α,25(OH)$_2$D$_3$ was particularly observable in FIG. 13A-1 where the antagonist HL was tested at 12 pM in combination with 1α,25(OH)$_2$D$_3$ at 300 pM. When the antagonist was added at 60 pM in advance of 300 pM 1α,25(OH)$_2$D$_3$ there was clear inhibition of transcaltachia (FIG. 13A-2). A similar inhibition of transcaltachia occurred (FIG. 13A-3) when the antagonist was 300 pM in advance of 300 pM 1α,25(OH)$_2$D$_3$. When the antagonist was added at 400 pM and the 1α,25(OH)$_2$D$_3$ was 300 pM, transcaltachia was clearly inhibited, as seen in FIG. 13A-4. When the analog was administered before the transcaltachia, followed by the administration of 1α,25(OH)$_2$D$_3$, transcaltachia was almost completely inhibited and the transport of the calcium ion across the intestinal wall was inhibited.

The results presented in FIG. 13 document the potent ability of 1β,25(OH)$_2$D$_3$ (HL) to block or antagonize the action of the conformationally flexible 1α,25(OH)$_2$D$_3$ to stimulate the rapid response of transcaltachia. These results further show that the antagonist analogs of the invention are able to inhibit the agonist activity of the native hormone D as well as that of agonist analogs of the invention.

Utility of 1β,25(OH)$_2$D$_3$ and other antagonist is based on their ability to inhibit the normal rapid actions of 1α,25(OH)$_2$D$_3$ or other agonist and to block the intestinal absorption of calcium when the individual has an abnormally elevated blood concentration of Ca$^{2+}$ in blood. Antagonists of the invention are, therefore, useful for treatment of conditions such as hypercalcemia. They prevent exacerbation of the extant condition of hypercalcemia.

In other experiments the analog 1β,25(OH)$_2$D$_3$ (HL) has also been found to be capable of antagonizing rapid responses of 1α,25(OH)$_2$D$_3$ to stimulate the opening of chloride channels in ROS 17/2.8 cells in osteoblast cells and the activation of MAP-kinase in human leukemia cells.

Analog's HL antagonist action is illustrated by its ability to inhibit the rapid responses of 1α,25(OH)$_2$D$_3$. These antagonist actions are illustrated in FIGS. 14 and 15.

Figure 14:
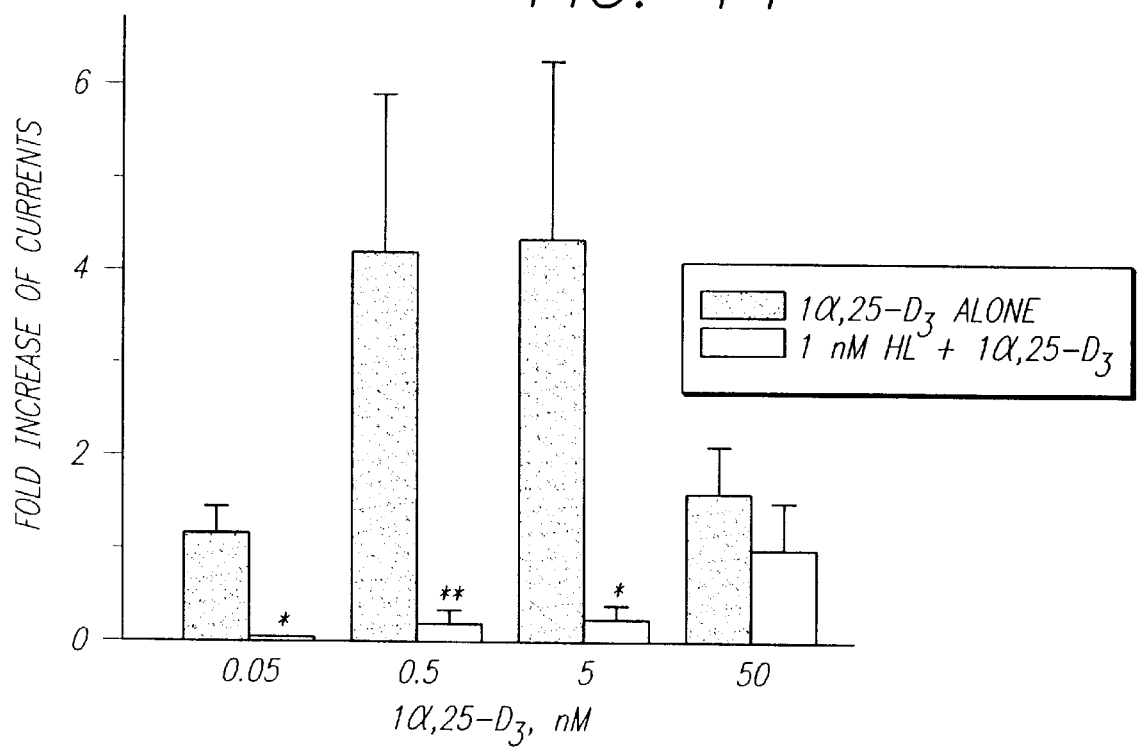
FIG. 14 illustrates the antagonist action of rapid responses elicited by treatment with 1α,25(OH)$_2$D$_3$ and by analog HL.

FIG. 14 shows opening or modulation of chloride channels in osteoblastic ROS 17/2.8 cells, following stimulation by 1α,25(OH)$_2$D$_3$. Specifically, FIG. 4 shows fold increase of outward currents in ROS 17/2.8 cells mediated by 1α,25 (OH)$_2$D$_3$ in the absence and presence of 1 nM 1β,25(OH)$_2$D$_3$. Fold increase of current amplitudes promoted by different concentrations of 1α,25(OH)$_2$D$_3$ were measured for currents elicited by a depolarizing step to 80 mV, in the absence and presence of 1 nM HL in the bath. In each case, at least a 3-min period was allowed after the addition of the analog to the bath for currents to reach a stable amplitude value. Currents were obtained in the presence of glutamate as the permeant anion since seals were more stable and long lasting than in the presence of Cl$^-$. Anion currents were isolated from inward Ba$^{2+}$ currents after blockade of Ca$^{2+}$ channels with 100 μM Cd$^{2+}$. 1α,25(OH)$_2$D$_3$alone showed a concentration-dependent effect on the promotion of anion currents (14 out of 15 cells, 93%), with a maximal value obtained for 0.5–5 nM hormone (black bars). In the presence of 1 nM 1β,25(OH)$_2$D$_3$ (white bars), the potentiation effect by 1α,25(OH)$_2$D$_3$ was significantly reduced (*, p<0.05; **, p<0.01, n=3–8) for a concentration of the hormone of 5 nM or less.

As seen in FIG. 14, the synthetic analog 1β,25(OH)$_2$D$_3$ (HL) which only differs from a natural metabolite in the orientation of the hydroxy group on carbon 1, has been shown to inhibit the ability of 1α,25(OH)$_2$D$_3$ to increase outward currents, that is, to open chloride channels in ROS 17/2.8 cells. Thus, 1α,25(OH)$_2$D$_3$ acting alone, over the range of 0.05–50 nM, is an agonist which opens chloride channels, but the addition of 1β,25(OH)$_2$D$_3$ at 1 nm blocks this agonist actions of 1α,25(OH)$_2$D$_3$.

Figure 15A:
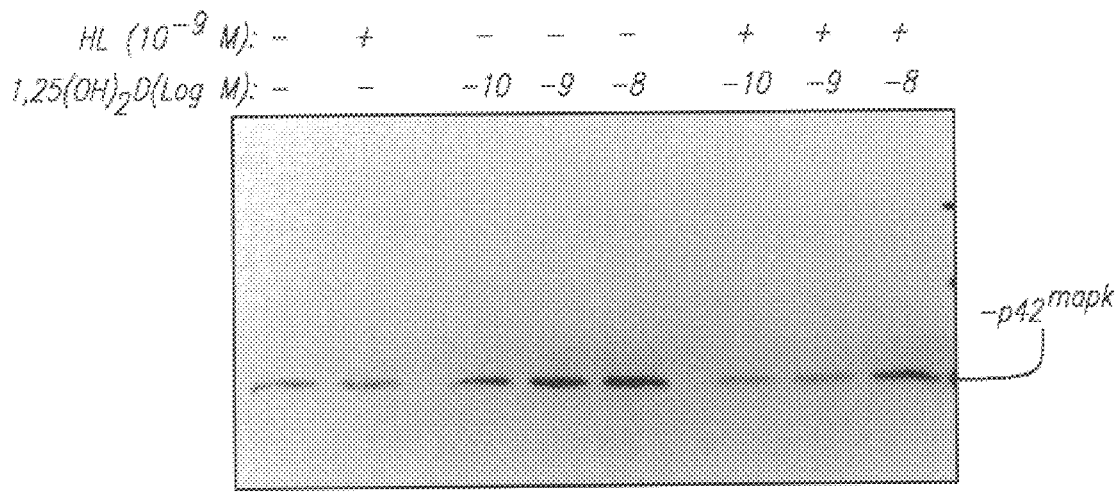
FIGS. 15(A, B & C) illustrates the inhibition of activation of MAP-kinase medicated by 1α,25(OH)$_2$D$_3$, with analog HL present at 10$^{-9}$ molar concentration.

FIG. 15 illustrates the stimulation of activation of MAP-kinase, specifically stimulation of phosphorylation of MAP-kinase by 1α,25-dihydroxyvitamin D$_3$ in promyelocytic NB4 leukemia cells.

FIG. 15 shows the effect of analog HL on 1α,25(OH)$_2$D$_3$-induced p42$^{mapk}$ phosphorylation in NB4 cells. (A) NB4 cells were treated with different doses of 1α,25(OH)$_2$D$_3$ in the presence or absence of HL at 10$^{-9}$ M for 5 min. (B) Equal loading of total MAP-kinase proteins was shown. (C) Quantitation of band density of the activated MAP-kinase is expressed as percent of control (set to 100%) from three separate experiments and is shown as the mean ±SEM. *, P<0.05 compared the HL-treated group with non HL-treated group.

Figure 15B:
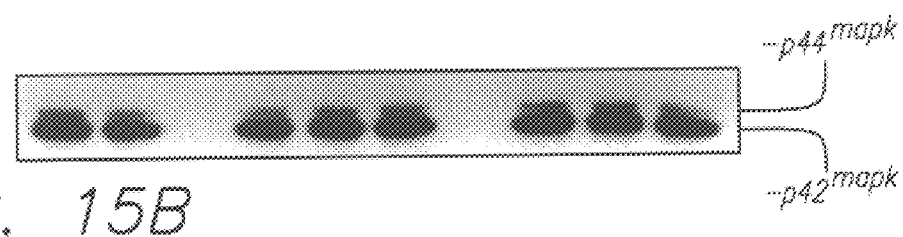
Figure 15C:
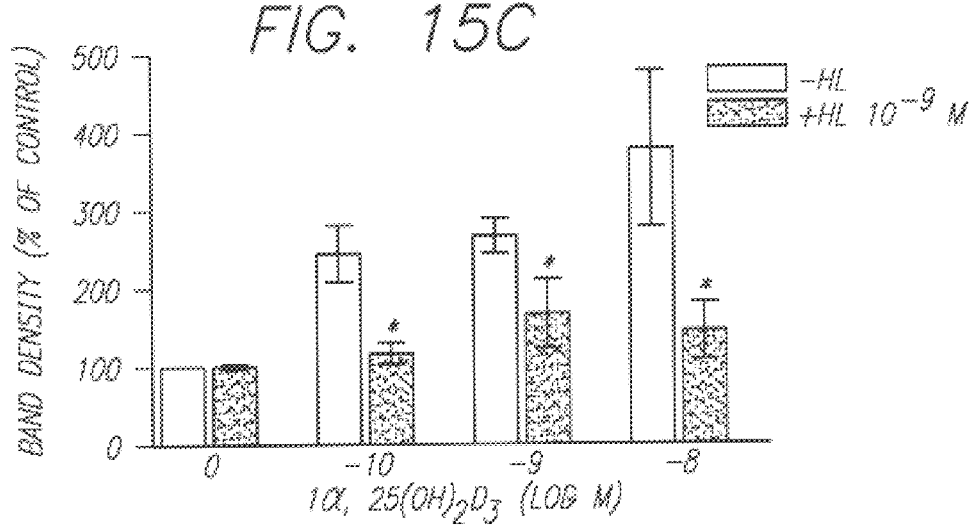

As shown in FIGS. 15B and 15C, 1β,25(OH)$_2$D$_3$ (analog HL) present at a concentration of 10$^{-9}$ mol was able to block 1α,25(OH)$_2$D$_3$, present at either 1, 10 or 100×10$^{-10}$ M, mediated activation of MAP-kinase. As seen in FIGS. 15B and 15C, when analog HL was present alone, there was no stimulation of MAP-kinase.

These results clearly show the antagonistic effect of analog HL on the rapid responses generated by 1α,25(OH)$_2$D$_3$.

The analog HL is, therefore, useful for treatment of any disease which involves opening or closing calcium channels and stimulation of MAP-kinase. This would include the calcium absorption process, transcaltachia occurring in the intestine as well as the changes in chloride currents of the bone osteoblast (bone forming) cells.

VII. Therapeutic Utility of The Analogs of the Invention

A. Evaluation of Therapeutic Utility of the Analyses.

From the perspective of drug development relative to analogs of 1α,25(OH)$_2$D$_3$, the primary objective is to identify an analog which has activity similar to or better than hormone D but which has more specifically defined properties with respect to binding to nuclear or membrane receptors but which does not lead to hypercalcemia. The ideal analog of 1α,25(OH)$_2$D$_3$ should have a much lower intrinsic ability to elevate the blood concentration of calcium than the parent 1α,25(OH)$_2$D$_3$ hormone.

Analog's profile evaluation includes as the first step, its evaluation of its ability to interact with the VDR$_{nuc}$ and DBP binding proteins under in vitro steroid competition assays, as outlined in FIGS. 7 and 8. Next, a given analog's ability to stimulate intestinal Ca$^{2+}$ absorption (ICA) and bone Ca$^{2+}$ mobilizing activity (BCM) in the vitamin D-deficient chick bioassay (see FIG. 9) is screened. This determines the potency of the ICA and BCM calcemic responses that the analog can generate in vivo over a 24 hour interval. Positive results of these assays indicate analog utility as a drug of choice for disease where the calcium absorption is disturbed, such as osteoporosis, rickets, etc. Next, the analog is screened to determine its relative ability to mediate classic genomic responses and/or rapid responses in a whole cell or in vivo setting. The classic genomic responses are determined using tissue culture conditions for the analog cell differentiating ability, as seen in FIG. 10, while the rapid responses are tested in assays that allow quantitation of MAP-kinase activation in NB4 cells and elicitation of transcaltachia. Results obtained in these assays delineate the analog as the drug of choice for treatment of acute hypocalcemia or chronically present hypocalcemic syndrom. Additionally, when the analog is found, for example, to be inhibitory in a cell proliferation assay, it becomes a good candidate for treatment of cancer growth or leukemia.

Then, depending upon the nature of the analog under study that is depending whether or not the analog is conformationally flexible (e.g., analogs EV, JV, LO), conformationally restricted (e.g., analogs JM, JN), or an antagonist of rapid responses (e.g., analog HL; see Table 1), an appropriate cell culture or in vivo assay is conducted. This allows determination of the ability of the analog to achieve a favorable response in an animal model of the human disease state under study. At the same time, the toxicology of in vivo chronic dosing with respect to the hypercalcemia-toxicity assay listed in the bottom line of Table 7, is performed and the analog is evaluated for its potential therapeutic activity.

B. Animal Models of Human Disease States

In order to extrapolate the results obtained in cell culture and to identify and evaluate new analogs of 1α,25(OH)$_2$D$_3$ which possess favorable therapeutic attributes in a variety of human disease states, it is essential to have access to appropriate animal in vivo model systems. Such model systems allow a critical evaluation of new drugs, in this case, of the analogs of the invention for the mediation of favorable responses, as well as allowing detection of the onset of unfavorable or toxic responses.

Table 7 presents a summary of animal models that have shown a demonstrated utility for drug development studies in the vitamin D endocrine system.

TABLE 7

Animal Models of Human Disease States

| Human Diseases | Model | Results |
| --- | --- | --- |
| Osteoporosis | Ovariectomized rat (1) | Increased bone density |
|  | Ovariectomized beagle (2) |  |
| Organ transplantation | Skin graft (3) | Graft survival |
|  | CBA > BALB/c mouse (4) |  |
|  | Cardiac graft (5) | Graft survival |
|  | Lewis > Buffalo rat (6) |  |
|  | Pancreatic islets (7) | Graft survival |
|  | NOD > NOD mice (8) |  |

TABLE 7-continued

Animal Models of Human Disease States

| Human Diseases | Model | Results |
|---|---|---|
| Immune system | Diabetes (9) | Reduction in insulitis |
| | Spontaneous NOD mice (10) | & diabetes |
| | Nephritis (11) | Reduction in proteinuria |
| | Allergic BN rats (12) | |
| | Encephalitis (13) | Prevention of disease |
| | Allergic disease (14) | |
| | Thyroiditis (15) | Reduction in thyroiditis |
| | Allergic disease in CB mice (16) | |
| | Lupus (17) | Reduction in skin lesions |
| | Spontaneous disease in MRL/1mice (18) | |
| Leukemia | SL mice + M1 myeloid (19) leukemia | Prolonged survival |
| | Nude mice + human myeloid leukemia (20) | Reduced incidence of disease |
| Breast cancer | Nude mice + Human MX1 (21) | Tumor volume reduction |
| | Wistar rat; DMBA induced (22) | Tumor volume reduction |
| Colon cancer | F344 rat; NMU induced (23) | Reduction in tumor incidence |
| Psoriasis | Cell cultures of human (24) root sheath cells | Reduction in psoriatic skin lesions |
| Hypercalcemia, kidney stones | Rats dosed 1× with $^{45}Ca^{2+}$ (25) & 5–7 days with test analog | ED-50 dose of analog to produce hypercalcemia & $^{45}Ca^{2+}$ deposition in kidney & muscle |

1. Metabolism, 39 Suppl. 1:18–23, (1990).
2. Metabolism, 39 Suppl. 1:24–26, (1990).
3. Transpl.Immunol., 1:72–76, (1993).
4. VitaminD.Molecular,CellularandClinicalEndocrinology, pp. 346–347, Berlin, New York: Walter de Gruyter (1998).
5. VitaminD.Molecular,CellularandClinicalEndocrinology, at 334–335.
6. Transplant.Proc., 26:3128–3129, (1994).
7. Diabetologia, 37:552–558 (1994).
8. Clin.Exp.Immunol., 88:301–306 (1992).
9. J.Clin.Invest., 87:1103–1107, (1991).
10. Clin.Immunol.Immunopathol., 54:53–63 (1990).
11. J.Cell.Biochem., 49:26–31 (1992).
12. J.Nutr.Sci.Vitaminol., 31:S44–S571985.
13. Am.Rev.Respir.Dis., 138:984–989 (1988).
14. Exp.Hematol., 13:722–732 (1985).
15. Endocrinology, 129:832–837 (1991).
16. AnticancerDrugs, 2:475–480 (1991).
17. CancerLett., 55:149–152 (1990).
18. J.Endo., 141:411–415 (1994).
19. Brit.J.Dermatol., 132:841–852 (1995).
20. ActaDerm.Venereol.(Stockh.), 77:196–202 (1997).
21. Urology, 50:999–1006 (1997).
22. VitaminD:Biochemical,ChemicalandClinicalAspectsRelatedto CalciumMetabolism, pp. 587–589, Berlin: Walter de Gruyter (1977).

B. Analog Delivery to the Tissues/Organs

The analog delivery to the target tissue is a primary aspect of the analog therapeutic utility. If the analog can be delivered to the target tissue quantitatively, then its therapeutic potential is high. If it cannot be delivered, then its therapeutic value is low. The key role played by the vitamin D-binding protein (DBP) in the transport of $1\alpha,25(OH)_2D_3$ or its analogs through the blood compartment, from its site of production or uptake, to make them available for uptake by target cells in tissue or organs to be treated has been illustrated in FIG. 4.

The DBP is a protein of 50 kDa with a ligand binding domain which can recognize and discriminate various functional groups and structural modifications on potential ligands. As shown in FIGS. 7 and 8, the DBP recognizes and bind various analogs of $1\alpha,25(OH)_2D_3$, which are subject of this invention with specific affinity. Since DBP determines the availability of its bound analog to target cells, it is important to define the relative affinity of a given analog to bind to DBP and also its ability to readily disassociate from such binding. The more available the analog is for uptake by a target cell, the more likely it is to interact with either the $VDR_{nuc}$ or the $VDR_{mem}$ and assert its therapeutic potential.

C. Therapeutic Effect of $1\alpha,25(OH)_2D_3$ on Specific Vitamin D Diseases—Clinical Applications

A. Agonist Analogs

The agonist analogs of the invention are useful for treatment or prevention of various diseases caused by or accompanying the deficiency or overproduction of vitamin D, particularly a deficiency of its metabolite $1\alpha,25(OH)_2D_3$. For treatment and/or prevention of these diseases, pharmaceutical compositions comprising conformationally flexible analogs or 6-s-cis locked analogs which are agonists or antagonists are used in administration modes as described in the following separate section of pharmaceutical compositions and modes of administration.

Conformationally flexible analogs subject to this invention which are listed above in Table 2 are exemplarized by analogs 14α,15α-methano-$1\alpha,25(OH)_2D_3$ (LO), 22-(m(dimethylhydroxymethyl)phenyl-23,14,15,16,17-pentanor 1a(OH)D₃ (EV), or $1\alpha,18,25(OH)_3D_3$ (HS). 6-s-cis locked analogs of $1\alpha,25(OH)_2D_3$ subject to this invention which are listed above in Table 4 are exemplarized by analog 1α,25 (OH)₂-lumisterol (JN).

These exemplary and other listed analogs are useful for treatment of, among others, osteoporosis, osteomalacia, rickets, renal osteodystrophy, psoriasis, organ transplantation, and several cancers, such as leukemia and prostate cancer. All these diseases are caused by the vitamin D or its metabolites deficiency or may be corrected by treatment with vitamin D metabolites, particularly $1\alpha,25(OH)_2D_3$.

Treatment and Prevention of Osteoporosis

Osteoporosis is the most common generalized disorder of bone characterized as a state of insufficiently calcified bone occurring as a consequence of a number of extraneous factors such as aging, menopause or other endocrine or nutritional deficiency. Due to these factors, the remodeling rate of bone is disturbed and there occurs either an increase in the relative rate of bone resorption or a decrease in the rate of bone formation.

The rationale for utilization of analogs of $1\alpha,25(OH)_2D_3$ in the treatment of osteoporosis is based on the documented decrease in serum concentrations of $1\alpha,25(OH)_2D_3$ in elderly subjects. When the serum level of $1\alpha,25(OH)_2D_3$ decreases, the calcium intestinal absorption is impaired. Administration of supplementary $1\alpha,25(OH)_2D_3$, or an analog equivalent thereof, corrects this conditions and results in improvement of the calcium absorption from the gut. That, in turn, leads to increased availability of calcium for bone structure and in increased mineral bone content and increased bone density. Any analog able to elicit transcaltachia and which is responsive in classic intestinal absorption assay and bone calcium mobilization assay are good candidates for replacement of $1\alpha,25(OH)_2D_3$ and for treatment and prevention of osteoporosis.

Particularly active for treatment of osteoporosis are the drug formulations of the $1\alpha,25(OH)_2D_3$, such as the conformationally flexible analogs LO [14,15-methano-1α,25 (OH)₂D₃], EV [22-(m(dimethylhydroxymethyl)phenyl-23, 14,15,16,17-pentanor 1α(OH)D₃], or HS [1α,18,25(OH)

$_3D_3$] or the drug formulations of 6-s-cis locked analogs of $1\alpha,25(OH)_2D_3$, such as analog JN [$1\alpha,25(OH)_2$-lumisterol]. These drugs are used to treat those forms of osteoporosis which are related to a lowered level of serum $1\alpha,25(OH)_2D_3$, because they rapidly stimulate intestinal $Ca^{2+}$ absorption thereby increasing the fraction of the dietary $Ca^{2+}$ that is absorbed by the intestine and made available to the skeletal system. In addition, these drugs effect the bone forming cells processes by stimulating bone formation which contributes to the amount of minerals present in bone.

The analogs are formulated to achieve an oral dose equivalent to 0.5–25 micrograms of $1\alpha,25(OH)_2D_3$/70 kg body weight, taken daily. The treatment duration is continuous for treatment of elderly patients and those with documented osteoporosis with serum $Ca^{2+}$ levels, urinary calcium excretion rates and alkaline phosphatase levels monitoring performed initially every two weeks and then on a monthly basis and bone mineral density determination at least once in every four months.

Treatment of osteoporosis is exemplarized in Example 8.

Treatment and Prevention of Osteomalacia and Rickets

Osteomalacia and rickets are caused by abnormal mineralization of bone and cartilage. Osteomalacia refers to the defect that occurs in bone in which the epiphyseal plates already have closed, therefore it is an adult disease, whereas rickets refers to the defect that occurs in growing bone, and it is therefore a disease of childhood. Abnormal mineralization in growing bone affects the transformation of cartilage into bone at the zone of provisional calcification. As a result, an enormous profusion of disorganized, nonmineralized, degenerating cartilage appears in this region, leading to widening of the epiphyseal plate and to swelling at the end of the long bones. Growth of the bone is retarded.

One of the primary causes of osteomalacia and rickets are disorders in vitamin D endocrine system. Such a problem may be increased due to insufficient sunlight exposure, nutritional vitamin D deficiency, the nephrotic syndrome and malabsorption or abnormal metabolism of vitamin D. Two types of vitamin D dependent rickets are known.

Vitamin D-dependent rickets type I is a recessive disease in which there is a low level of $1,25(OH)_2D$ resulting from a selective deficiency in the renal production. To treat this condition, moderate doses of vitamin D (0.625 µg) or physiological doses (0.5–1 microgram) of $1,25(OH)_2D_3$ are recommended.

Vitamin D-dependent rickets type II is a hereditary condition in which there is a relatively high level of circulating $1,25(OH)_2D$, however, due to a mutation in the vitamin D receptor which reduces the affinity of the receptor for its ligand $1,25(OH)_2D$ and therefore it does not function properly.

To treat this condition, large doses of $1,25(OH)_2D_3$ (20–60 micrograms) are used.

Adults with osteomalacia or children with rickets have a blood $Ca^{2+}$ concentration significantly below the normal range of 9.0–10.5 mg/100 ml. The serum $Ca^{2+}$ concentration in the disease state may be as low as 5.0–8.0 mg/100 ml. In addition, afflicted individuals typically have high levels of serum alkaline phosphatase, a marker for bone disease.

To treat adult osteomalacia, any of the drug formulations of the $1\alpha,25(OH)_2D_3$ conformationally flexible analogs which during testing were able to elicit both the rapid responses and genomic responses are suitable for treatment of osteomalacia. Thus, the conformationally flexible analogs DE, DF, EV, GE, GF, HH, HJ, HL, HQ, HR, HS, IB, JR, JS, JV, JW, JX, JY and LO are effective drugs for treatment of osteomalacia. Similarly, also suitable are formulations comprising 6-s-cis locked analogs JM, JN, JO and JP.

These drugs cause increase in the dietary $Ca^{2+}$ absorption by the intestine by promoting transcaltachia and by making calcium and phosphate available to the skeletal system to assure adequate mineralization of bone. By providing the substitute analogs of the vitamin D, the osteoblast is activated and begins to produce bone matrix that can be mineralized.

The analog of the $1\alpha,25(OH)_2D_3$ is formulated according to the conditions to be treated. Typically, the analog is administered orally or in a liquid form in an oral dose of equivalent to 0.25–2.0 micrograms dose of $1\alpha,25(OH)_2D_3$/ 70 kg body weight, daily. The dose is appropriately modified for children. The treatment duration depends on the treated conditions.

For treatment of vitamin D-dependent rickets type I, the child is treated until the bone mineralization is normalized. This is likely to take several months or even years. Example 9 illustrates the treatment regimen. For treatment of rickets type II, the child is treated with larger dosages of the analog and, its serum $Ca^{2+}$ levels are monitored weekly until the appropriate level is determined. The type II rickets can currently be treated only with gene therapy unless the analog of the invention is identified which is able to bind to the abnormal vitamin D receptor.

Treatment of adult osteomalacia is achieved in the same manner as described for treatment of osteoporosis.

Treatment and Prevention of Renal Osteodystrophy

Renal osteodystrophy is a bone disease that occurs in association with chronic renal failure. Chronic renal failure results from loss of the kidney ability to filter nitrogenous wastes from the blood for excretion in the urine. Chronic renal failure is a life threatening disease if the patient does not have regular access to hemodialysis. Over time of continued use of the dialysis procedure, however, renal osteodystrophy develops because the normal endocrine function of the kidney is compromised resulting in an impairment of the $25(OH)D_3$-1-hydroxylase synthesis. This hydroxylase is responsible for the enzymatic production of the steroid hormone, $1\alpha,25(OH)_2D_3$. Accordingly, patients suffering from chronic renal failure inevitably become hormone D [$1\alpha,25(OH)_2D_3$] deficient. As a consequence, typical symptoms of hormone D deficiency, namely impaired absorption of dietary calcium by the intestine occurs, leading to hypocalcemia and to increased secretion of parathyroid hormone (PTH). The PTH's secondary action in the instance of hypocalcemia is to stimulate the bone resorbing cells (osteoblasts) to mobilize bone calcium and make it available to the blood $Ca^{2+}$ pool.

Patients who are diagnosed with renal osteodystrophy display a reduced serum level of $1\alpha,25(OH)_2D_3$, a reduced level of intestinal $Ca^{2+}$ absorption, increased level of secretion of PTH and a greatly increased level of bone $Ca^{2+}$ mobilizing activity as stimulated by the excess PTH. In addition, the serum level of $Ca^{2+}$ is reduced to levels 7.5–9.0 mg $Ca^{2+}$/100 ml.

The main components of renal osteodystrophy are osteitis fibrosa and osteomalacia. Osteitis fibrosa is a pathological condition which develops as a consequence of an increased level of parathyroid hormone and is characterized by an increase in bone resorption and marrow fibrosis. Renal osteodystrophy arises in part because of defective renal production of the active form of vitamin D in chronic renal failure, as discussed above. Intestinal absorption of calcium is reduced. Low levels of $1,25(OH)_2D_3$ in serum are observed. Not only these low levels of vitamin D metabolite are responsible for reduced absorption of calcium but they are also implicated in and directly affect the synthesis and secretion of parathyroid hormone by negating the inhibitory effect of $1,25(OH)_2D_3$ on a parathyroid hormone gene transcription.

Treatment of these conditions is achieved by timely administration of the analog of the invention.

Any of the analogs belonging to the group of conformationally flexible analogs or 6-s-cis locked analogs of $1\alpha,25(OH)_2D_3$, are effective in stimulating the increase of intestinal $Ca^{2+}$ absorption and thus preventing a detrimental effect of parathyroid hormone leading to renal osteodystrophy. In addition, these analogs act on the osteoblast cells via processes dependent upon both genomic events as well as rapid events to stimulate bone formation which contribute to the amount of bone mineral present and reverse the PTH stimulation of the osteoblasts. These analogs also act directly on the parathyroid gland to change the set-point relationship between serum ionized $Ca^{2+}$ levels and the secretion of PTH. The parathyroid gland possess both $VDR_{nuc}$ and $VDR_{mem}$ which participate in the processes governing the secretion of PTH.

For treatment and prevention of renal osteodystrophy, the analog is formulated to achieve in oral dosage an equivalent of 0.5–2.0 micrograms of $1\alpha,25(OH)_2D_3$/70 kg body weight taken daily. The treatment is continued as long as necessary. Serum $Ca^{2+}$ levels, alkaline phosphatase levels and the serum level of immunoreactive PTH is monitored every two weeks until stabilization of conditions and then on a monthly basis. The bone mineral density is determined at least once monthly.

Treatment of Psoriasis

Psoriasis is a disorder of the skin characterized by dry, well-circumscribed silvery scaly papules and plaques of varying sizes. Psoriasis varies in severity from 1–2 lesions to a widespread dermatitis with disabling arthritis or exfoliation. Onset of psoriasis is usually between ages 10–40. While the general health of the individuals is not normally affected unless there is intractable exfoliation or severe widespread pustulation, psoriasis frequently creates in the afflicted individual a psychological stigma of an unsightly skin disease.

Keratinocytes are the most important cells of the skin and they have been found to have both the nuclear [$VDR_{nuc}$] and membrane [$VDR_{mem}$] receptors for $1\alpha,25(OH)_2D_3$. Under cell culture conditions, keratinocytes have been shown to display both genomic and rapid responses to $1\alpha,25(OH)_2D_3$ and related analogs.

The action of the vitamin D hormone ($1\alpha,25(OH)_2D_3$) and its analogs on keratinocytes growth and differentiation in psoriasis depends on an inappropriate stimulation of cell proliferation, on a decreased number of epidermal growth factor receptors, reduced levels of transforming growth factor β (TGFβ), and abnormalities in the skin proteins keratin, involucrin and loricrin. These proteins are necessary for the formation of the cornified envelope, the normal structure of the upper skin layer. Psoriasis patient show a deficiency in production of these proteins.

$1\alpha,25(OH)_2D_3$ and its analogs have been shown in cell cultures of keratinocytes to stimulate the production of keratin, involucrin and loricrin.

Any of the formulations of the conformationally flexible analogs or 6-s-cis locked analogs which are active and stimulate the keratinocyte proliferation and production of keratin, involucrin or loricrin are effective in treating individuals with psoriasis.

Two types of formulations are used. An analog is formulated for oral administration to achieve an oral dose equivalent to 0.5–2.0 micrograms of $1\alpha,25(OH)_2D_3$/70 kg body weight. The treatment is continuous, due to the continuous turnover and renewal of the keratinocytes of the skin. The suitability and efficacy of the treatment is monitored by following a progress of resolution of the external psoriatic plaques. Visual observations are often sufficient to evaluate the success of the treatment.

A topical ointment, cream or solution (50 µg/gram) of the drug formulations of the $1\alpha,25(OH)_2D_3$ conformationally flexible analogs or topical formulations of 6-s-cis locked analogs of $1\alpha,25(OH)_2D_3$, are used to treat individuals with external plaques of psoriasis.

Treatment and Prevention of Leukemia

Leukemia is a rapidly progressing form of cancer of the white blood cells, which is characterized by replacement of normal bone marrow by blast cells of a clone arising from malignant transformation of a hemopoietic stem cell. The most responsive form of leukemia for treatment with $1\alpha,25(OH)_2D_3$ analogs is acute myeloid leukemia (AML). AML occurs at all ages and is the more common acute leukemia in adults. Diagnosis of AML is usually made via evaluation of the white cell types present in a blood sample.

$1\alpha,25(OH)_2D_3$ is known to be an effective inhibitor of human leukemia cell proliferation and as well a stimulator of the cell differentiation. There have been a wide array of studies utilizing analogs of $1\alpha,25(OH)_2D_3$ on human leukemia cells in tissue culture as described in Blood, 74: 82–93 (1989). In addition, animal models for study of leukemia treatment are available as outlined in Table 7.

Human leukemia NB4 cells have been shown to have both $VDR_{nuc}$ and $VDR_{mem}$ and display both genomic and rapid responses to $1\alpha,25(OH)_2D_3$ and its analogs.

The drug formulation of the analog is oral or IV, containing 1–10 micrograms per day. In the initial treatment stage, the higher doses of the analog are administered intravenously or intraperitoneally. Treatment typically lasts 7–21 days but may last as long as necessary. The endpoints of the treatment are clinical biochemical determination of blood chemistries and particularly white blood cell morphology normalization. Because of their inhibitory action of human leukemia cell proliferation, analogs of the invention are especially effective in treating individuals with promyeloid leukemia.

Inhibition of Growth of Prostate Cancer Cells

Prostate cancer is the most common non-skin cancer among men in many Western societies. Nearly 50% of all prostate cancers are advanced at the time of diagnosis and are incurable by surgery. Although many such cancers can be controlled by androgen withdrawal, there are no effective therapies for androgen-resistant disease. There is extensive objective evidence that $1\alpha,25(OH)_2D_3$ induces prostate cancer cells to experience an inhibition of proliferation as well a selective differentiation. A variety of animal models of prostate cancer have been studied and are available as seen in Table 7. Prostate cells are known to possess the $VDR_{nuc}$ and $VDR_{mem}$.

Because of their antiproliferative activity, the analogs of the invention are effective in treating individuals with prostate cancer.

The dose regimen depends on the advanced state of the cancer. Doses are higher than renal osteodystrophy, typically 5–10 µg daily or more. The drug is administered either IV, IP or orally 3x weekly for several months. A major endpoint is a measurement of the presence of the prostate antigen in serum, which will be reduced if the drug is effective.

Analogs Utility For Organ Transplantation

The vitamin D endocrine system includes the immune system in its sphere of actions. Both activated T and B lymphocytes have the $VDR_{nuc}$ and $VDR_{mem}$. Although the physiological role of $1\alpha,25(OH)_2D_3$ in the immune system is not yet clearly defined, vitamin D-deficient animals and humans have a higher risk of infection, related to deficient macrophage function, whereas the monocytes/macrophage differentiation (tumor cell cytotoxicity, phagocytosis, mycobactericidal activity) is enhanced by $1\alpha,25(OH)_2D_3$.

Importantly, the natural killer cell activity is also enhanced by $1\alpha,25(OH)_2D_3$. This enhancing effect of the nonspecific immune defense contrasts with an inhibition of the antigen-specific immune system as demonstrated by a decreased T cell proliferation and activity. The antigen production by B cells can also be decreased by treatment with $1\alpha,25(OH)_2D_3$. As summarized in Table 7 several animal models have been used to evaluate the effect of $1\alpha,25(OH)_2D_3$ and its analogs on organ transplantation and rejection. These results support utilizing analogs of $1\alpha,25(OH)_2D_3$ to counter immunoreactions connected with human organ transplantation, such as kidney transplantation, heart, or combined heart and lung transplantation, skin transplantation, and pancreas transplantation.

Therapeutic Action of Antagonist Analogs

The analog HL [$1\beta,25(OH)_2D_3$] which is an antagonist for the rapid actions mediated by $1\alpha,25(OH)_2D_3$ is suitable to treat individuals experiencing hypercalcemia, particularly individuals with elevated plasma levels of $1\alpha,25(OH)_2D_3$ occurring in primary hyperparathyroidism or drug overdose of $1\alpha,25(OH)_2D_3$ or $1\alpha,(OH)D_3$ with drugs Rocaltrol or Alpherol.

The clinical hypercalcemia describes circumstances where the blood concentration of $Ca^{2+}$ is elevated above the normal range of 9.0–10.5 mg $Ca^{2+}$/100 serum. Elevations of blood $Ca^{2+}$ concentration above 12.0–13.0 mg/100 ml is cause for grave concern, and if left untreated it becomes life threatening as it can lead to tachycardia. Individuals who are found to have serum $Ca^{2+}$ levels above 12.0–13.0 mg/100 ml are frequently treated by hemodialysis with a low concentration of $Ca^{2+}$ in the dialysis bath in an effort to acutely lower their prevailing serum concentration of $Ca^{2+}$ to the normal range.

If, however, the causative factors which produced the hypercalcemia, e.g. primary hyperthyroidism or $1\alpha,25(OH)_2D_3$ intoxication, are ongoing, the excess levels of $1\alpha,25(OH)_2D_3$ inappropriately stimulates intestinal $Ca^{2+}$ absorption and bone $Ca^{2+}$ mobilizing activity. This process results in additional $Ca^{2+}$ being made available to the blood compartment from both the intestine dietary $Ca^{2+}$ and bone calcium (hydroxyapatite mineral), which is likely to result in hypercalcemia.

Treatment of the conditions with analog HL ($1\beta,25(OH)_2D_3$) which is a known antagonist of the rapid responses of transcaltachia, that is, it inhibits the intestinal $Ca^{2+}$ absorption and also the opening of $Ca^{2+}$ channels in osteoblast cells and thereby inhibiting bone $Ca^{2+}$ resorption by nearby osteoclasts.

Hypercalcemic patients are treated with oral or intravenous formulations of $1\beta,25(OH)_2D_3$, 10–50 micrograms every 12 hours. The effectiveness of treatment is determined by lowering and the absence of a further increase in the serum $Ca^{2+}$ level, and its fall to a more normal value.

VIII. Pharmaceutical Compositions and Administration

The present invention also relates to pharmaceutical compositions useful for treating vitamin D disorders. These compositions comprise an effective amount of the analog of the invention or the pharmaceutically acceptable salt thereof in acceptable, non-toxic carriers.

The composition may comprise solely of the one analog or an admixture of two or more analogs of the invention or a pharmaceutically acceptable salt thereof in a suitable amount to treat a subject and/or condition. In addition to the analog of the invention or the pharmaceutically acceptable salt thereof, the composition may include any suitable conventional pharmaceutical carrier or excipient as well as other medicinal agents, pharmaceutical agents, carriers, adjuvants, etc.

Activity of vitamin D and its metabolites is typically expressed as one international unit. One international unit corresponds to 1/40 of a microgram, that is 40 international units are equal to 1 microgram or 65 pmoles of vitamin D. The amount of the analog in the composition will depend on its relative activity vis-a-vis to the activity of vitamin D and particularly to its metabolite $1\alpha,25(OH)_2D_3$.

The analogs of the invention may be formulated with or in suitable pharmaceutical vehicles known in the art to form particularly effective pharmaceutical composition. Generally, an effective amount of active analog is about 0.001%/w to about 10%/w of the total formulated composition. The rest of the formulated composition will be about 90%/w to about 99.999%/w of a suitable excipient. However, these amounts may differ, depending of the intended use and the composition may, in some instances be formulated as the analog without any excipient.

For solid compositions of the analog of the invention particularly suitable for oral administration, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used.

For oral administration, a pharmaceutically acceptable non-toxic composition is formed by the incorporation of any of the normally employed excipients, such as those named above. Such oral compositions take the form of solids, solutions or suspensions, such as tablets, pills, capsules, powders, sustained release formulations and the like. Such compositions may contain 0.1%–95% of active ingredient, preferably 1%–70%.

When the analog is formulated as suppositories for systemic administration, traditional binders and carriers include for example polyalkylene glycols or triglycerides. Such suppositories may be formed from mixtures containing active ingredient in the range of 0.5%–10%, preferably 1–2%.

Liquid pharmaceutically administrable compositions suitable for oral or parenteral administration can, for example, be prepared by dissolving, dispersing, suspending, etc., the analog in a suitable carrier, such as, for example, water, saline, aqueous dextrose, glycerol, ethanol, and the like, to thereby form a solution or suspension. The carrier may optionally contain pharmaceutical adjuvants. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc.

Parenteral compositions are typically liquid compositions suitable for subcutaneous, intraperitoneal, intramuscular or intravenous administration. Injectables can be prepared in conventional forms, either as liquid solutions or suspensions, solid forms suitable for solution or suspension in liquid prior to injection, or as emulsions. Suitable excipients are, for example, water, saline, destrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

Actual methods of preparing such compositions and dosage forms are known, or will be apparent, to those skilled in this art. For example of preparing compositions of the invention, see *Remington's Pharmaceutical Sciences,* Mack Publishing Company, Easton, Pa., 15$^{th}$ Edition, 1975. The composition or formulation to be administered will, in any event, contain a quantity of the analog(s) in an amount effective to alleviate the disease symptoms of the subject being treated.

The invention also relates to a mode of administration of the compounds of the invention.

Administration of an active compound, that is the analog of the invention, alone, in admixture or in combination with other compounds, in a pharmaceutical composition described hereinafter can be via any of the accepted modes of administration for such agents suitable for treatment of diseases which affect the vitamin D endocrine system. These methods include oral, parenteral and other systemic administration. Depending on the intended mode of administration, the composition may be in the form of solid, semi-solid or liquid dosage forms, such as, for example, tablets, suppositories, pills, capsules, powders, liquids, suspension, drops or the like, preferably in unit dosage forms suitable for single administration of precise dosages.

Parenteral administration is generally characterized by injection, either subcutaneously, intramuscularly or intravenously. Parenteral administration also includes the implantation of a slow-release or sustained-release system, such that a constant level of dosage is maintained.

The amount of active compound administered depends on the subject being treated, the severity of the affliction, the manner of administration and the judgment of the prescribing physician. However, an effective dosage will be in the range of 0.001–15 µg/kg/day, preferably 0.01–3 µg/kg/day. For an average 70 kg human, this would amount to 0.07–1000 µg per day, or preferably 0.7–210 µg/day.

EXAMPLE 1

Ligand Receptor Competition Assay

This example describes a ligand receptor competitive assay used for determination of an analog's relative ability to bind to $VDR_{nuc}$ expressed as relative competitive index (RCI).

The relative affinity of nonradioactive $1\alpha,25(OH)_2D_3$ and each analog to compete with $[^3H]1\alpha,25(OH)_2D_3$ for binding to the $VDR_{nuc}$ of NB4 cells was carried out in vitro. The NB4 cells were collected from a fast growing stage and the cellular $VDR_{nuc}$ of $1\alpha,25(OH)_2D_3$ were extracted from KTED buffer containing 10 mM Tris-HCl, pH 7.4, 300 mM KCl, 1 mM EDTA and 5 mM DTT. After sonication, the cell extract was further centrifuged at 500× g for 10 min. The supernatant was collected for use in a ligand-receptor binding assay.

In this assay, increasing concentrations ($10^{-10}$ to $10^{-6}$ M) of nonradioactive $1\alpha,25(OH)_2D_3$ or the tested analogs were incubated with NB4 cell extracts in the presence of a fixed saturating amount of 1 pmole of $[^3H]1\alpha,25(OH)_2D_3$. The reciprocal of the percentage of maximal binding of $[^3H]1\alpha,25(OH)_2D_3$ was then calculated and plotted as a function of the relative analog concentration versus $[^3H]1\alpha,25(OH)_2D_3$. Each analog showed a linear plot and the slope of each curve represents the analog's competitive index value. The competitive index value for each analog is then normalized to the competitive index value of the radioactive $[^3H]1\alpha,25(OH)_2D_3$, thereby generating the value of Relative Competitive Index (RCI) where the RCI for $1\alpha,25(OH)_2D_3$ is defined as 100%.

The full description of the assay is found in *Methods in Enzymology: Vitamins and Co-Enzymes,* Vol. 67, 494–500 , Academic Press, NY(1980); *Biochem. Biophys. Res. Commun.,* 91: 827–834 (1979); and *Endocrinology,* 139(2): 457–465 (1998).

EXAMPLE 2

Vitamin D-Binding Protein Assay Relative Competitive Index

This example describes a Relative Competitive Index Assay used for determination of analogs binding affinity to vitamin D-binding protein.

Binding of the $1,25(OH)_2D_3$ and its analogs to the human vitamin D-binding protein (hDBP) was performed at 4° C. essentially as described previously in the *Journal of Biological Chemistry* 267; 3044–3051 (1992). One pmole of $[^3H]25(OH)_2D_3$ and increasing concentrations of $1\alpha,25(OH)_2D_3$ or its analogs ($10^{-10}$ to $10^{-6}$M) were added in 5 µl of ethanol into glass tubes and incubated with hDBP (0.18 µM) in a final volume of 1 ml (0.01 M Tris-HCl, 0.154 M NaCl, pH 7.4) for 4 h at 4° C. Phase separation was then obtained by the addition of 0.5 ml of cold dextran-coated charcoal.

The data was plotted as [competitor]/[$[^3H]25(OH)D_3$] vs. 1/[fraction bound]. The RCI was calculated as [slope of competitor]/[slope for $25(OH)D_3$]×100. Results are seen in FIG. 7. Although each analog was assayed in competition with $[^3H]25(OH)D_3$, the data are expressed as relative to the binding of $1\alpha,25(OH)_2D_3$, with its RCI set to 100. In this assay, when the RCI of $1\alpha,25(OH)_2D_3$ is set as 100, the RCI for $25(OH)D_3$=66,700.

EXAMPLE 3

In Vivo Assays of Intestinal Calcium Absorption and Bone Calcium Mobilization

This example describes assays used for determination of analogs biological activity in intestinal calcium absorption (ICA) and bone calcium mobilization (BCM) assays.

ICA and BCM were measured in vivo in the vitamin D-deficient chick model system according to *Biochem. Pharmacol.,* 18: 2347 (1969).

Twelve hours before assay, the chickens, which had been placed on a zero-calcium diet 48 h before assay, were injected intramuscularly with the vitamin metabolite $1\alpha,25(OH)_2D_3$ or analog (1–10,000 pmoles) dissolved in 0.1 mL of ethanol/1,2-propanediol (1:1, v/v). At the time of assay, 4.0 mg of $^{40}Ca^{2+}$+5 µCi of $^{45}Ca^{2+}$ (New England Nuclear) were placed in the duodenum of the birds lightly anesthetized with ether. After 30 min, the birds were decapitated and the blood was collected.

The radioactivity content, which is a measure of ICA, of 0.2 mL of serum was measured in a liquid scintillation counter (Beckman LS8000) to determine the amount of $^{45}Ca^{2+}$ absorbed.

BCM activity was estimated from the increase of total serum calcium concentration, as determined by atomic absorption spectrophotometry.

EXAMPLE 4

Cell Differentiation Assay

This example describes the cell differentiation assay and general conditions used for culturing HL-60, MCF-7, COS-7 and MG-63 cells. The details of the assay are described in *J. Biol. Chem.*, 268: 13811–13919 (1993).

HL-60 cells were seeded at $1.2 \times 10^5$ cells/ml, and 1,25(OH)$_2$D$_3$ or its analogs were added in ethanol in final concentration<0.2%, in RPMI 1640 medium supplemented with 10% heat-inactivated fetal calf serum (GIBCO), 100 units/ml penicillin, and 100 units/ml of streptomycin (Boehringer). After 4 days of culture in a humidified atmosphere of 5% CO$_2$ in air at 37° C., the dishes were shaken to loosen any adherent cells. All cells were then assayed for differentiation by NBT reduction assay and for proliferation by [$^3$H]thymidine incorporation. Results are seen in FIG. 10.

The COS-7 cells in Dulbecco's medium supplemented with 10% fetal calf serum (FCS) were seeded into 6-well plates to reach 40–60% confluence. After 24 h the medium was removed and refreshed with culture medium containing 2% dextran-coated charcoal-treated FCS. The cells were then cotransfected with the pSG5hVDR expression plasmid (1.5 μg) and the 1α,25(OH)$_2$D$_3$ responsive element (VDRE) linked to the reporter plasmid (CT4)$_4$TKGH (1.5 μg). The cells were then exposed to different concentrations ($10^{-11}$ to $10^{-6}$m) of 1α,25(OH)$_2$D$_3$ or analogs. The medium was assayed for the expression of human growth hormone using a radioimmunoassay.

MCF-7 cells were cultured in Dulbecco's minimal essential medium (DMEM) nutrient mix F12 (HAM) medium supplemented with 10% heat inactivated FCS, glutamine (2 mM), penicillin (100 units/ml) and streptomycin (0.1 mg/ml). Cultures were maintained at 37° C. in a humidified atmosphere of 5% CO$_2$ in air. MCF-7 cells were seeded at 5000 cells/well in the above-described medium in a 96-well microtiter plate in a final volume of 0.2 ml per well. Triplicate cultures were performed. After 24h, 1α,25(OH)$_2$D$_3$ or analogs were added in the appropriate concentrations from about $10^{-11}$ to about $10^{-6}$M for an incubation period of 72 h. Then 1 μCi of [$^3$H]thymidine was added to each well and the cells were harvested after a 4 h incubation with a Packard harvester and measured by the Packard Topcount System (Packard, Meriden, N.H.).

The MG-63 cells were seeded at $5 \times 10^3$ cells/ml in 96-well flat-bottomed culture plates (Falcon, Becton Dickinson, N.J.) in a volume of 200 μl of DMEM containing 2% of heat-inactivated charcoal-treated fetal calf serum and 1,25(OH)$_2$D$_3$ or its analogs were added in ethanol in final concentration<0.2%. After 72 hrs of culture in a humidified atmosphere of 5% CO$_2$ in air at 37° C., the inhibition of proliferation by [$^3$H]thymidine incorporation and measurement in the medium of osteocalcin concentration using a homologous human RIA.

Nitro blue tetrazolium (NBT) reduction assay was according to *J. Biol. Chem.*, 267: 3044–3051 (1992). Superoxide production was assayed by nitro blue tetrazolium-reducing activity as follows.

HL-60 cells at $1.0 \times 105$ cells/ml were mixed with an equal volume of freshly prepared solution of phorbol 12-myristate 13-acetate (200 ng/ml) and nitro blue tetrazolium (2 mg/ml) and incubated for 30 min at 37° C. The percentage of cells containing black formazan deposits was determined using a hemacytometer.

EXAMPLE 5

Transcaltachia Assay

This example describes the assay used for testing rapid response transcaltachia described in *J. Biol. Chem*, 268: 13811–13819 (1993).

White Leghorn cockerels (Hyline International, Lakeview, Calif.) were obtained on the day of hatch and maintained on a vitamin D-supplemented diet (1.0% calcium and 1.0% phosphorus; O. H. Kruse Grain and Milling, Ontario, Calif.) for 5–6 weeks to prepare normal vitamin D$_3$-replete chicks for use in the transcaltachia studies.

Measurements of $^{45}$Ca$^{2+}$ transport were carried out in perfused chick duodena. Normal vitamin D-replete chicks weighing approximately 500 g were anesthetized with 0.3 ml per 100 g Chloropent (Fort Dodge, Iowa), and the duodenal loop was surgically exposed. The celiac vein and blood vessels branching off from the celiac artery were ligated before cannulation of the celiac artery itself, and vascular perfusion was immediately initiated. Both the celiac artery and vein of the duodena were perfused with modified Grey's balanced salt solution (GBSS) +0.9 mM Ca which was oxygenated with 95% O$_2$ and 5% CO$_2$. A basal transport rate was established by perfusion with control medium for 20 minutes after the intestinal lumen was filled with $^{45}$Ca$^{2+}$. The tissue was then exposed to 1α,25(OH)$_2$D$_3$ or analogs or reexposed to control medium for an additional 40 minutes. The vascular perfusate was collected at 2 min intervals during the last 10 min of the basal and during the entire treatment period. Duplicate 100 μl aliquots were taken for determination of the $^{45}$Ca$^{2+}$ levels by liquid scintillation spectrometry. The results are expressed as the ratio of the $^{45}$Ca$^{2+}$ appearing in the 40 min test period over the average initial basal transport period as seen in FIG. 11.

EXAMPLE 6

MAP-kinase Activity

This example describes assays used for measurement of MAP-kinase activity in NB4 cells.

The detailed descriptions of the procedures are found in *Journal of Cellular Biochemistry*, in press, and in *Endocrinology*, 139:457–465 (1998).

Cell culture of NB4 cells

NB4 cells were obtained from Dr. K. A. Meckling-Gill (Guelph, Ont., Canada), and were originally isolated from a human patient with acute promyelocytic leukemia (APL) by Dr. Michel Lanotte at the Hospital Saint-Louis (Unite INSERM 301, Paris, France). The cell line is characterized by a translocation involving chromosomes 15 and 17, which is typical of the classical form of APL-M3 in the French-American-British [FAB] classification. NB4 cells were cultured in DMEM/F12 medium with 10% FCS at 5% CO$_2$ balanced air and were routinely passaged as suspension cultures and only passages 8 to 20 were used for each assay. Cell growth and viability were assessed using the trypan blue dye exclusion method and 95% of the cells showed viability in the experiment culture conditions.

Immunoprecipitation of Tyrosine-Phosphorylated Proteins

NB4 cells were cultured in 60-mm diameter dishes and treated with 1,25(OH)$_2$D$_3$ or analogs in 4 ml of DMEM/F12 containing 10% charcoal-stripped FCS. At the end of the incubation period, cells were washed once in cold PBS containing sodium vanadate at the concentration of 100 μM and further extracted with RIPA buffer containing 50 mM Tris-HCl, pH 7.4; 150 mM NaCl, 0.2 mM Na$_3$VO$_4$, 2 mM EGTA, 25 mM NaF, 1 Mm PMSF, 0.25% sodium deoxycholate, 1% NP40, 2 μg/ml leupeptin, 2 μg/ml aprotinin and 2 μg/ml pepstatin.

Insoluble material was removed in a microcentrifuge at 14,000 rpm for 10 min. Protein concentration was determined with a protein assay kit (Bio-Rad Lab, Hercules, Calif.). For immunoprecipitation, the supernatant was incubated with bead-conjugated monoclonal anti-phosphotyrosine antibody overnight at 4° C. The immunoprecipitates containing the tyrosine-phosphorylated proteins were washed four times with freshly-prepared RIPA buffer and further eluted with 2× Laemmli gel buffer.

At this point, the samples were either stored at −20° C. for further use or processed via Western blots. Equal loading of MAP-kinase protein was determined by running the Western blots using polyclonal anti-p42$^{mapk}$ antibody. For this purpose, samples were aliquoted from each cell extract before immunoprecipitation.

SDS Gel Electrophoresis and Western blot

Anti-phosphotyrosine immunoprecipitates of cell extract were resolved on 7.5% SDS-PAGE and transferred to PVDF membranes according to the manufacturer's instructions (Amersham, Arlington Heights, Ill.). The membrane was further immunoblotted using a rabbit anti-p42$^{mapk}$ polyclonal antibody overnight at 4° C. followed by incubation with secondary horseradish peroxidase-conjugated mouse anti-rabbit antibody for 1 hr at 25° C. The phosphorylated MAP-kinase bands were then visualized by enhanced chemiluminescence (ECL). A Ultrascan LX Laser Densitometer (LKB, Bromma, Sweden) scanned the density of the immuno-phosphoprotein bands. The results were normalized by protein loading and further plotted as percent of control of the band density. The specificity of p42$^{mapk}$ phosphorylation was determined by resolving the tyrosine-phosphorylated proteins in SDS-PAGE, transferring the proteins to PVDF membrane and then incubating the membrane with anti-p42 $^{mapk}$ polyclonal antibody that had or had not been pre-exposed to MAP-kinase peptide for two hours.

MAP-kinase Activity in Chick Intestinal Cells

Enterocytes were exposed either to 1α,25(OH)$_2$D$_3$ (0.01–10 nM) for 1 min, 1,25(OH)$_2$D$_3$ (1 nM) for 30 sec–5 min, or vehicle ethanol at 37° C. In some experiments, cells were pretreated with genistein (100 μM×10 min). Lysates were prepared and MAP-kinase (p42 and p44) was immunoprecipitated from cell lysates as described above.

After three washes in immunoprecipitation buffer and two washes in kinase buffer (10 mM Tris-HCl, pH 7.2, 5 mM MgCl$_2$, 1 mM MnCl$_2$, 1 mM dithiothreitol, 0.1 mM sodium orthovanadate, 1 mM phenylmethylsulphonyl fluoride, 20 μg/ml leupeptin, 20 μg/ml aprotinin and 20 μg/ml pepstatin), immune complexes were incubated at 37° C. for 10 min in kinase buffer (50 μl/sample) containing myelin basic protein as an exogenous substrate for MAP-kinase (20 μg/assay), 25 μM ATP, and [y$^{32}$P]-ATP (2.5 μCi/assay). To terminate the reaction, the phosphorylated protein product was separated from free [y$^{32}$P]-ATP on ion-exchange phosphocellulose filters (Whatman P-81). Filters were immersed immediately in ice-cold 75 mM H$_3$PO$_4$, washed (1×5 min, 3×20 min) and counted in a scintillation counter.

EXAMPLE 8

Treatment of Osteoporosis

This example shows method of treatment of osteoporosis using analogs of the invention, regimen and diagnostic evaluation of the disease progress.

Elderly patient suffering from pain in the bones is diagnosed with uncomplicated primary osteoporosis. Serum calcium, phosphorus, alkaline phosphatase levels, protein electrophoresis patterns are normal. The patient has, however, a low urinary calcium excretion rate of less than 75 mg/day which does not increase with calcium supplementation. On X-ray examination, the vertebrae show decreased radiodensity due to loss of trabecular structure.

The patient is diagnosed with osteoporosis and with impairment of calcium absorption. The patient is treated with 1–2 g of supplementary calcium and with 1–10 micrograms/day of orally formulated 14,15-methano-1α,25 (OH)$_2$D$_3$, analog LO.

EXAMPLE 9

Treatment of Vitamin D-Dependent Rickets Type I

This example shows method of treatment of rickets using the analog of the invention, regimen and diagnostic evaluation of the disease progress.

A child patient has visible abnormalities associated with rickets. Legs bowing is apparent in the femora and tibiae. The ends of these bones are flaring at the knees.

The child is diagnosed with rickets after a deficiency in renal production of 1,25(OH)$_2$D is discovered.

The child is put on a daily regimen of 1–10 micrograms of analog EV formulated as drops until the swelling decreases and the bone mineralization is brought under control.

EXAMPLE 10

Treatment of Psoriasis

This example shows the method of treatment of psoriasis using analogs of the invention and diagnostic evaluation of the disease process.

A patient is diagnosed with psoriasis on the basis of visual observation by a dermatologist of the presence of an external epidermis of silvery scaly papules and plaques.

The patient is provided with a topical cream containing 10–1000 μg/gram of the analog of the invention. The cream is used at the site(s) of the psoriasis. The topical treatment is administered and continues until the psoriatic condition is alleviated.

What is claimed:

1. A method for treatment of a disease connected with or caused by vitamin D$_3$ deficiency or overproduction, by providing a subject in need of such treatment a vitamin D$_3$ analog selected from the group consisting of analog LO, namely, 14α,15α-methano-1α,25(OH)$_2$D$_3$;

analog EV, namely, 22-(m-dimethylhydroxymethyl) phenyl-23, 24, 25, 26, 27-pentanor-1α(OH)D$_3$;

analog HS, namely, 1α,18,25(OH)$_2$D$_3$;

analog DE, namely, 22-(m-hydroxyphenyl)1α,25(OH) 2D$_3$;

analog DF, namely, 22-(p-hydroxyphenyl) 1α,25(OH) $_2$D$_3$;

analog IB, namely, 23-(m-dimethylhydroxymethyl) phenyl-22-yne-24, 25, 26, 27-tetranor-1α(OH)D$_3$;

analog JX, namely, 22-(p-hydroxyphenyl)-23, 24, 25, 26, 27-pentanor-D$_3$;

analog JY, namely, 22-(m-hydroxyphenyl)-23, 24, 25, 26, 27-pentanor-D$_3$.

2. The method of claim 1 wherein the disease connected with or caused by vitamin D$_3$ deficiency or vitamin D$_3$ overproduction is rickets, osteomalacia, osteoporosis, osteopenia, osteosclerosis or renal osteodystrophy, psoriasis, medullary carcinoma, Alzheimer's disease, hyperparathyroidism, hypoparathyroidism, pseudoparathyroidism, secondary parathyroidism, diabetes, cirrhosis, obstructive jaundice or drug-induced metabolism, glucocorticoid antagonism, hypercalcemia, malabsorption syndrome, steatorrhea, chronical renal disease, hypophosphatemic vitamin D-resistant rickets, vitamin D-dependent rickets, rickets type I, rickets type II sarcoidosis, leukemia, prostate cancer, breast cancer, colon cancer, organ transplantation or an immunodisorder, wherein said disease is treated with a pharmaceutical composition comprising at least one analog selected from the group consisting of analogs LO, EV, HS, DE, DF, IB, JX, and JY or a pharmaceutically acceptable salt thereof in admixture with a pharmaceutical carrier, excipient or adjuvant.

3. The method of claim 2 wherein the disease is osteoporosis, osteomalacia, rickets, renal osteodystrophy, hyperparathyroidism or hypercalcemia.

4. The method of claim 3 wherein the disease is rickets and the analog used for treatment of rickets is the analog LO, EV or HS.

5. The method of claim 4 wherein the analog used for treatment of rickets is administered in a pharmaceutical composition comprising between 0.5 and 1.0 µg per 70 kg weight of body weight.

6. The method of claim 2, wherein the analog is administered in a dose equivalent to 0.5–25 ug of $1\alpha,25(OH)_2D_3$ per 70 kg of body weight.

7. The method of claim 3 wherein the disease is osteoporosis and the analog used for treatment of osteoporosis is the analog LO, EV or HS.

8. The method of claim 1 wherein the analog is the analog LO, EV or HS.

9. The method of claim 9 wherein the disease is osteomalacia and the analog used for treatment of osteomalacia is the analog LO, EV, DE, DF, IB, JX, JY or HS.

10. The method of claim 9 wherein the analog is the analog LO, EV or HS administered in a pharmaceutical composition comprising an equivalent of between 0.5 and 2 µg of $1\alpha,25(OH)_2D_3$ per 70 kg of body weight for treatment of osteomalacia.

11. A pharmaceutical composition comprising at least one analog of $1\alpha,25$-dihydroxyvitamin $D_3$ selected from the group consisting of analog LO, namely, $14\alpha, 15\alpha$-methano-$1\alpha,25(OH)_2D_3$;

analog EV, namely, 22-(m-dimethylhydroxymethyl)phenyl-23, 24, 25, 26, 27-pentanor-$1\alpha(OH)D_3$;

analog HS, namely, $1\alpha,18,25(OH)_2D_3$;

analog DE, namely, 22-(m-hydroxyphenyl)$1\alpha,25(OH)_2D_3$;

analog DF, namely, 22-(p-hydroxyphenyl) $1\alpha,25(OH)_2D_3$;

analog IB, namely, 23-(m-dimethylhydroxymethyl)phenyl-22-yne-24, 25, 26, 27-tetranor-$1\alpha(OH)D_3$;

analog JX, namely, 22-(p-hydroxyphenyl)-23, 24, 25, 26, 27-pentanor-$D_3$; and analog JY, namely, 22-(m-hydroxyphenyl)-23, 24, 25, 26, 27-pentanor-$D_3$, in admixture with a pharmaceutically acceptable carrier, excipient or adjuvant.

12. The composition of claim 11 useful for treatment of rickets, osteomalacia, osteoporosis, osteopenia, osteosclerosis, renal osteodystrophy, psoriasis, medullary carcinoma, Alzheimer's, hyperparathyroidism, hypoparathyroidism, pseudoparathyroidism, secondary parathyroidism, diabetes, cirrhosis, obstructive jaundice or drug-induced metabolism, glucocorticoid antagonism, idiopathic hypercalcemia, malabsorption syndrome, steatorrhea, tropical sprue, chronical renal disease, hypophosphatemic vitamin D receptor (VDRR), vitamin D-dependent rickets, or sarcoidosis, leukemia, prostate cancer, breast cancer, colon cancer, organ transplantation or an immunodisorder.

13. The composition of claim 12 in a solid or liquid form for oral or parenteral administration.

14. The composition of claim 13 useful for treatment of osteoporosis.

15. The composition of claim 13 useful for treatment of rickets.

16. The composition of claim 13 useful for treatment of osteomalacia.

17. The method of claim 8 wherein the analog is the analog LO.

18. The method of claim 8 wherein the analog is the analog HS.

19. The method of claim 8 wherein the analog is the analog EV.

* * * * *